United States Patent
Yamaji

(10) Patent No.: US 11,660,045 B2
(45) Date of Patent: May 30, 2023

(54) COMPUTER-READABLE RECORDING MEDIUM RECORDING DISPLAY PROGRAM FOR DETERMINING LENGTH OF FIRST TIME PERIOD BEFORE SLEEP ONSET, DISPLAY METHOD FOR DETERMINING LENGTH OF FIRST TIME PERIOD BEFORE SLEEP ONSET, AND INFORMATION PROCESSING DEVICE FOR DETERMINING LENGTH OF FIRST TIME PERIOD BEFORE SLEEP ONSET

(71) Applicant: FUJITSU LIMITED, Kawasaki (JP)

(72) Inventor: Takayuki Yamaji, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 190 days.

(21) Appl. No.: 16/893,671

(22) Filed: Jun. 5, 2020

(65) Prior Publication Data
US 2020/0297271 A1    Sep. 24, 2020

Related U.S. Application Data

(63) Continuation of application No. PCT/JP2018/016688, filed on Apr. 24, 2018.

(30) Foreign Application Priority Data

Dec. 25, 2017   (JP) .............................. JP2017-247716

(51) Int. Cl.
*A61B 5/00* (2006.01)
*G06F 3/01* (2006.01)

(52) U.S. Cl.
CPC ............ *A61B 5/4815* (2013.01); *A61B 5/742* (2013.01); *G06F 3/011* (2013.01); *G06F 3/017* (2013.01)

(58) Field of Classification Search
CPC ..... A61B 5/4815; A61B 5/742; A61B 5/1118; A61B 5/4809; A61B 5/11; A61B 5/16;
(Continued)

(56) References Cited

U.S. PATENT DOCUMENTS

2011/0015495 A1    1/2011  Dothie et al.
2013/0268152 A1   10/2013  Koshizen et al.
(Continued)

FOREIGN PATENT DOCUMENTS

| CN | 103371830 | 10/2013 |
| JP | 2001-74292 | 3/2001 |

(Continued)

OTHER PUBLICATIONS

Roger J. Cole et al., "Automatic Sleep/Wake Identification From Wrist Activity", American Sleep Disorders Association and Sleep Research Society, 1992, Sleep, vol. 15, No. 5, pp. 461-469 (Total 9 pages).

(Continued)

*Primary Examiner* — David D Davis
(74) *Attorney, Agent, or Firm* — Fujitsu Patent Center

(57) ABSTRACT

A non-transitory computer-readable recording medium records a display program for causing a computer to perform processes of: acquiring data about a space in which a subject sleeps, the data having been detected by a first sensor installed in the space; and displaying a zone including a sleep zone, a first zone before sleep onset, and a second zone after awakening of the subject in a different mode from other zones, when chronologically displaying suitability of the space as a sleep environment on a basis of the acquired data.

7 Claims, 37 Drawing Sheets

(58) Field of Classification Search
CPC ......... G06F 3/011; G06F 3/017; G16H 20/70; G16H 40/60; G16H 50/30; G16H 10/60; G06Q 50/10
See application file for complete search history.

(56) References Cited

U.S. PATENT DOCUMENTS

| | | | | |
|---|---|---|---|---|
| 2013/0281874 | A1* | 10/2013 | Nishida | A61B 7/003 600/534 |
| 2013/0281883 | A1* | 10/2013 | Nishida | A61B 5/742 600/586 |
| 2013/0338446 | A1 | 12/2013 | Van Vugt et al. | |
| 2014/0323919 | A1* | 10/2014 | Tsutsumi | A61B 7/003 600/586 |
| 2015/0238137 | A1* | 8/2015 | Eyal | A61B 5/6898 600/595 |
| 2016/0027278 | A1* | 1/2016 | McIntosh | G08B 21/0423 715/741 |
| 2016/0151603 | A1* | 6/2016 | Shouldice | A61B 5/4806 600/26 |
| 2017/0251986 | A1* | 9/2017 | Yamaji | G06T 11/206 |
| 2018/0338717 | A1 | 11/2018 | Yamaji | |

FOREIGN PATENT DOCUMENTS

| | | |
|---|---|---|
| JP | 2011-036649 A | 2/2011 |
| JP | 2013-215067 A | 10/2013 |
| JP | 2015-223215 A | 12/2015 |
| JP | 2016-161453 A | 9/2016 |
| JP | 2017-086284 A | 5/2017 |
| JP | 2017-123989 A | 7/2017 |
| JP | 2017-174012 A | 9/2017 |
| JP | 2017-202060 A | 11/2017 |
| WO | 2016/067449 A1 | 5/2016 |
| WO | 2017/168495 A1 | 10/2017 |

OTHER PUBLICATIONS

International Search Report and Written Opinion of the International Searching Authority (Form PCT/ISA/210 and 237), mailed in connection with PCT/JP2018/016688 and dated Jul. 17, 2018 (13 pages).
EESR—The Extended European Search Report of European Patent Application No. 18893468.1 dated Mar. 3, 2021.
Search Report of Patent Application No. 11202005220R issued by Intellectual Property Office of Singapore dated Jul. 13, 2021.
The Written Opinion of Patent Application No. 11202005220R issued by Intellectual Property Office of Singapore dated Jul. 13, 2021.
The Invitation to Respond to Written Opinion and Written Opinion of Patent Application No. 11202005220R in Singapore dated Jan. 12, 2023, 7 pages.
CNOA—Office Action of Chinese Patent Application No. 201880081903.3 dated Mar. 16, 2023 with full English translation.

* cited by examiner

FIG. 4

STORE INFORMATION DB ~400

| STORE ID | STORE NAME | LATITUDE | LONGITUDE | ALTITUDE |
|---|---|---|---|---|
| S1 | YOKOHAMA STORE | 35.46602 | 139.6222 | 16.38416 |
| S2 | TOKYO STORE | 35.68077 | 139.7676 | 7.071398 |
| S3 | MUSASHI NAKAHARA STORE | 35.58121 | 139.641 | 10.69131 |
| S4 | MUSASHI KOSUGI STORE | 35.57636 | 139.6598 | 11.3798 |
| S5 | TAMA PLAZA STORE | 35.57748 | 139.5587 | 50.63904 |
| S6 | SANNOMIYA STORE | 34.69421 | 135.1942 | 17.99457 |

ENVIRONMENT SENSOR INFORMATION DB ~500

| ENVIRONMENT SENSOR ID | DATE | TIME | TEMPERATURE | HUMIDITY | ILLUMINANCE | SOUND PRESSURE |
|---|---|---|---|---|---|---|
| 001 | 2017/12/11 | 19:09 | 27.16 | 41.45 | 1000 | 46.87 |
| 001 | 2017/12/11 | 19:10 | 27.16 | 41.58 | 1000 | 48.71 |
| 001 | 2017/12/11 | 19:11 | 27.16 | 41.75 | 1000 | 48.58 |
| 001 | 2017/12/11 | 19:12 | 27.16 | 41.92 | 1010 | 47.5 |
| 001 | 2017/12/11 | 19:13 | 27.16 | 42.08 | 1010 | 48.84 |
| 001 | 2017/12/11 | 19:14 | 27.16 | 42.35 | 1010 | 47.8 |
| 001 | 2017/12/11 | 19:15 | 27.16 | 42.56 | 1000 | 50.61 |
| 001 | 2017/12/11 | 19:16 | 27.16 | 42.82 | 1000 | 47.43 |
| 001 | 2017/12/11 | 19:17 | 27.16 | 43.02 | 1000 | 48.51 |
| 001 | 2017/12/11 | 19:18 | 27.16 | 43.26 | 990 | 47.27 |
| 001 | 2017/12/11 | 19:19 | 27.16 | 43.49 | 990 | 47.58 |
| 001 | 2017/12/11 | 19:20 | 27.16 | 43.69 | 1000 | 48.37 |
| 001 | 2017/12/11 | 19:21 | 27.16 | 43.82 | 1000 | 47.73 |
| 001 | 2017/12/11 | 19:22 | 27.15 | 40.92 | 1010 | 47.35 |
| 001 | 2017/12/11 | 19:23 | 27.15 | 40.95 | 1020 | 48.23 |
| 001 | 2017/12/11 | 19:24 | 27.16 | 41.01 | 1010 | 50.12 |
| 001 | 2017/12/11 | 19:25 | 27.16 | 41.05 | 1000 | 48.51 |
| 001 | 2017/12/11 | 19:26 | 27.16 | 41.08 | 1000 | 47.73 |
| 001 | 2017/12/11 | 19:27 | 27.15 | 41.11 | 990 | 46.95 |
| 001 | 2017/12/11 | 19:28 | 27.16 | 41.11 | 1000 | 48.64 |
| 001 | 2017/12/11 | 19:29 | 27.16 | 41.05 | 1010 | 47.5 |
| : | : | : | : | : | : | : |

FIG. 6

TEMPERATURE THRESHOLD TABLE ~600

610

| SCORE | SPRING (MARCH TO MAY)/AUTUMN (SEPTEMBER TO NOVEMBER) | | |
|---|---|---|---|
| | EARLIER ZONE | MIDDLE ZONE | LATER ZONE |
| 3 | 20°C≦T<24°C | 19°C≦T<23°C | 21°C≦T<25°C |
| 2 | 16°C≦T<27°C | 16°C≦T<27°C | 17°C≦T<28°C |
| 1 | 16°C>T or 27°C≦T | 16°C>T or 28°C≦T | 17°C>T or 28°C≦T |

620

| SCORE | SUMMER (JUNE TO AUGUST) | | |
|---|---|---|---|
| | EARLIER ZONE | MIDDLE ZONE | LATER ZONE |
| 3 | 24°C≦T<27°C | 24°C≦T<26°C | 24°C≦T<28°C |
| 2 | 21°C≦T<30°C | 21°C≦T<29°C | 23°C≦T<30°C |
| 1 | 21°C>T or 30°C≦T | 21°C>T or 29°C≦T | 23°C>T or 30°C≦T |

630

| SCORE | WINTER (DECEMBER TO FEBRUARY) | | |
|---|---|---|---|
| | EARLIER ZONE | MIDDLE ZONE | LATER ZONE |
| 3 | 16°C≦T<20°C | 15°C≦T<20°C | 16°C≦T<21°C |
| 2 | 12°C≦T<24°C | 11°C≦T<24°C | 12°C≦T<25°C |
| 1 | 12°C>T or 24°C≦T | 11°C>T or 24°C≦T | 12°C>T or 25°C≦T |

FIG. 9

| SCORE | SLEEP ZONE | PRE-SLEEP ZONE | POST-AWAKENING ZONE |
|---|---|---|---|
| 3 | SOUND PRESSURE≦32dB | SOUND PRESSURE≦43dB | SOUND PRESSURE≦43dB |
| 2 | 32dB<SOUND PRESSURE≦42dB | 43dB<SOUND PRESSURE≦55dB | 43dB<SOUND PRESSURE≦55dB |
| 1 | 42dB<SOUND PRESSURE | 55dB<SOUND PRESSURE | 55dB<SOUND PRESSURE |

SOUND PRESSURE THRESHOLD TABLE ~900

FIG. 12

| | ENVIRONMENT SENSOR ID | DATE | TIME | TEMPERATURE | HUMIDITY | ILLUMINANCE | SOUND PRESSURE |
|---|---|---|---|---|---|---|---|
| | ⋮ | ⋮ | ⋮ | ⋮ | ⋮ | ⋮ | ⋮ |
| 1200-1 | 001 | 2017/11/11 | 22:10 | 2 | 1 | 3 | 3 |
| | ... | ... | ... | ... | ... | ... | ... |
| 1200-2 | 001 | 2017/11/12 | 2:10 | 3 | 1 | 2 | 3 |
| | ... | ... | ... | ... | ... | ... | ... |
| 1200-3 | 001 | 2017/11/12 | 7:10 | 3 | 2 | 3 | 2 |
| | ... | ... | ... | ... | ... | ... | ... |
| 1200-4 | 001 | 2017/11/12 | 8:10 | 3 | 2 | 3 | 3 |
| | ⋮ | ⋮ | ⋮ | ⋮ | ⋮ | ⋮ | ⋮ |

EVALUATION RESULT TABLE 1200

FIG. 13

COMPREHENSIVE EVALUATION TABLE ~1300

| ENVIRONMENT SENSOR ID | DATE | TEMPERATURE | HUMIDITY | ILLUMINANCE | SOUND PRESSURE | OVERALL |
|---|---|---|---|---|---|---|
| ... | ... | ... | ... | ... | ... | ... |
| 001 | 2017/11/11 | 2 | 2 | 3 | 3 | 3 |
| 001 | 2017/11/12 | 2 | 1 | 2 | 3 | 2 |
| ... | ... | ... | ... | ... | ... | ... |

1300-1
1300-2

COMPUTER-READABLE RECORDING MEDIUM RECORDING DISPLAY PROGRAM FOR DETERMINING LENGTH OF FIRST TIME PERIOD BEFORE SLEEP ONSET, DISPLAY METHOD FOR DETERMINING LENGTH OF FIRST TIME PERIOD BEFORE SLEEP ONSET, AND INFORMATION PROCESSING DEVICE FOR DETERMINING LENGTH OF FIRST TIME PERIOD BEFORE SLEEP ONSET

CROSS-REFERENCE TO RELATED APPLICATION

This application is a continuation application of International Application PCT/JP2018/016688 filed on Apr. 24, 2018 and designated the U.S., the entire contents of which are incorporated herein by reference. The International Application PCT/JP2018/016688 is based upon and claims the benefit of priority of the prior Japanese Patent Application No. 2017-247716, filed on Dec. 25, 2017, the entire contents of which are incorporated herein by reference.

FIELD

The embodiment relates to a display program, a display method, and a display device.

BACKGROUND

There have been services for provide consultations about sleep environments to improve the quality of sleep. For example, there is a service in which a customer is asked to fill out a predetermined questionnaire about the current sleeping time, lifestyle, and the like, and a staff member finds out aspects that need improvement from the contents written in the questionnaire, and gives advice to the customer.

Related art is disclosed in Japanese Laid-open Patent Publication No. 2011-36649, International Publication Pamphlet No. WO 2016/067449 and International Publication Pamphlet No. WO 2017/168495.

SUMMARY

According to an aspect of the embodiments, a non-transitory computer-readable recording medium records a display program for causing a computer to perform processes of: acquiring data about a space in which a subject sleeps, the data having been detected by a first sensor installed in the space; and displaying a zone including a sleep zone, a first zone before sleep onset, and a second zone after awakening of the subject in a different mode from other zones, when chronologically displaying suitability of the space as a sleep environment on a basis of the acquired data.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 is an explanatory diagram illustrating an example of the contents stored in a store information DB 400.

FIG. 5 is an explanatory diagram illustrating an example of the contents stored in an environment sensor information DB 500.

FIG. 6 is an explanatory diagram illustrating an example of the contents stored in a temperature threshold table 600.

FIG. 9 is an explanatory diagram illustrating an example of the contents stored in a sound pressure threshold table 900.

FIG. 12 is an explanatory diagram illustrating an example of the contents stored in an evaluation result table 1200.

FIG. 13 is an explanatory diagram illustrating an example of the contents stored in a comprehensive evaluation table 1300.

DESCRIPTION OF EMBODIMENTS

A system monitors one or more objective parameters related to the quality of sleep of a user in bed, and, through a portable device, receives feedback of objective test data about cognitive and/or psychomotor ability from the user when he/she is awake.

Technical Problem

By any conventional technique, however, it is difficult to assess the suitability of a sleeping space as a sleep environment. For example, in providing consultation about a sleep environment, it is not possible to give appropriate advice for increasing the quality of sleep, unless the suitability of the space in which the customer sleeps can be accurately assessed.

In one aspect, an easy-to-understand display of the suitability of a space as a sleep environment, not only in the sleep zone, but also in the pre-sleep and post-sleep zones that affect sleep may be provided.

The following is a detailed description of embodiments of a display program, a display method, and a display device according to the present invention, with reference to the drawings.

EMBODIMENTS

Figure 1:
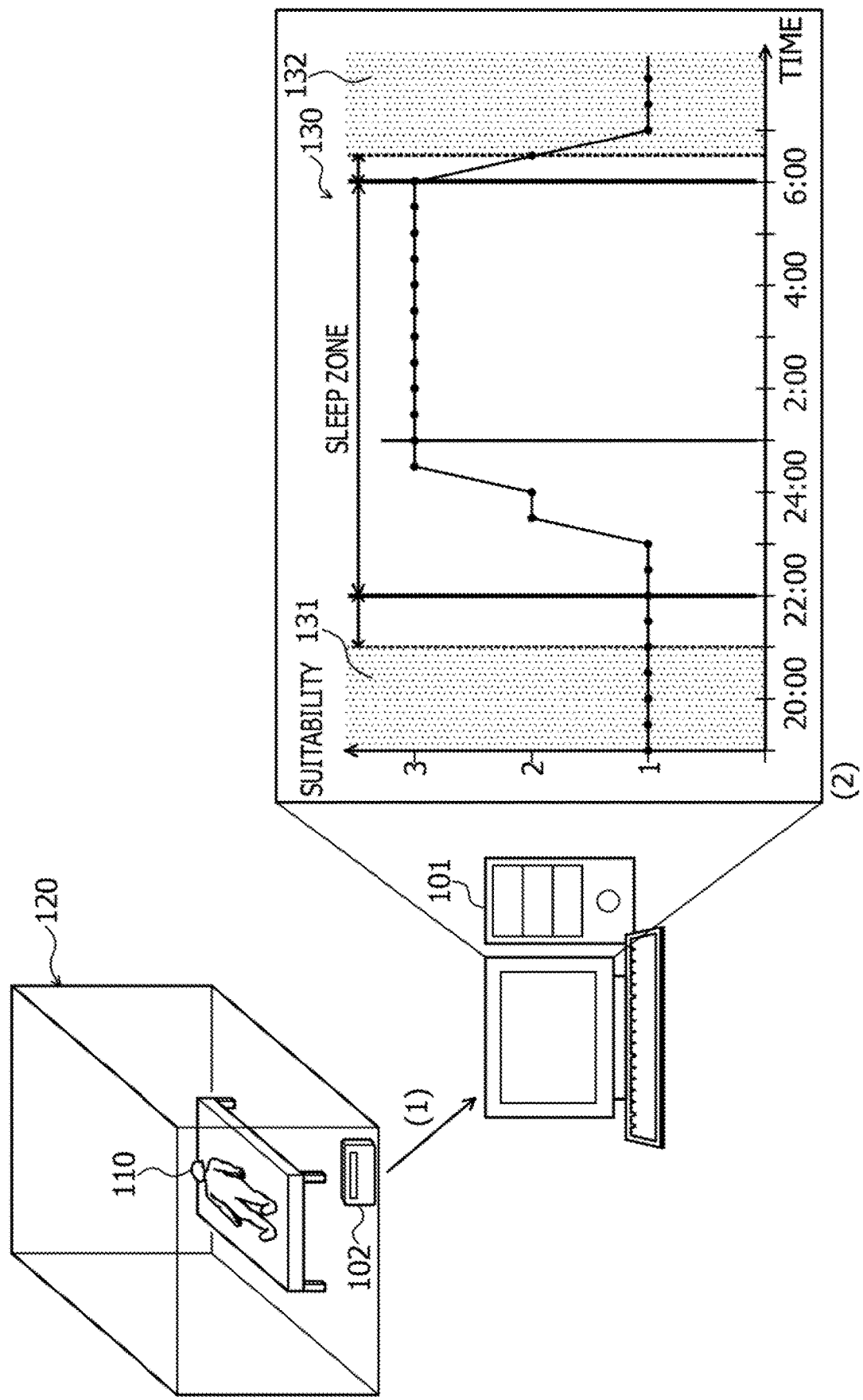
FIG. 1 is an explanatory diagram illustrating an example of a display method according to an embodiment.

FIG. 1 is an explanatory diagram illustrating an example of a display method according to an embodiment. In FIG. 1, a display device 101 is a computer that chronologically displays the suitability of a space in which the subject sleeps as a sleep environment. The subject is a person who sleeps in a space to be analyzed as a sleep environment. A space in which the subject sleeps is a bedroom at the subjects home, a nap room at work, a bedroom at an accommodation facility, or the like, for example. Further, the suitability of a space as a sleep environment is an index indicating how well the environment is suited for sleeping.

Here, to improve the sleep environment, it is important to accurately assess the suitability of the space as a sleep environment in which the subject sleeps. The suitability of the space as a sleep environment can be evaluated on the basis of the temperature, the humidity, the brightness, the loudness, and the like of the space, for example. Furthermore, since the temperature and the like of a space changes over time, the suitability of the space as a sleep environment also changes over time.

Therefore, to determine whether the sleep environment is good or bad, the suitability at least in the sleep zone from sleep onset to awakening is checked. Further, to increase the quality of sleep, the environments before sleep onset and after awakening are also important. For example, depending on the environment before sleep onset or after awakening, the speed of falling asleep or awakening might be low. For this reason, it is desirable to determine the suitability of the space as a sleep environment, not only from the sleep zone but also from the pre-sleep zone and the post-awakening zone.

However, simply displaying the suitability of the space as a sleep environment in chronological order makes it difficult for a viewer to recognize which portion corresponds to the sleep zone. Likewise, it is difficult to recognize the pre-sleep and post-awakening zones. Furthermore, some viewers might not understand how long the pre-sleep and post-awakening zones indicate the suitability that should be referred to.

Therefore, this embodiment concerns a display method that provides an easy-to-understand display of the suitability of a space as a sleep environment, not only in the sleep zone, but also in the pre-sleep and post-sleep zones that affect sleep. In the description below, an exemplary process to be performed by the display device 101 is explained. In the example case illustrated in FIG. 1, a sensor 102 is provided in a space 120 in which a subject 110 sleeps. The space 120 is a bedroom of the home of the subject 110, for example.

(1) The display device 101 acquires data about the space 120 detected by the sensor 102. The sensor 102 is a device that detects data about the space 120. Data about the space 120 indicates at least the temperature, the humidity, the illuminance, or the sound pressure of the space 120, or any combination thereof, for example.

Specifically, the display device 101 may directly acquire data about the space 120 from the sensor 102 via a wired or wireless network, for example. Alternatively, the display device 101 may acquire data about the space 120 detected by the sensor 102, via another computer connected to the sensor 102.

(2) When chronologically displaying the suitability of the space 120 as a sleep environment on the basis of the data acquired from the sensor 102, the display device 101 displays the zone including the sleep zone, a first zone before sleep onset, and a second zone after awakening of the subject 110, in a different manner from the other zones.

The suitability of the space 120 as a sleep environment is evaluated on the basis of the temperature, the humidity, the illuminance, or the sound pressure of the space 120 indicated by the data from the sensor 102, or any combination thereof, for example. Note that the process of evaluating the suitability of the space 120 as a sleep environment on the basis of the data from the sensor 102 may be performed in the display device 101, or may be performed in another computer connected to the display device 101, for example.

The sleep zone of the subject 110 is the time period from when the subject 110 falls asleep until when the subject 110 wakes up. Sleep onset means starting to sleep, and shifting from a conscious state to a sleeping state. Waking up means awakening from sleep, and shifting from a sleeping state to a conscious state. Here, there might be a time lag between when the subject 100 goes to bed to sleep and when he/she actually starts sleeping, or between when he/she wakes up and when he/she leaves the bed. In a case where data about the respective times of going to bed, the start of sleep, the end of sleep (awakening), and leaving bed can be obtained, the bed zone from going to bed till leaving the bed, or the zone from the start of sleep till the end of sleep can be used as the sleep zone.

The first zone before sleep onset is the time period immediately before sleep onset. The second zone after waking up is the time period immediately after waking up. The lengths of the first and second zones can be set as appropriate, and may be determined by how much of the environment during the time before sleep onset and after awakening should be considered increasing the quality of sleep, for example. For example, the first zone is set to a length of about one hour. Meanwhile, the second zone is set to a length of about 30 minutes.

In the example illustrated in FIG. 1, the sleep zone of the subject 110 is "22:00 to 6:00". Meanwhile, the first zone before sleep onset is "21:00 to 22:00". Further, the second zone after waking up is "6:00 to 6:30". Note that the lengths of the first and second zones may be determined from the sleeping time or the like of the subject 110 on the day before, as will be described later.

Here, the manner in which the chronological change in the suitability of the space 120 as a sleep environment is indicated can be set as appropriate, and may be represented by a band graph or a line graph, for example. Also, the manner in which the zone including the sleep zone, the first zone, and the second zone is displayed so as to be different from the other zones can be set as appropriate.

For example, there may be a case where the chronological change in the suitability of the space 120 as a sleep environment is represented by a band graph having different colors or patterns depending on the degrees of suitability. In this case, the display device 101 may put shading on the band graph for the zones other than the zone including the sleep zone, the first one, and the second zone.

For example, there may be a case where the chronological change in the suitability of the space 120 as a sleep environment is represented by a line graph. In this case, the display device 101 may use a line graph of a different line type for the zone including the sleep zone, the first zone, and the second zone, from the line type for the other zones. For example, the line type for the zone including the sleep zone, the first zone, and the second zone may be a solid line, and the line type for the other zones may be a dotted line.

In the example illustrated in FIG. 1, the chronological change in the suitability of the space 120 as a sleep environment is indicated by a line graph 130. Here, the suitability as a sleep environment is represented by one of the values from 1 to 3. The greater the value, the higher the suitability. Further, the zones other than the zone including the sleep zone, the first zone before sleep onset, and the second zone after awakening of the subject 110 are shaded (portions 131 and 132 in FIG. 1) in the line graph 130.

As described above, when chronologically displaying the suitability of the space 120 as a sleep environment, the display device 101 can display the zone including the sleep zone, the first zone before sleep onset, and the second zone after awakening of the subject 110, in a different manner from the other zone. Accordingly, it is possible to provide an easy-to-understand display of the suitability of the space 120 as a sleep environment, not only in the sleep zone, but also in the pre-sleep and post-sleep zones that affect sleep.

In the example illustrated in FIG. 1, the line graph 130 chronologically indicates the suitability of the space 120 as a sleep environment at intervals of 30 minutes. According to the line graph 130, the user can recognize the chronological change in the suitability of the space 120 as a sleep environment. In this case, from the shaded display (the portions 131 and 132) in the line graph 130, the user can easily recognize the entire zone "21:00 to 6:30" that affects sleep. As a result, the user understands that the suitability in the first zone "21:00 to 22:00" before sleep onset and the earlier zone "22:00 to 23:00" of the sleep zone is lower than in the other zones, for example, and therefore, some measures should be taken to improve sleep.

(Exemplary System Configuration of Sleep Environment Analysis System 200)

Next, an exemplary system configuration of the sleep environment analysis system 200 according to the embodiment is described. In the description below, a case where the sleep environment analysis system 200 is used in a service for providing consultation about a sleep environment is described as an example.

Figure 2:
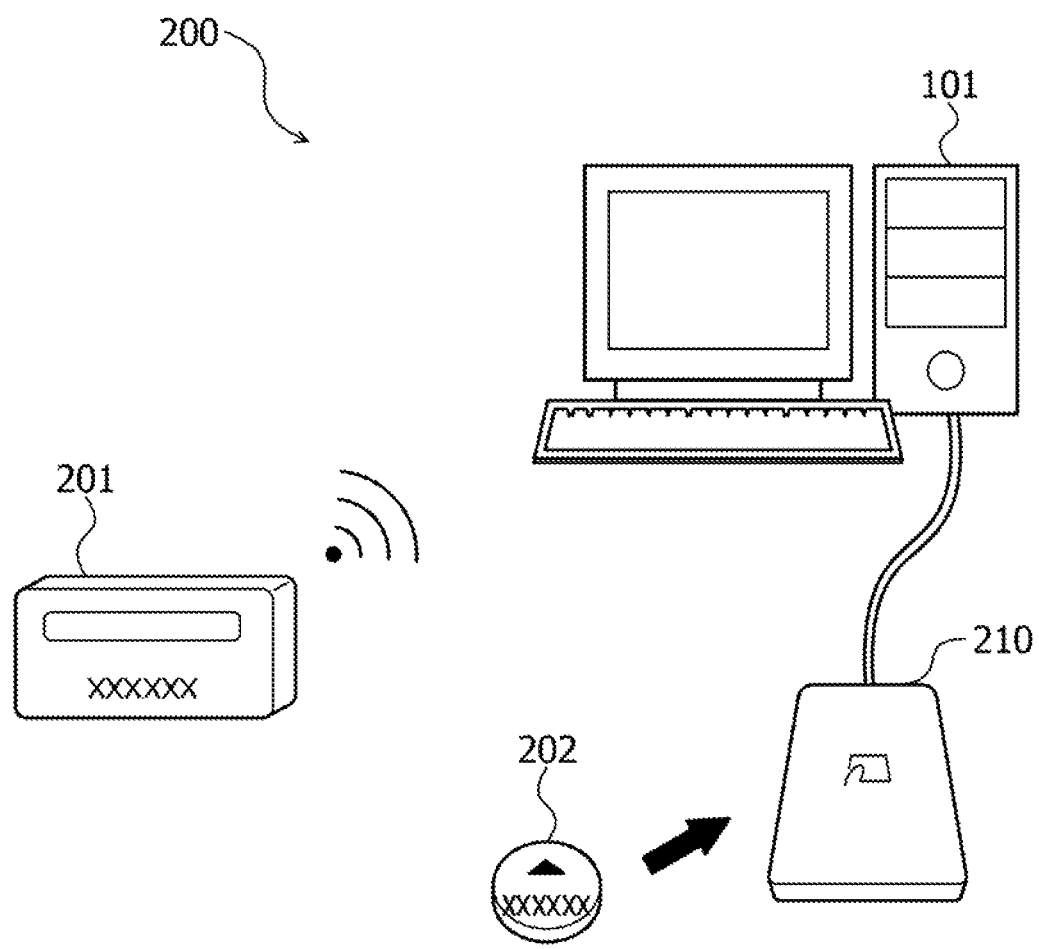
FIG. 2 is an explanatory diagram illustrating an exemplary system configuration of a sleep environment analysis system 200.

FIG. 2 is an explanatory diagram illustrating an exemplary system configuration of the sleep environment analysis system 200. In FIG. 2, the sleep environment analysis system 200 includes the display device 101, an environment sensor 201, and an activity meter 202. In the sleep environment analysis system 200, the display device 101 is installed in a store that provides services. For example, the display device 101 is a personal computer (PC) or a tablet PC that is used by store staff. Meanwhile, the environment sensor 201 and the activity meter 202 are lent out to a customer who is the subject. The environment sensor 201 is installed in the space in which the subject sleeps. The activity meter 202 is worn by the subject. In the description below, the space where the subject sleeps will sometimes be referred to as the "space R".

Here, the environment sensor 201 is a sensor that detects data relating to temperature, humidity, illuminance, and sound pressure. The intervals in data detection to be performed by the environment sensor 201 can be set as appropriate, and may be time intervals of about one minute, for example. Data detected by the environment sensor 201 is stored into an internal memory. In the environment sensor 201, data of about one week can be accumulated, for example.

The environment sensor 201 is also capable of near field communication. Near field communication is wireless communication having a communication distance of several meters to several tens of meters. Examples of near field communication include communication using a wireless local area network (LAN), Bluetooth (registered trademark), or the like, Note that the sensor 102 illustrated in FIG. 1 corresponds to the environment sensor 201, for example. Further, the environment sensor 201 is an example of the first sensor installed in the space R.

The activity meter 202 is a device that measures the activities of the subject. The intervals in data collection to be performed by the activity meter 202 can be set as appropriate, and may be time intervals of about 10 seconds, for example. Specifically, the activity meter 202 has a triaxial accelerometer, and records data relating to movement and orientation of the subjects body into an internal memory, for example. In the activity meter 202, data of about one week can be accumulated, for example. In the example illustrated in FIG. 2, the activity meter 202 is a coin-type device attached to the subjects waist or the like. However, the activity meter 202 may be of a wristband type, a pendant type, a badge type, or the like. The activity meter 202 is an example of the second sensor that senses data relating to activities of the subject.

In the sleep environment analysis system 200, the display device 101 can acquire data detected by the environment sensor 201 from the environment sensor 201 through near field communication. The display device 101 also includes a reading device 210, and is capable of reading data recorded the activity meter 202. The reading device 210 may be a non-contact IC integrated circuit (IC) card reader, for example.

For example, when the subject (customer) carrying the environment sensor 201 and the activity meter 202 visits the store to receive a service, the display device 101 acquires data from the environment sensor 201 through near field communication. Further, when a store staff member or the customer holds the activity meter 202 over the reading device 210, the data recorded in the activity meter 202 is read by the display device 101.

Note that, in the example illustrated in FIG. 2, only one display device 101 is illustrated. However, one display device 101 is installed in each store that provides services, for example. Further, in the example illustrated in FIG. 2, only one environment sensor 201 and one activity meter 202 are illustrated, but one environment sensor 201 and one activity meter 202 are lent out to each customer (subject). However, the environment sensor 201 and the activity meter 202 may be sold or distributed free of charge to customers (subjects).

(Exemplary Hardware Configuration of Display Device 101)

Figure 3:
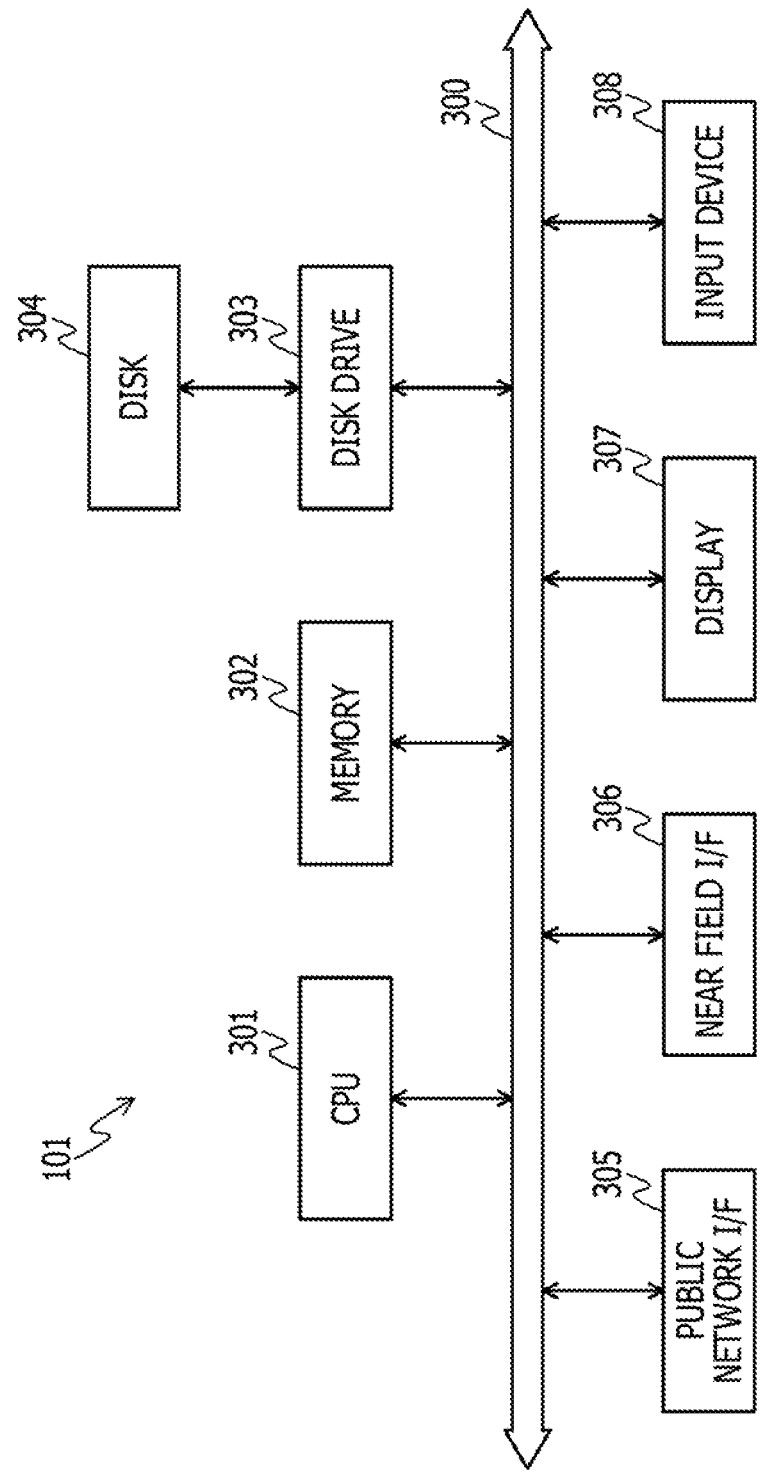
FIG. 3 is a block diagram illustrating an exemplary hardware configuration of a display device 101.

FIG. 3 is a block diagram illustrating an exemplary hardware configuration of the display device 101. In FIG. 3, the display device 101 includes a central processing unit (CPU) 301, a memory 302, a disk drive 303, a disk 304, a public network interface (I/F) 305, a near field wireless I/F 306, a display 307, and an input device 308. Furthermore, the respective components are connected to one another via a bus 300.

Here, the CPU 301 controls the entire display device 101. The memory 302 is a storage unit inducting a read only memory (ROM), a random access memory (RAM), a flash ROM, and the like, for example. Specifically, the flash ROM and the ROM stores various kinds of programs, while the RAM is used as a work area for the CPU 301, for example. A program stored in the memory 302 is loaded into the CPU 301, to cause the CPU 301 to execute a coded process.

The disk drive 303 controls reading and writing of data from and into the disk 304, under the control of the CPU 301. The disk 304 stores the data written under the control of the disk drive 303. The disk 304 may be a magnetic disk, an optical disk, or the like, for example.

The public network I/F 305 includes a wireless communication circuit and an antenna, is connected to a network, and is connected to another computer via the network. The network is a LAN, a wide area network (WAN), the Internet, or the like, for example. The public network I/F 305 then manages an interface between the network and the inside, and controls input and output of data from another computer.

The near field wireless I/F 306 includes a wireless communication circuit and an antenna, is connected to a wireless network, and is connected to another computer (the environment sensor 201 illustrated in FIG. 2, for example) via the wireless network. The near field wireless I/F 306 then manages an interface between the wireless network and the inside, and controls input and output of data from another computer.

The display 307 is a display device that displays data such as a document, an image, function information, or the like, as well as a cursor and icons or tool boxes. The display 307 may be a liquid crystal display, an organic electroluminescence (EL) display, or the like, for example.

The input device 308 includes keys for inputting characters, numbers, various kinds of instructions, and the like, and inputs data. The input device 308 may be a keyboard, a mouse, or the like, or may be a touch-panel input pad, a numeric keypad, or the like.

Note that the display device 101 may not include the disk drive 303, the disk 304, and the like of the components described above, for example. Further, the display device 101 may include a solid-state drive (SSD), a scanner, a printer, and the like, for example, in addition to the components described above.

(Contents Stored in Store Information DB 400)

Next, the contents stored in a store information database (DB) 400 that is used by the display device 101 are described. The store information DB 400 is formed with storage devices such as the memory 302, the disk 304, and the like illustrated in FIG. 3, for example. Alternatively, the store information DB 400 may be included in another computer that can be accessed by the display device 101. In that case, the display device 101 can refer to the contents stored in the store information DB 400 by accessing the other computer.

FIG. 4 is an explanatory diagram illustrating an example of the contents stored in the store information DB 400. In FIG. 4, the store information DB 400 has fields of store IDs, store names, latitudes, longitudes, and altitudes, and stores records of store information 400-1 through 400-6 by setting information in the respective fields.

Here, a store ID is an identifier that uniquely identifies a store that provides a service for providing consultation about a sleep environment. A store name is the name of a store, A latitude, a longitude, and an altitude are the latitude, the longitude, and the altitude of the point at which a store is located. For example, the store information 400-1 indicates the store name "Yokohama store", the latitude "35.46602", the longitude "139.6222", and the altitude "16.38416" of a store SI.

(Contents Stored in Environment Sensor Information DB 500)

Next, the contents stored in an environment sensor information DB 500 that is used by the display device 101 are described. The environment sensor information DB 500 is formed with storage devices such as the memory 302, the disk 304, and the like, for example.

FIG. 5 is an explanatory diagram illustrating an example of the contents stored in the environment sensor information DB 500. In FIG. 5, the environment sensor information DB 508 has fields of environment sensor ID, date, time, temperature, humidity, illuminance, and sound pressure, and stores records of environment sensor information (environment sensor information 500-1 through 500-21, for example) by setting information in the respective fields.

Here, an environment sensor ID is the identifier that uniquely identifies the environment sensor 281. A date is the date on which temperature and the like were detected by the environment sensor 201. A time is a time at which a temperature and the like were detected by the environment sensor 201. A temperature is a temperature detected by the environment sensor 281 (unit: ° C.). A humidity is a humidity detected by the environment sensor 201 (unit: %). An illuminance is an illuminance detected by the environment sensor 201 (unit: Lx). A sound pressure is a sound pressure detected by the environment sensor 201 (unit: dB).

For example, the environment sensor information 500-1 indicates the temperature "27.16", the humidity "41.45", the illuminance "1000", and the sound pressure "46.87" detected at "2017/12/11 19:09" by the environment sensor 201 of the environment sensor ID "001".

(Contents Stored in Temperature Threshold Table 600)

Next, the contents stored in a temperature threshold table 600 that is used by the display device 101 are described. The temperature threshold table 600 is formed with storage devices such as the memory 302, the disk 304, and the like, for example.

FIG. 6 is an explanatory diagram illustrating an example of the contents stored in the temperature threshold table 600. In FIG. 6, the temperature threshold table 600 stores evaluation criteria relating to temperature for evaluating the suitability of the space R as a sleep environment. Specifically, the temperature threshold table 600 includes a temperature threshold table (spring/autumn) 610, a temperature threshold table (summer) 620, and a temperature threshold table (winter) 630.

The temperature threshold table (spring/autumn) 610 indicate evaluation criteria for spring/autumn. The temperature threshold table (summer) 620 indicates evaluation criteria for summer. The temperature threshold table (winter) 630 indicates evaluation criteria for winter. In each of the temperature threshold tables 610, 620, and 630, a score indicates a suitability of the space R as a sleep environment. The higher the score, the higher the suitability of the space R as a sleep environment.

Further, in each of the temperature threshold tables 610, 620, and 630, the evaluation criteria in the earlier zone are the evaluation criteria to be applied to (the earlier zone of) the sleep zone. The sleep zone (earlier zone) is the earlier zone of three zones obtained by dividing the sleep zone of the subject. The evaluation criteria in the middle zone are the evaluation criteria to be applied to (the middle zone of) the sleep zone. The sleep zone (middle zone) is the middle zone of the three zones obtained by dividing the sleep zone of the subject. The evaluation criteria in the later zone are the evaluation criteria to be applied to (the later zone of) the sleep zone. The sleep zone (later zone) is the later zone of the three zones obtained by dividing the sleep zone of the subject.

Note that the temperature threshold table 600 may include evaluation criteria relating to temperature in each of the zones including the pre-sleep zone, the post-awakening zone, and the livelihood zone. Alternatively, the evaluation criteria relating to temperature in the sleep zone may be used as the evaluation criteria relating to temperature in the pre-sleep zone, the post-awakening zone, and the livelihood zone. The temperature threshold table 600 may also include evaluation criteria for a sleep zone (including a sunrise) and evaluation criteria for a sleep zone (including a sunset). Further, the scores (the degrees of suitability) are in the range of 1 to 3, but any range may be set as appropriate. For example, the range of scores may be from 1 to 5, and evaluation criteria corresponding to each score may be set. The temperature threshold table 600 may further include evaluation criteria relating to temperature in the livelihood zone.

(Contents Stored in Humidity Threshold Table 700)

Next, the contents stored in a humidity threshold table 700 that is used by the display device 101 are described. The humidity threshold table 700 is formed with storage devices such as the memory 302, the disk 304, and the like, for example.

Figure 7:
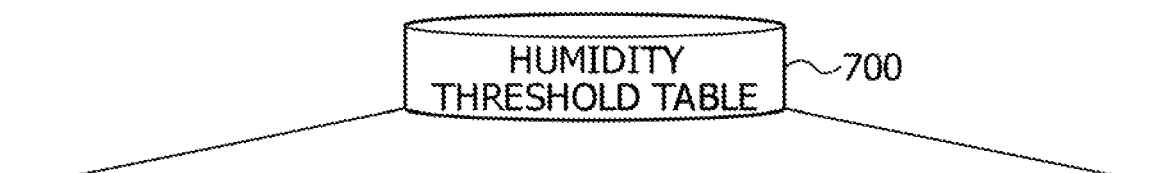
FIG. 7 is an explanatory diagram illustrating an example of the contents stored in a humidity threshold table 700.

FIG. 7 is an explanatory diagram illustrating an example of the contents stored in the humidity threshold table 700. In FIG. 7, the humidity threshold table 700 stores evaluation criteria relating to humidity for evaluating the suitability of the space R as a sleep environment. Note that, although only the evaluation criteria for spring and autumn are illustrated in the example illustrated FIG. 7, the evaluation criteria for summer and winter are also stored in the humidity threshold table 700.

The humidity threshold table 700 may also include evaluation criteria relating to humidity in each of the zones including the pre-sleep zone, the post-awakening zone, and the livelihood zone. Alternatively, the evaluation criteria relating to humidity in the sleep zone may be used as the evaluation criteria relating to humidity in the pre-sleep zone, the post-awakening zone, and the livelihood zone. The humidity threshold table 700 may also include evaluation criteria for a sleep zone (including a sunrise) and evaluation criteria for a sleep zone (including a sunset). The humidity threshold table 700 may further include evaluation criteria relating to humidity in the livelihood zone.

(Contents Stored in Illuminance Threshold Table 800)

Next, the contents stored in an illuminance threshold table 800 that is used by the display device 101 are described. The illuminance threshold table 800 is formed with storage devices such as the memory 302, the disk 304, and the like, for example.

Figure 8:
FIG. 8 is an explanatory diagram illustrating an example of the contents stored in an illuminance threshold table 800.

FIG. 8 is an explanatory diagram illustrating an example of the contents stored in the illuminance threshold table 800. In FIG. 8, the illuminance threshold table 800 stores evaluation criteria relating to illuminance for evaluating the suitability of the space R as a sleep environment. Although the evaluation criteria for the whole year are described as an example herein, the evaluation criteria for each season may be stored.

In the illuminance threshold table 800, the evaluation criteria n the sleep zone are the evaluation criteria to be applied to the time period from the time when the subject falls asleep to the time when the subject wakes up. The evaluation criteria in the pre-sleep zone are the evaluation criteria to be applied to the time period immediately before the subject falls asleep. The evaluation criteria in the post-awakening zone are the evaluation criteria to be applied to the time period immediately after the subject wakes up.

Further, the evaluation criteria in the sleep zone (including a sunrise) are the evaluation criteria to be applied to the time period after the sunrise time in the sleep zone in a case where the sleep zone includes the sunrise time. The evaluation criteria in the sleep zone (including a sunset) are the evaluation criteria to be applied to the time period before the sunset time in the sleep zone in a case where the sleep zone includes the sunset time.

Note that the illuminance threshold table 800 may include the evaluation criteria to be applied to each of the sleep zone (earlier zone), the sleep zone (middle zone), and the sleep zone (later zone). The illuminance threshold table 800 may further include evaluation criteria relating to illuminance in the livelihood zone.

(Contents Stored in Sound Pressure Threshold Table 900)

Next, the contents stored in a sound pressure threshold table 900 that is used by the display device 101 are described. The sound pressure threshold table 900 is formed with storage devices such as the memory 302, the disk 304, and the like, for example.

FIG. 9 is an explanatory diagram illustrating an example of the contents stored in the sound pressure threshold table 900. In FIG. 9, the sound pressure threshold table 900 stores evaluation criteria relating to sound pressure for evaluating the suitability of the space R as a sleep environment. Although the evaluation criteria for the whole year are described as an example herein, the evaluation criteria for each season may be stored.

The sound pressure threshold table 900 may also include the evaluation criteria to be applied to each of the sleep zone (earlier zone), the sleep zone (middle zone), and the sleep zone (later zone). The sound pressure threshold table 900 may also include evaluation criteria for the sleep zone (including a sunrise) and evaluation criteria for the sleep zone (including a sunset). The sound pressure threshold table 900 may further include evaluation criteria relating to sound pressure in the livelihood zone.

(Exemplary Functional Configuration of Display Device 101)

Figure 10:
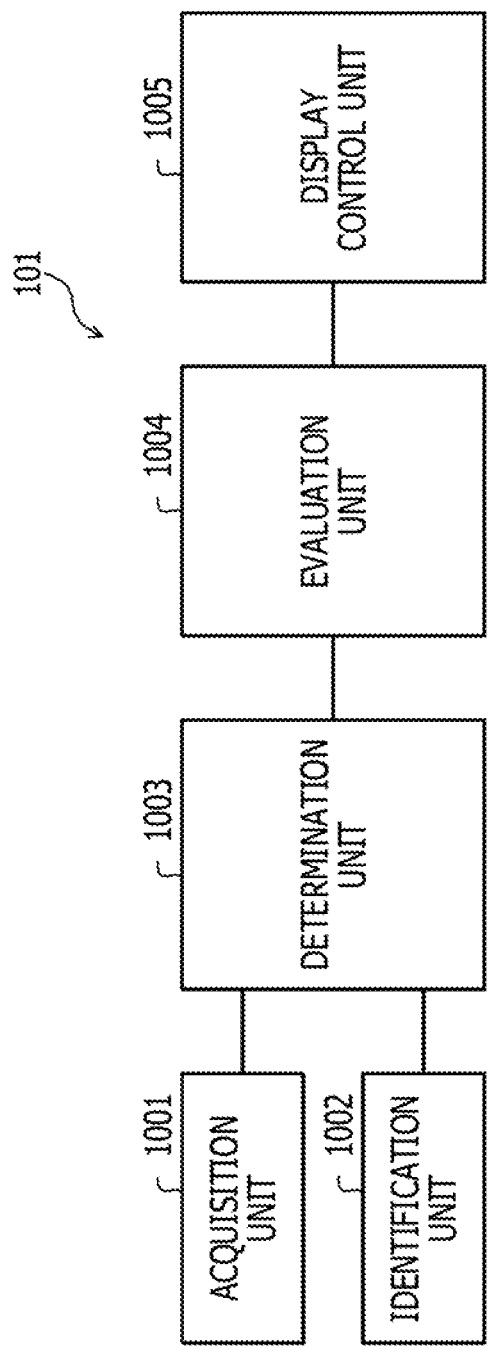
FIG. 10 is a block diagram illustrating an exemplary functional configuration of the display device 101.

FIG. 10 is a block diagram illustrating an exemplary functional configuration of the display device 101. In FIG. 10, the display device 101 includes an acquisition unit 1001, an identification unit 1002, a determination unit 1003, an evaluation unit 1004, and a display control unit 1005. The acquisition unit 1001 to the display control unit 1005 function as an example of the control unit. Specifically, the acquisition unit 1001 to the display control unit 1005 achieve the functions by causing the CPU 301 to execute the programs stored in a storage device such as the memory 302 or the disk 304 illustrated in FIG. 3, or through the public network I/F 305 or the near field wireless I/F 306, for example. The processing results of each functional unit are stored into a storage device such as the memory 302 or the disk 304, for example.

The acquisition unit 1001 acquires data about the space R detected by the environment sensor 201 installed in the space R in which the subject sleeps. Here, the data about the space R indicates the temperature, the humidity, the illuminance, or the sound pressure of the space R, or any combination thereof. For example, the data about the space R is the environment sensor information 500-1 through 500-21 illustrated in FIG. 5.

Specifically, the acquisition unit 1001 acquires environment sensor information by receiving the environment sensor information from the environment sensor 201 through near field communication, for example. The environment sensor information includes information indicating the temperature, the humidity, the illuminance, and the sound pressure of the space R detected by the environment sensor 201. In the environment sensor 201, the environment sensor information about the day on which the environment sensor 201 was lent to the subject (customer) till the current day is recorded, for example. The acquired environment sensor information is stored into the environment sensor information DB 500 illustrated in FIG. 5, for example.

The acquisition unit 1001 also acquires the activity amount data recorded in the activity meter 202 corresponding to the subject. Here, the activity amount data is time series data relating to movement and orientation of the subjects body. Specifically, the acquisition unit 1001 acquires activity amount data by reading the activity amount data from the activity meter 202, using the reading device 210 illustrated in FIG. 2, for example.

The identification unit 1002 identifies the sleep zone of the subject. Here, the sleep zone is the zone from when the subject fails asleep to when the subject wakes up. Specifically, the identification unit 1002 may identify the sleep zone of the subject by accepting information for identifying the sleep zone through an operation input conducted by a user using the input device 308 illustrated in FIG. 3, for example.

The identification unit 1002 may also detect sleep onset and awakening of the subject, on the basis of the activity amount data acquired from the activity meter 202, for example. The identification unit 1002 may then identify the sleep zone of the subject, on the basis of the result of the detection.

More specifically, on the basis of activity amount data, the identification unit 1002 determines that the subject is in an awake state if the subject has a certain amount or more of movement per unit time, and that the subject is in a sleep state if the subject does not have the certain amount or more of movement per unit time, for example On the basis of the result of the determination, the identification unit 1002 may then detect sleep onset and awakening of the subject, and identify the sleep zone. Note that the subject might temporarily become awake during sleep. Therefore, in identifying the sleep zone, the identification unit 1002 may determine that the subject is in a sleep state in a case where the subject is not in an awake state continuously at least for a certain period of time, for example.

Note that any existing technique may be used as a technique for detecting sleep onset and awakening of the subject, from the activity amount data acquired from the activity meter 202. For example, the non-patent document mentioned below can be referred to as a technique for detecting sleep and wakefulness of the subject from activity amount data. Further, the identification unit 1002 may analyze an image captured by a camera installed in the space R, for example, and detect sleeping behaviors and awakening behaviors of the subject, to identify the sleep zone of the subject.

Roger J. Cole et al. 1992. Automatic Sleep/Wake Identification From Wrist Activity. American Sleep Disorders Association and Sleep Research Society. 15(5):461-469

The identification unit 1002 also identifies the times relating to sunrise and sunset. Here, for example, the time relating to sunrise is the time when the upper edge of the sun meets the horizon while rising up, which is the time of a sunrise. Also, for example, the time relating to sunset is the time when the upper edge of the sun meets the horizon while setting, which is the time of a sunset.

Specifically, the identification unit 1002 may identify the times relating to sunrise and sunset by receiving the sunrise and sunset times at the point at which the space R is located, through an operation input conducted by a user using the input device 308, for example. Alternatively, the identification unit 1002 may identify the sunrise and sunset times at the point at which the space R is located, by making an inquiry to a server that discloses or calculates the sunrise and sunset times of various locations.

Further, the identification unit 1002 may identify the time relating to sunrise and sunset, by calculating the sunrise and sunset times at the point at which the space R is located. More specifically, the identification unit 1002 refers to the store information DB 400 illustrated in FIG. 4, to identify the latitude, the longitude, and the altitude of the store in which the device is installed, for example. The identification unit 1002 then calculates the sunrise and sunset times at the point at which the space R is located, on the basis of the identified latitude, longitude, and altitude of the store. In other words, the sunrise and sunset times at the point at which the space R is located are calculated, on the premise that the space R is located at a place close to the store.

The determination unit 1003 determines the length of the pre-sleep zone. Here, the pre-sleep zone corresponds to the first zone described above with reference to FIG. 1, and is the time period immediately before sleep onset, which affects the quality of sleep. The determination unit 1003 also determines the length of the post-awakening zone. Here, the post-awakening zone corresponds to the second zone described above with reference to FIG. 1, and is the time period immediately after the subject awakens, which affects the quality of sleep.

Specifically, the determination unit 1003 may determine the lengths of the pre-sleep zone and the post-awakening zone to be respective predetermined reference lengths, for example. The predetermined reference length of the pre-sleep zone is about one hour, and the predetermined reference length of the post-awakening zone is about 30 minutes, for example.

Alternatively, the determination unit 1003 may determine the lengths of the pre-sleep zone and the post-awakening zone, on the basis of sleep efficiency based on the sleeping time and the time in bed of the subject. Sleep efficiency is an index indicating how efficiently sleep is taken. Sleep efficiency is represented by the ratio of the sleeping time to the time in bed, for example.

Figure 11:
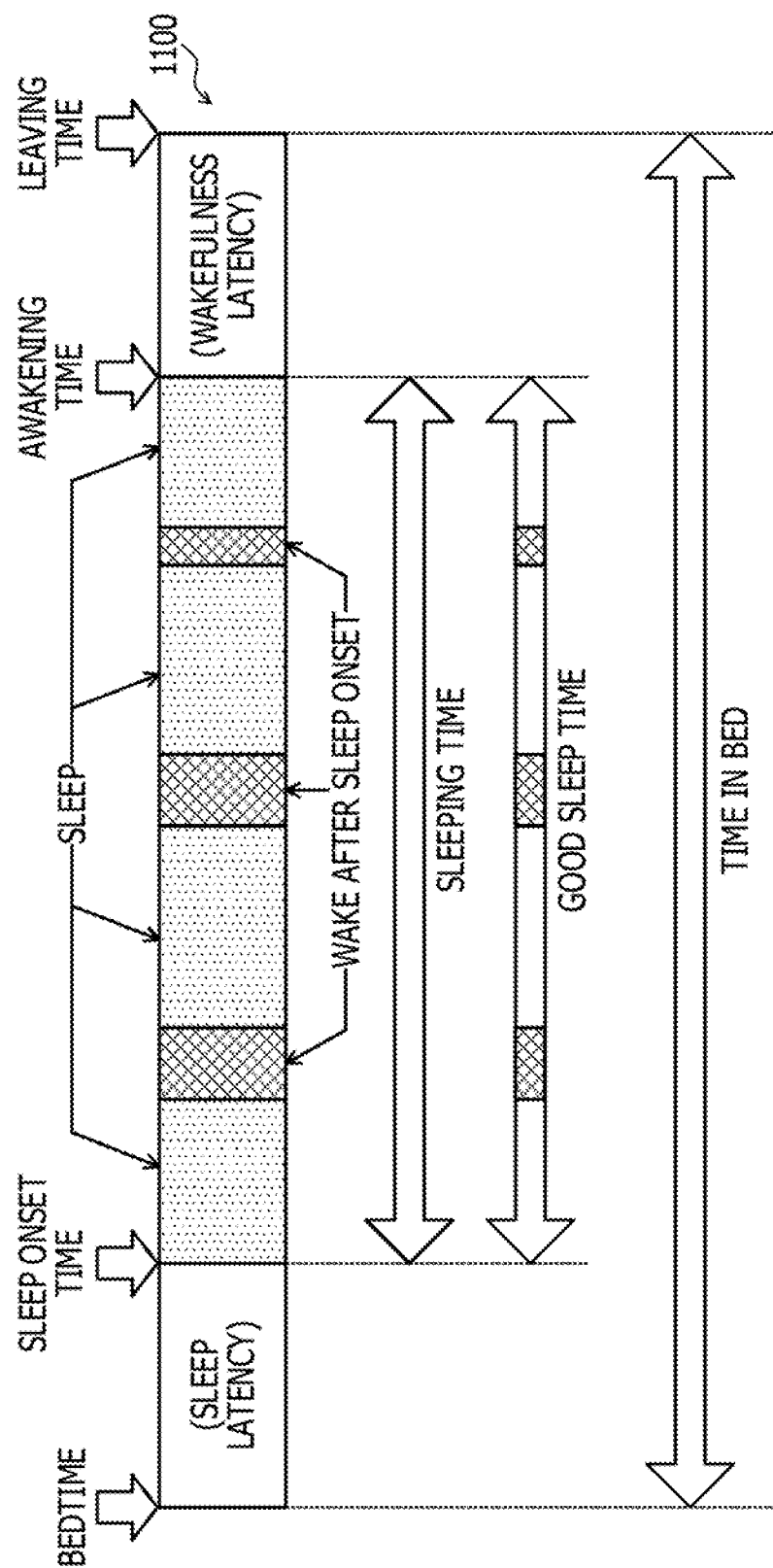
FIG. 11 is a diagram for explaining sleep efficiency.

Referring now to FIG. 11, sleep efficiency is described in detail.

FIG. 11 is a diagram for explaining sleep efficiency. In FIG. 11, a graph 1100 indicates the zone from the bedtime till the leaving time. The bedtime is the time when the subject entered the bed. The sleep onset time is the time at which the subject fell asleep. The awakening time is the time at which the subject woke up from sleep. The leaving time is the time at which the subject got out of the bed. Wake after sleep onset is a zone in which the subject temporarily awakens during sleep.

First, the determination unit 1003 calculates the good sleep time of the subject, using Expression (1) shown below. However, the good sleep time is the time obtained by subtracting the time of wake after sleep onset from the sleeping time. The sleeping time is the zone from the sleep onset time till the awakening time.

$$\text{Good sleep time} = \text{sleeping time} - \Sigma (\text{wake after sleep onset}) \quad (1)$$

The determination unit 1003 then calculates the sleep efficiency of the subject, using Expression (2) shown below. Here, the time in bed is the zone from the bedtime till the leaving time.

$$\text{Sleep efficiency (unit: \%)} = \text{good sleep time}/\text{time in bed} \times 100 \quad (2)$$

Note that the bedtime, the sleep onset time, the awakening time, the leaving time, and the wake after sleep onset are identified on the basis of data acquired from the activity meter 202, for example. The data used at this time can be designated as appropriate. For example, the data about the day before the analysis period may be used.

Here, if the sleep efficiency is about 85%, it is safe to say that the sleep state is ideal. In a case where the sleep efficiency is in the range of 91% to 100%, on the other hand, the sleeping time is not enough. In this case, it is preferable to make the pre-sleep zone longer, to fall asleep promptly after entering the bed, for example. For this reason, in a case where the sleep efficiency is in the range of 91% to 100%, the determination unit 1003 may determine the pre-sleep zone to be about 30 minutes longer than the reference length, such as one hour and 30 minutes, for example.

Further, in a case where the sleep efficiency is in the range of 0% to 79%, it is safe to say that the sleep latency from entering the bed till falling asleep is long. In this case, it is preferable to make the pre-sleep zone shorter, to fall asleep promptly after entering the bed, for example. For this reason, in a case where the sleep efficiency is in the range of 0% to 79%, the determination unit 1003 may determine the pre-sleep zone to be about 30 minutes shorter than the reference length, such as 30 minutes, for example.

Also, in a case where the sleep efficiency is in the range of 0% to 79%, the post-awakening zone may be made longer, so that the subject catches bright light after getting up and resets the circadian rhythm. For this reason, the determination unit 1003 may determine the post-awakening zone to be about 30 minutes longer than the reference length, such as one hour, for example.

Further, in a case where the awakening time of the subject is earlier than the identified sunrise time, the determination unit 1003 may determine the post-awakening zone to be about 15 minutes shorter than the reference length, such as 15 minutes, for example. Thus, the awakening time can be prevented from becoming even earlier due to bright light from a sunrise.

Returning to the description with reference to FIG. 10, the evaluation unit 1004 evaluates the suitability of the space R as a sleep environment, on the basis of the data about the space R acquired from the environment sensor 201. The data about the space R is information that indicates the temperature, the humidity, the illuminance, or the sound pressure of the space R, or any combination thereof, for example.

In a case where the data about the space R indicates the temperature of the space R, for example, the evaluation unit 1004 evaluates the suitability of the space R as a sleep environment, on the basis of the temperature of the space R. Likewise, in a case where the data about the space R indicates the humidity of the space R, the evaluation unit 1004 evaluates the suitability of the space R as a sleep environment, on the basis of the humidity of the space R. Further, in a case where the data about the space R indicates the illuminance of the space R, the evaluation unit 1004 evaluates the suitability of the space R as a sleep environment, on the basis of the illuminance of the space R. Further, in a case where the data about the space R indicates the sound pressure of the space R, the evaluation unit 1004 evaluates the suitability of the space R as a sleep environment, on the basis of the sound pressure of the space R.

Specifically, using the evaluation criteria for evaluating the suitability of the space R as a sleep environment, the evaluation unit 1004 evaluates the suitability of the space R as a sleep environment at each predetermined time intervals, on the basis of the chronological change in the data about the space R detected by the environment sensor 201, for example. The predetermined time intervals can be set as appropriate, and are set to the intervals at which the environment sensor 201 detects data (intervals of one minute in the example illustrated in FIG. 5), for example.

Note that the evaluation criteria for evaluating the suitability of the space R as a sleep environment are stored in in the various tables 600, 700, 800, and 900 illustrated in FIGS. 6 through 9, for example.

Here, an environment suitable for sleep tends to change at various points of time, such as before falling asleep, during sleep, and after waking up. For example, before falling asleep, a lower temperature is preferable for a person to quickly fall asleep, and relaxing while listening to music is also preferable. Further, even when a person is sleeping, if the bedroom is bright, the light affects the person, and the quality of sleep tends to decrease. Therefore, darkness is preferable during sleep. On the other hand, a person tends to easily wake up when it becomes gradually brighter.

For this reason, the evaluation unit 1004 may apply different evaluation criteria to each zone among the sleep zone, the pre-sleep zone, and the post-awakening zone. By doing so, the evaluation unit 1004 can evaluate the suitability of the space R as a sleep environment, taking into consideration the fact that the environment suitable for sleep varies in each zone among the sleep zone, the pre-sleep zone, and the post-awakening zone.

Furthermore, the sunrise or sunset time might come while a person is sleeping. At sunrise, the inside of a room tends to become brighter with sunlight. Therefore, if the suitability after sunrise is evaluated in the same manner as before sunrise, the evaluation result is likely to be poor. Further, after sunset, the inside of a room tends to darken because the sun has set. Therefore, if the suitability before sunset is evaluated on the basis of the same criteria as after sunset, the evaluation result is likely to be poor.

Also, at sunrise, the temperature in a room tends to become higher with sunlight. Therefore, if the suitability after sunrise is evaluated in the same manner as before sunrise, the evaluation result is likely to be poor particularly during a hot season such as summer. Further, after sunset, the temperature of a room tends to drop because the sun has set. Therefore, if the suitability before sunset is evaluated on the basis of the same criteria as after sunset, the evaluation result is likely to be poor during summer or the like.

For this reason, in a case where the sleep zone includes a time relating to a sunrise or a sunset, the evaluation unit 1004 may change suitability evaluation criteria before or after the sunrise or sunset time. By doing so, the evaluation unit 1004 can evaluate the suitability of the space R as a sleep environment, taking into consideration the environment change caused by a sunrise or a sunset in the sleep zone.

Further, in the sleep zone, the environment suitable for sleep tends to change. For example, temperature is preferably lower in the earlier zone of the sleep zone than in the later zone. For this reason, the evaluation unit 1004 may divide the sleep zone into a plurality of zones, and apply different evaluation criteria to each of the divisional zones.

In doing so, the evaluation unit 1004 may divide the sleep zone substantially equally, or may divide the sleep zone from the top by a predetermined duration (two hours, for example). Note that the number of zones into which the sleep zone is to be divided can be determined as appropriate. By doing so, the evaluation unit 1004 can evaluate the suitability of the space R as a sleep environment, taking into consideration the fact that the environment suitable for sleep changes even within the sleep zone.

For example, the sleep zone "23:00 to 7:00" is divided into a sleep zone (the earlier zone) "23:00 to 2:00", a sleep zone (the middle zone) "2:00 to 4:00", and a sleep zone (the later zone) "4:00-7:00". In this case, the evaluation unit 1004 applies evaluation criteria A to the sleep zone (the earlier zone), evaluation criteria B to the sleep zone (the middle zone), and evaluation criteria C to the sleep zone (the later zone). Further, if the sunrise time is "6:00", the evaluation unit 1004 applies the evaluation criteria C to the zone of "4:00 to 6:00", and applies evaluation criteria D to the zone of "6:00 to 7:00".

The evaluation unit 1004 may also evaluate the suitability of the space R as a sleep environment in the livelihood zone of the subject. Here, the livelihood zone is another zone different from the zone including the sleep zone, the pre-sleep zone, and the post-awakening zone. The evaluation criteria to be applied to the livelihood zone may be the same evaluation criteria as those for the sleep zone, or may be evaluation criteria only for the livelihood zone, for example.

Further, the environment suitable for sleep tends to change with seasons such as spring, summer, autumn, and winter. For example, the temperature suitable for sleep tends to be lower in winter than in summer. For this reason, the evaluation unit 1004 may change the evaluation criteria for the sleep zone, the pre-sleep zone, the post-awakening zone, or the livelihood zone, or any combination thereof, depending on the season of the analysis period.

An analysis period is a period (a date, for example) about which a sleep environment is to be analyzed. However, environments suitable for sleep tend to be similar in spring and autumn. For this reason, the seasons may be classified into three: spring/autumn, summer, and winter. In this manner, the evaluation unit 1004 can evaluate the suitability of the space R as a sleep environment, taking into consideration the fact that the environment suitable for sleep changes with seasons. In this case, the suitability of the space R as a sleep environment indicates the degree of deviation from the ideal environment for each season.

Note that the analysis period may be designated by an operation input conducted by a user using the input device 308. Alternatively, the analysis period may be identified from the period during which data about the space R has been detected by the environment sensor 201, such as the date indicated by environment sensor information, for example. The evaluation unit 1004 then determines the season to be spring if the analysis period is in the period from March to May, determines the season to be summer if the analysis period is in the period from June to August, determines the season to be autumn if the analysis period is in the period from September to November, and determines the season to be winter if the analysis period is in the period from December to February, for example.

Further, the evaluation unit 1004 may generate a comprehensive evaluation value of the suitability in the sleep zone, on the basis of the chronological change in the suitability during the sleep zone. Here, the comprehensive evaluation value is a value obtained by integrating the suitability in the sleep zone. In a case where suitability is expressed as a score, for example, the comprehensive evaluation value may be the average value of the suitability in the sleep zone. However, the comprehensive evaluation value may be rounded down, rounded up, or rounded off to the closest whole number. Alternatively, the comprehensive evaluation value may be the highest value or the lowest value of the suitability in the sleep zone.

Note that an example of evaluation of the suitability of the space R as a sleep environment will be described later with reference to FIG. 12. Also, an example of generation of a comprehensive evaluation value of the suitability of the space R as a sleep environment will be described later with reference to FIG. 13.

The display control unit 1005 performs control for displaying the evaluated suitability of the space R as a sleep environment. Specifically, the display control unit 1005 chronologically displays the suitability in the sleep zone of the subject, on the basis of the evaluated suitability for each predetermined time, for example. In doing so, the display control unit 1005 may also chronologically display the suitability in the pre-sleep zone and the post-awakening zone. The display control unit 1005 may further chronologically display the suitability in the livelihood zone.

The manner in which the chronological change in the suitability in each of the zones (the sleep zone, the pre-sleep zone, the post-awakening zone, and the livelihood zone) is to be displayed can be set as appropriate. For example, the chronological change in the suitability in each zone may be indicated by a band graph in which different colors or patterns are given in accordance with the suitability. Further, the chronological change in the suitability in each zone may be indicated by a line graph connecting the degrees of suitability in order.

More specifically, the display control unit 1005 identifies the suitability in each predetermined zone in each zone, for example. The predetermined zones can be set as appropriate, and may be zones at certain time intervals (of one hour, for example) in each zone, or may be each entire zone. The suitability in each predetermined zone is identified as the lowest suitability or the highest suitability in the predetermined zone, for example. Alternatively, the average value of the suitability in the predetermined zone may be used as the suitability in the predetermined zone. The display control unit 1005 may then display, for each zone, a band graph with different colors or patterns in accordance with the identified degrees of suitability in the respective predetermined zones.

When chronologically displaying the suitability of the space R as a sleep environment, the display control unit 1005 may also display the zone including the sleep zone, the pre-sleep zone, and the post-awakening zone of the subject, in a different manner from the other zone. The other zone is the livelihood zone of the subject, for example. Here, the manner in which the zone including the sleep zone, the pre-sleep zone, and the post-awakening zone is displayed so as to be different from the other zone can be set as appropriate.

For example, there may be a case where the chronological change in the suitability in each zone is represented by a band graph having different colors or patterns depending on the degrees of suitability. In this case, the display control unit 1005 may put shading on the band graph for the zone other than the zone including the sleep zone, the pre-sleep zone, and the post-awakening zone.

Further, there may be a case where the chronological change in the suitability in each zone is represented by a line graph connecting the degrees of suitability in order, for example. In this case, the display control unit 1005 may use a line graph of a different line type for the zone including the sleep zone, the pre-sleep zone, and the post-awakening zone, from the line type for the other zone. The display control unit 1005 may also put shading on the line graph for the other zone.

Further, when chronologically displaying the suitability of the space R as a sleep environment, the display control unit 1005 may also display the sleep zone, the pre-sleep zone, and the post-awakening zone so as to be distinguishable from one another. Specifically, the display control unit 1005 may display information (a line segment, for example) for separating the pre-sleep zone and the sleep zone, and information for separating the sleep zone and the post-awakening zone, for example.

Figure 14:
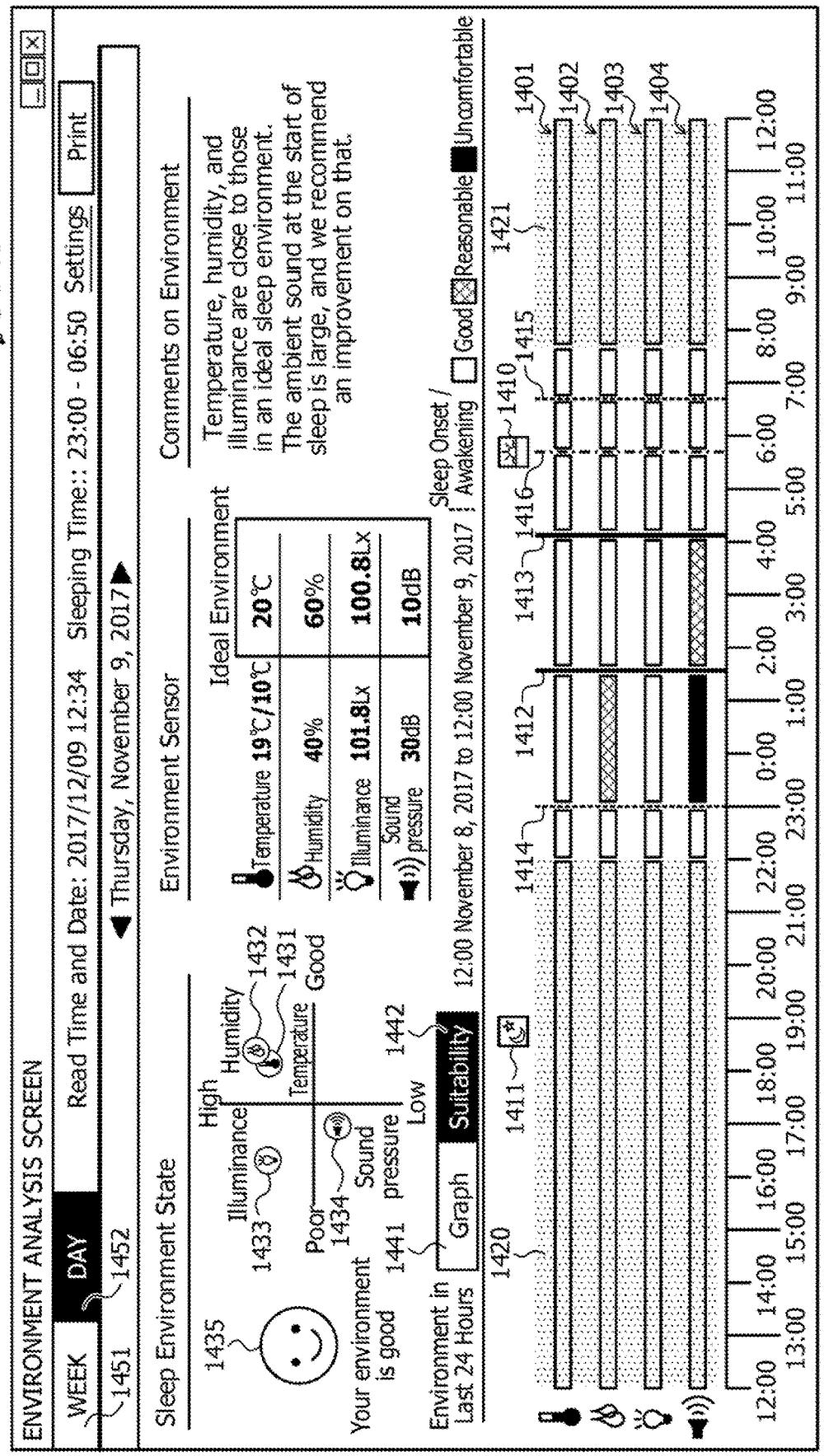
FIG. 14 is an explanatory diagram (part 1) illustrating an exemplary screen of an environment analysis screen 1400.

More specifically, the display control unit 1005 generates screen information for an environment analysis screen 1400 as illustrated in FIG. 14 described later, for example. The display control unit 1005 then performs control to cause the display 307 illustrated in FIG. 3 to display the environment analysis screen 1400, on the basis of the generated screen information.

The display control unit 1005 may also chronologically display the acquired data about the space R. The manner in which the chronological change in the data (temperature, humidity, illuminance, or sound pressure) about the space R is to be displayed can be set as appropriate. For example, the chronological change in the data about the space R may be represented by a line graph connecting the temperatures or the like of the space R, or may be displayed in the form of a table. This enable presentation of the information that is the basis of the suitability of the space R as a sleep environment.

Figure 15:
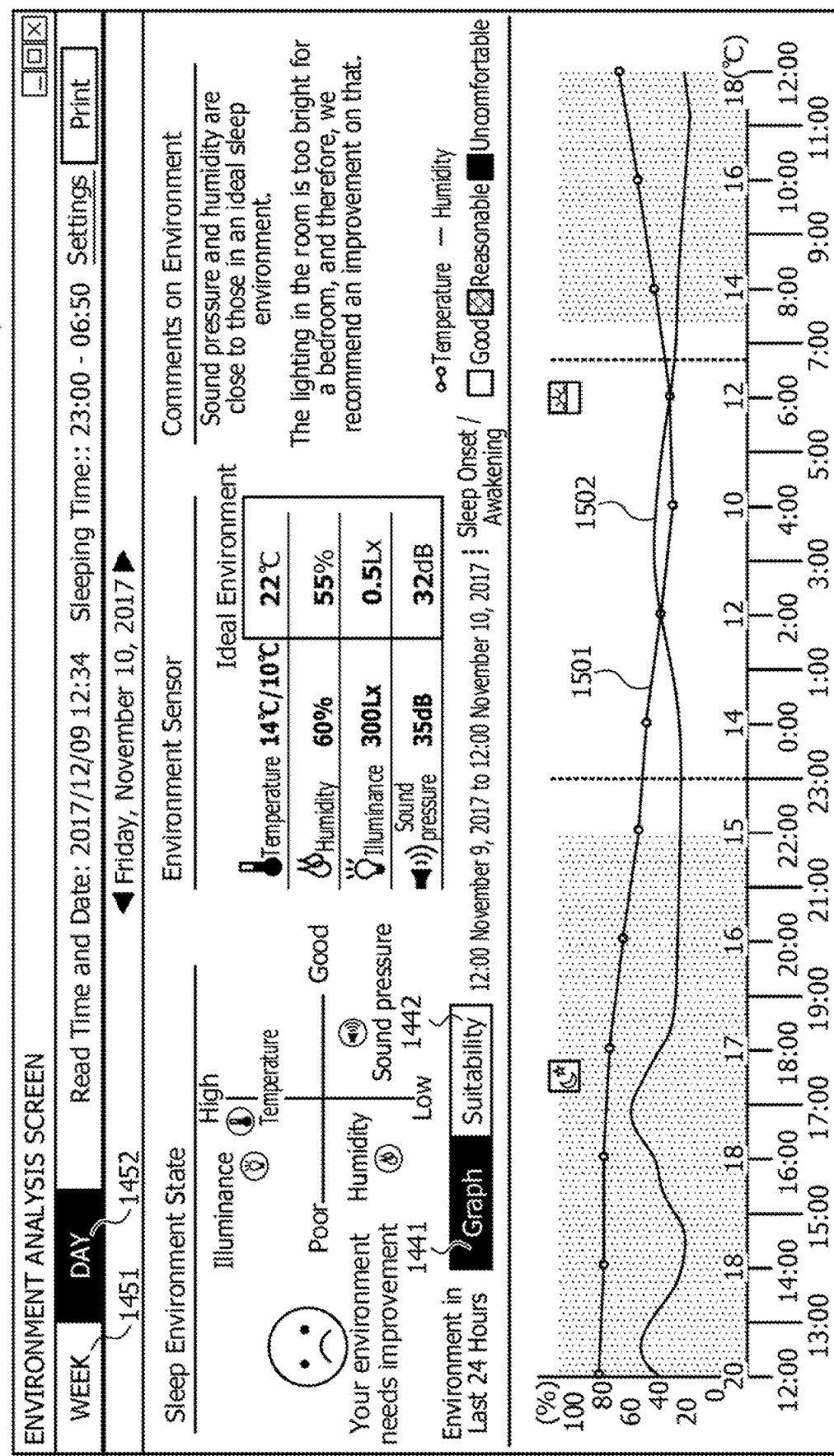
FIG. 15 is an explanatory diagram (part 2) illustrating an exemplary screen of the environment analysis screen 1400.

More specifically, the display control unit 1005 generates screen Information for the environment analysis screen 1400 as illustrated in FIG. 15 described later, for example. The display control unit 1005 then performs control to cause the display 307 to display the environment analysis screen 1400, on the basis of the generated screen information.

The display control unit 1005 also displays a generated comprehensive evaluation value for the suitability in the sleep zone. The comprehensive evaluation value may be represented by a numerical value, or may be represented by a figure, a symbol, or the like. Specifically, when chronologically displaying the suitability of the space R as a sleep environment, the display control unit 1005 may also display the comprehensive evaluation value of the suitability in the sleep zone, for example. Further, the display control unit 1005 may also chronologically display the comprehensive evaluation value of the suitability in the sleep zone of the subject on each day, for example.

Figure 16:
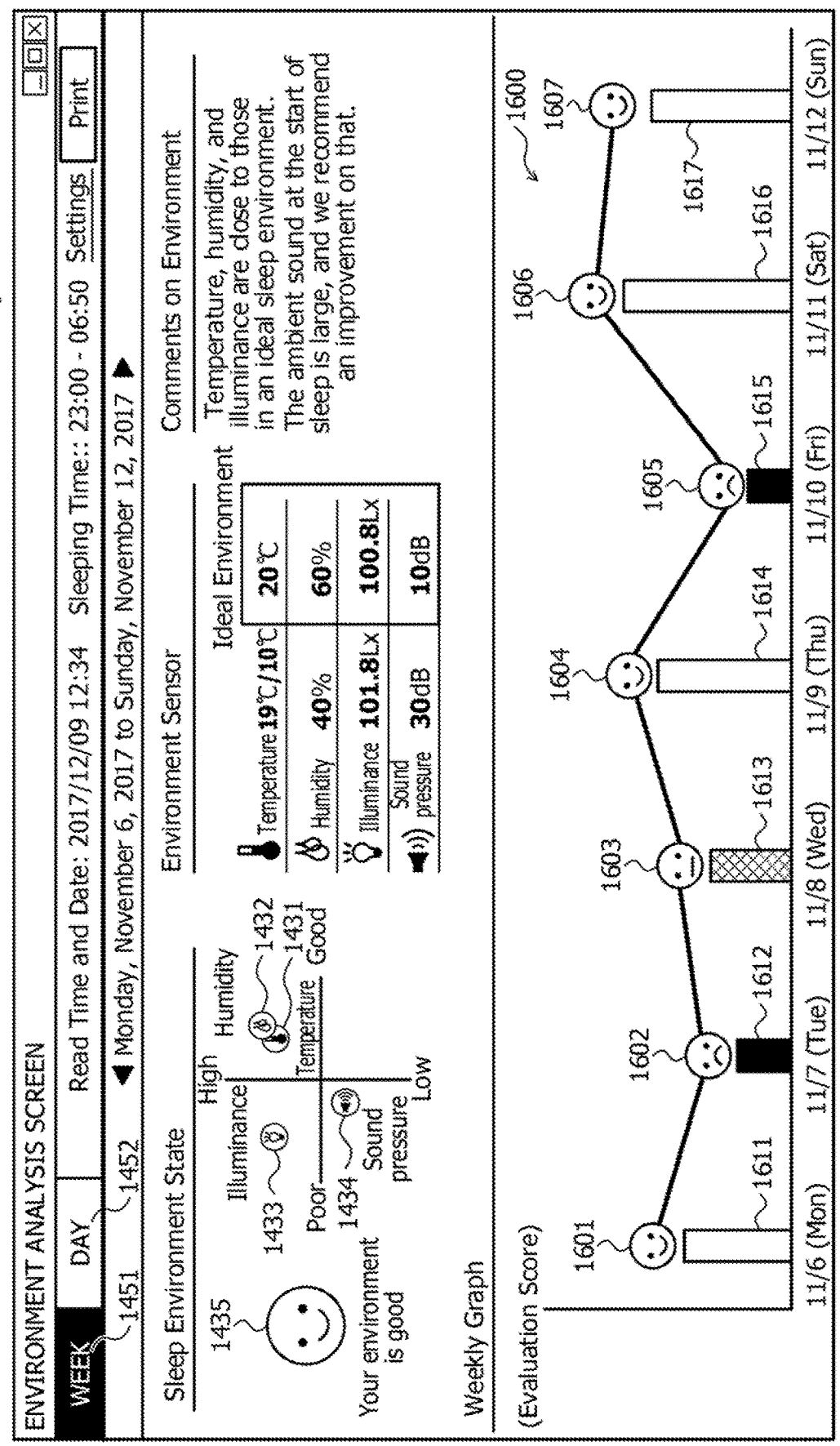
FIG. 16 is an explanatory diagram (part 3) illustrating an exemplary screen of the environment analysis screen 1400.

More specifically, the display control unit 1005 generates screen information for the environment analysis screen 1400 as illustrated in FIG. 16 described later, for example. The display control unit 1005 then performs control to cause the display 307 to display the environment analysis screen 1400, on the basis of the generated screen information.

Note that some or all of the functional units of the display device 101 may be formed with another computer different from the display device 101, such as a server connected to the display device 101, for example.

(Exemplary Evaluation of Suitability of Space R as Sleep Environment)

Next, examples of evaluation in cases where the suitability of the space R as a sleep environment is evaluated with the use of the various tables 600, 700, 800, and 900 illustrated in FIGS. 6 through 9 are described.

Here, the sleep zone of the subject is "23:00 to 8:00", the pre-sleep zone is "22:00 to 23:00", and the post-awakening zone is "8:00 to 8:30". Further, the sunrise time is "7:00". Furthermore, the sleep zone is divided into a sleep zone (the earlier zone) "23:00 to 2:00", a sleep zone (the middle zone) "2:00 to 5:00", and a sleep zone (the later zone) "5:00 to 8:00".

<First Environment Sensor Information>

First environment sensor information is first described as an example of the data about the space R from the environment sensor 201. The first environment sensor information indicates an environment sensor ID "001", a date "2017/11/11 22:10", a temperature "25 [° C.]", a humidity "39 [%]", an illuminance "25 [Lx]", and a sound pressure "40 [dB]". In the description below, examples of evaluation of the suitability of the space R as a sleep environment will be described regarding the temperature, the humidity, the illuminance, and the sound pressure of the space R.

Temperature of the Space R

Since the date "2017/11/11 22:10" in the first environment sensor information is within the period from September to November, the evaluation unit 1004 determines the season to be "autumn". Here, the date "2017/11/11 22:10" falls within the pre-sleep zone. In this case, the evaluation criteria relating to the temperature in the sleep zone (the earlier zone) are used as the evaluation criteria relating to the temperature in the pre-sleep zone.

In this case, the evaluation unit 1004 uses the evaluation criteria for the earlier zone in the temperature threshold table 610, to evaluate the suitability of the space R as a sleep environment on the basis of the temperature "25 [° C.]" indicated by the first environment sensor information. Here, the suitability of the temperature of the space R gains a score "2". The score "2" corresponds to "reasonable" in a case where suitability is expressed at the three levels: comfortable, reasonable, and uncomfortable, for example.

Note that, in the examples of the various tables 600, 700, 800, and 900, in a case where the evaluation criteria for a plurality of scores are simultaneously satisfied, the evaluation result is the highest in the plurality of scores that satisfy the evaluation criteria. For example, in a case where the evaluation criteria for the score "3" and the score "2" are both satisfied, the evaluation result is the score "3".

Humidity of the Space R

Since the date "2017/11/11 22:10" in the first environment sensor information is within the period from September to November, the evaluation unit 1004 determines the season to be "autumn". Here, the date "2017/11/11 22:10" falls within the pre-sleep zone. In this case, the evaluation criteria relating to the humidity in the sleep zone (the earlier zone) are used as the evaluation criteria relating to the humidity in the pre-sleep zone.

In this case, the evaluation unit 1004 uses the evaluation criteria for the earlier zone in the humidity threshold table 700, to evaluate the suitability of the space R as a sleep environment on the basis of the humidity "39 [%]" indicated by the first environment sensor information. Here, the suitability of the humidity of the space R gains the score "1". The score "1" corresponds to "uncomfortable" in a case where suitability is expressed at the three levels: comfortable, reasonable, and uncomfortable, for example.

Illuminance of the Space R

Here, the date "2017/11/11 22:10" in the first environment sensor information falls within the pre-sleep zone. In this case, the evaluation unit 1004 uses the evaluation criteria for the pre-sleep zone in the illuminance threshold table 800, to evaluate the suitability of the space R as a sleep environment on the basis of the illuminance "25 [Lx]" indicated by the first environment sensor information. Here, the suitability of the humidity of the space R gains the score "3". The score "3" corresponds to "comfortable" in a case where suitability is expressed at the three levels: comfortable, reasonable, and uncomfortable, for example.

Sound Pressure of the Space R

Here, the date "2017/11/11 22:10" in the first environment sensor information falls within the pre-sleep zone. In this case, the evaluation unit 1004 uses the evaluation criteria for the pre-sleep zone in the sound pressure threshold table 900, to evaluate the suitability of the space R as a sleep environment on the basis of the sound pressure "40 [dB]" indicated by the first environment sensor information. Here, the suitability of the sound pressure of the space R gains the score "3".

Note that the results of evaluation of temperature, humidity, illuminance, and sound pressure are stored into an evaluation result table 1200 as illustrated in FIG. 12, for example. The evaluation result table 1200 is formed with storage devices such as the memory 302, the disk 304, and the like, for example.

FIG. 12 is an explanatory diagram illustrating an example of the contents stored in the evaluation result table 1200. In FIG. 12, the evaluation result table 1200 has fields of environment sensor ID, date, time, temperature, humidity, illuminance, and sound pressure, and stores records of evaluation results (evaluation results 1200-1 through 1200-4, for example) by setting information in the respective fields.

For example, the evaluation result 1200-1 indicates the suitability of the space R as a sleep environment based on the first environment sensor information described above. Specifically, the evaluation result 1200-1 indicates temperature "2", humidity "1", Illuminance "3", and sound pressure "3" as the suitability at the time and date "2017/11/11 22:10" based on the data from the environment sensor 201 of the environment sensor ID "001".

<Second Environment Sensor Information>

Next, second environment sensor information is described as an example of the data about the space R from the environment sensor 201. The second environment sensor information indicates an environment sensor ID "001", a date "2017/11/12 2:10", a temperature "22 [° C.]", a humidity "39 [%]", an illuminance "5 [Lx]", and a sound pressure "30 [dB]".

Temperature of the Space R

Since the date "2017/11/12 2:10" in the first environment sensor information is within the period from September to November, the evaluation unit 1004 determines the season to be "autumn". Here, the date "2017/11/12 2:10" falls within the sleep zone (the middle zone).

In this case, the evaluation unit 1004 uses the evaluation criteria for the middle zone in the temperature threshold table 610, to evaluate the suitability of the space R as a sleep environment on the basis of the temperature "22 [° C.]" indicated by the second environment sensor information. Here, the suitability of the temperature of the space R gains the score "3".

Humidity of the Space R

Since the date "2017/11/12 2:10" in the second environment sensor information is within the period from September to November, the evaluation unit 1004 determines the season to be "autumn". Here, the date "2017/11/12 2:10" falls within the sleep zone (the middle zone).

In this case, the evaluation unit 1004 uses the evaluation criteria for the middle zone in the humidity threshold table 700, to evaluate the suitability of the space R as a sleep environment on the basis of the humidity "39 [%]" Indicated by the second environment sensor information. Here, the suitability of the humidity of the space R gains the score "1".

Illuminance of the Space R

Here, the date "2017/11/12 2:10" in the second environment sensor information falls within the sleep zone. In this case, the evaluation unit 1004 uses the evaluation criteria for the sleep zone in the illuminance threshold table 800, to evaluate the suitability of the space R as a sleep environment on the basis of the illuminance "5 [Lx]" indicated by the second environment sensor information. Here, the suitability of the humidity of the space R gains the score "2".

Sound Pressure of the Space R

Here, the date "2017/11/12 2:10" in the second environment sensor information falls within the sleep zone. In this case, the evaluation unit 1004 uses the evaluation criteria for the sleep zone in the sound pressure threshold table 900, to evaluate the suitability of the space R as a sleep environment on the basis of the sound pressure "30 [dB]" indicated by the second environment sensor information. Here, the suitability of the sound pressure of the space R gains the score "3".

In FIG. 12, the evaluation result 1200-2 indicates the suitability of the space R as a sleep environment based on the second environment sensor information described above. Specifically, the evaluation result 1200-2 indicates temperature "3", humidity "1", illuminance "2", and sound pressure "3" as the suitability at the time and date "2017/11/12 2:10" based on the data from the environment sensor 201 of the environment sensor ID "001".

<Third Environment Sensor Information>

Next, third environment sensor information is described as an example of the data about the space R from the environment sensor 201. The third environment sensor information indicates an environment sensor ID "001", a date "2017/11/12 7:10", a temperature "23 [° C.]", a humidity "43 [%]", an illuminance "8 [Lx]", and a sound pressure "40 [dB]".

Temperature of the Space R

Since the date "2017/11/12 7:10" in the third environment sensor information is within the period from September to November, the evaluation unit 1004 determines the season to be "autumn". Here, the date "2017/11/12 7:10" falls within the sleep zone (the later zone).

In this case, the evaluation unit 1004 uses the evaluation criteria for the later zone in the temperature threshold table 610, to evaluate the suitability of the space R as a sleep environment on the basis of the temperature "23 [° C.]" indicated by the third environment sensor information. Here, the suitability of the temperature of the space R gains the score "3".

Humidity of the Space R

Since the date "2017/11/12 7:10" in the third environment sensor information is within the period from September to November, the evaluation unit 1004 determines the season to be "autumn". Here, the date "2017/11/12 7:10" falls within the sleep zone (the later zone).

In this case, the evaluation unit 1004 uses the evaluation criteria for the later zone in the humidity threshold table 700, to evaluate the suitability of the space R as a sleep environment on the basis of the humidity "43 [%]" indicated by the third environment sensor information. Here, the suitability of the humidity of the space R gains the score "2".

Illuminance of the Space R

Here, the date "2017/11/12 7:10" in the third environment sensor information falls within the sleep zone, and is later than the sunrise time. In this case, the evaluation unit 1004 uses the evaluation criteria for the sleep zone (including a sunrise) in the illuminance threshold table 800, to evaluate the suitability of the space R as a sleep environment on the basis of the illuminance "8 [Lx]" indicated by the third environment sensor information. Here, the suitability of the humidity of the space R gains the score "3".

Sound Pressure of the Space R

Here, the date "2017/11/12 7:10" in the third environment sensor information falls within the sleep zone. In this case, the evaluation unit 1004 uses the evaluation criteria for the sleep zone in the sound pressure threshold table 900, to evaluate the suitability of the space R as a sleep environment on the basis of the sound pressure "40 [dB]" indicated by the third environment sensor information. Here, the suitability of the sound pressure of the space R gains the score "2".

In FIG. 12, the evaluation result 1200-3 indicates the suitability of the space R as a sleep environment based on the third environment sensor information described above. Specifically, the evaluation result 1200-3 indicates temperature "3", humidity "2", illuminance "3", and sound pressure "2" as the suitability at the time and date "2017/11/12 7:10" based on the data from the environment sensor 201 of the environment sensor ID "001".

<Fourth Environment Sensor Information>

Next, fourth environment sensor information is described as an example of the data about the space R from the environment sensor 201. The fourth environment sensor information indicates an environment sensor ID "001", a date "2017/11/12 8:10", a temperature "24 [° C.]", a humidity "43 [%]", an illuminance "2700 [Lx]", and a sound pressure "40 [dB]".

Temperature of the Space R

Since the date "2017/11/12 8:10" in the fourth environment sensor information is within the period from September to November, the evaluation unit 1004 determines the season to be "autumn". Here, the date "2017/11/12 8:10" falls within the post-awakening zone. In this case, the evaluation criteria relating to the temperature in the sleep zone (the later zone) are used as the evaluation criteria relating to the temperature in the post-awakening zone.

In this case, the evaluation unit 1004 uses the evaluation criteria for the later zone in the temperature threshold table 610, to evaluate the suitability of the space R as a sleep environment on the basis of the temperature "24 [° C.]" indicated by the fourth environment sensor information. Here, the suitability of the temperature of the space R gains the score "3".

Humidity of the Space R

Since the date "2017/11/12 8:10" in the third environment sensor information is within the period from September to November, the evaluation unit 1004 determines the season to be "autumn". Here, the date "2017/11/12 8:10" falls within the post-awakening zone. In this case, the evaluation criteria relating to the humidity in the sleep zone (the later zone) are used as the evaluation criteria relating to the humidity in the post-awakening zone.

In this case, the evaluation unit 1004 uses the evaluation criteria for the later zone in the humidity threshold table 700, to evaluate the suitability of the space R as a sleep environment on the basis of the humidity "43 [%]" indicated by the fourth environment sensor information. Here, the suitability of the humidity of the space R gains the score "2".

Illuminance of the Space R

Here, the date "2017/11/12 8:10" in the fourth environment sensor information falls within the post-awakening zone. In this case, the evaluation unit 1004 uses the evaluation criteria for the post-awakening zone in the illuminance threshold table 800, to evaluate the suitability of the space R as a sleep environment on the basis of the illuminance "2700 [Lx]" indicated by the fourth environment sensor information. Here, the suitability of the humidity of the space R gains the score "3".

Sound Pressure of the Space R

Here, the date "2017/11/12 8:10" in the third environment sensor information falls within the post-awakening zone. In this case, the evaluation unit 1004 uses the evaluation criteria for the post-awakening zone in the sound pressure threshold table 900, to evaluate the suitability of the space R as a sleep environment on the basis of the sound pressure "40 [dB]" indicated by the fourth environment sensor information. Here, the suitability of the sound pressure of the space R gains the score "3".

In FIG. 12, the evaluation result 1200-4 indicates the suitability of the space R as a sleep environment based on the fourth environment sensor information described above. Specifically, the evaluation result 1200-4 indicates temperature "3", humidity "2", Illuminance "3", and sound pressure "3" as the suitability at the time and date "2017/11/12 8:10" based on the data from the environment sensor 201 of the environment sensor ID "001".

The evaluation unit 1004 also generates a comprehensive evaluation value of the suitability in the sleep zone, by referring to the evaluation result table 1200, for example. Specifically, the evaluation unit 1004 acquires, from the evaluation result table 1200, an evaluation result whose time falls within the sleep zone "23:00 to 8:00", for example.

The evaluation unit 1004 then calculates the average values of scores (suitability) about temperature, humidity, illuminance, and sound pressure, on the basis of the acquired evaluation result. The evaluation unit 1004 then sets the respective results calculated for temperature, humidity, illuminance, and sound pressure as the respective comprehensive evaluation values of temperature, humidity, illuminance, and sound pressure. However, the results are rounded off to the closest whole numbers, for example.

The evaluation unit 1004 may also calculate the average value of the respective comprehensive evaluation values of temperature, humidity, illuminance, and sound pressure. The evaluation unit 1004 may then set the calculation result as the comprehensive evaluation value of the suitability in the sleep zone. The comprehensive evaluation value is the value obtained by integrating the degrees of suitability in the sleep zone of the subject.

The generated comprehensive evaluation value is stored into a comprehensive evaluation table 1300 illustrated in FIG. 13, for example. The comprehensive evaluation table 1300 is formed with storage devices such as the memory 302, the disk 304, and the like, for example.

FIG. 13 is an explanatory diagram illustrating an example of the contents stored in the comprehensive evaluation table 1300. In FIG. 13, the comprehensive evaluation table 1300 has fields of environment sensor ID, date, temperature, humidity, illuminance, and sound pressure, and stores records of comprehensive evaluation information (comprehensive evaluation information 1300-1 and 1300-2, for example) by setting information in the respective fields.

Here, an environment sensor ID is the identifier that uniquely identifies the environment sensor 201. The date is the date indicating an analysis period. However, the analysis period is the date of a day including a sleep onset time. The temperature is the comprehensive evaluation value of the temperature of the space R. The humidity is the comprehensive evaluation value of the humidity of the space R. The illuminance is the comprehensive evaluation value of the illuminance of the space R.

The sound pressure is the comprehensive evaluation value of the sound pressure of the space R. The overall value is the comprehensive evaluation value obtained by integrating the comprehensive evaluation values of the temperature, the humidity, the Illuminance, and the sound pressure of the space R. Here, the overall value is the average value of the respective comprehensive evaluation values of the temperature, the humidity, the illuminance, and the sound pressure of the space R (but is rounded off to the closest whole number).

For example, the comprehensive evaluation information 1300-1 indicates the respective comprehensive evaluation values "2, 2, 3, 3, 3" of the temperature, the humidity, the illuminance, the sound pressure, and the overall value of the space R in which the environment sensor 201 of the environment sensor ID "001" is installed, of the date "2017/11/11".

(Exemplary Screens of Environment Analysis Screen 1400)

Next, exemplary screens of the environment analysis screen 1400 to be displayed on the display 307 are described with reference to FIGS. 14 through 16. The screen information for the environment analysis screen 1400 illustrated in FIG. 14 is generated on the basis of the contents stored in the evaluation result table 1200 illustrated in FIG. 12, for example.

FIGS. 14 through 16 are explanatory diagrams illustrating an exemplary screen of the environment analysis screen 1400. In FIG. 14, the environment analysis screen 1400 is an example of an operation screen that chronologically displays the suitability of the space R as a sleep environment in which the subject sleeps. Here, graphs 1401 through 1404 are band graphs each indicating a chronological change in the suitability of the space R as a sleep environment from 12:00 on Nov. 8, 2017 till 12:00 on Nov. 9, 2017.

Specifically, the graph 1401 indicates a chronological change in suitability relating to the temperature of the space R. The graph 1402 indicates a chronological change in suitability relating to the humidity of the space R. The graph 1403 indicates a chronological change in suitability relating to the Illuminance of the space R. The graph 1404 indicates a chronological change in suitability relating to the sound pressure of the space R.

In each of the graphs 1401 through 1404, different patterns are given in accordance with the degrees of suitability (comfortable, reasonable, and uncomfortable) in the respective zones (the sleep zone, the pre-sleep zone, the post-awakening zone, and the livelihood zone). The degrees of suitability in the respective zones are the highest degrees of suitability in the respective zones. However, the sleep zone is divided into the sleep zone (the earlier zone), the sleep zone (the middle zone), and the sleep zone (the later zone). Further, in a case where the sleep zone includes the sunrise or sunset time, the sleep zone is divided into zones that are before and after that time.

A mark 1410 is the indication of the sunrise. A mark 1411 is the indication of the sunset. A solid line 1412 is the indication that separates the sleep zone (the earlier zone) and the sleep zone (the middle zone). A solid line 1413 is the indication that separates the sleep zone (the middle zone) and the sleep zone (the later zone). A dotted line 1414 is the indication that separates the pre-sleep zone and the sleep zone (the earlier zone). A dotted line 1415 is the indication that separates the sleep zone (the later zone) and the post-awakening zone. A dot-and-dash line 1416 is the indication of the sunrise time.

Further, in each of the graphs 1401 through 1404, the zones (the livelihood zone) other than the zone including the sleep zone, the pre-sleep zone, and the post-awakening zone are shaded (portions 1420 and 1421 in FIG. 14).

Furthermore, marks 1431 through 1434 under the sleep environment state indicate the comprehensive evaluation values of the degrees of suitability of the sound pressure, the humidity, the illuminance, and the sound pressure of the space R in the sleep zone. The marks 1431 through 1434 each indicate whether the comprehensive evaluation value is good or bad, depending on whether the mark is located on the right side or left side. The marks 1431 through 1434 each also indicate whether the average value of the temperature, the humidity, the illuminance, or the sound pressure in the sleep zone is higher or lower than that in an ideal environment, depending on whether the mark is located on the upper side or the lower side. Further, a mark 1435 indicates the overall comprehensive evaluation value obtained by integrating the respective comprehensive evaluation values of temperature, humidity, illuminance, and sound pressure of the space R in the sleep zone.

Meanwhile, the respective values under the environment sensor indicate the highest temperature/lowest temperature, the highest humidity, the highest illuminance, and the highest sound pressure in the sleep zone. Further, the ideal environment indicates the ideal temperature, humidity, illuminance, and sound pressure in a sleep zone. Comments on the environment are comments on the sleep environment on the basis of the degrees of suitability in the respective zones (the sleep zone, the pre-sleep zone, the post-awakening zone, and the livelihood zone).

According to the graphs 1401 through 1404, the user (a store staff member, for example) can recognize the chronological change in the suitability of the space R as a sleep environment in which the subject sleeps. In this case, because of the shaded display (the portions 1420 and 1421 in FIG. 14), the user can easily access the suitability of the space R as a sleep environment, not only in the sleep zone but also in the previous and next zones (the pre-sleep zone and the post-awakening zone) that affect sleep.

The user can also easily distinguish the pre-sleep zone and the post-awakening zone with the dotted lines 1414 and 1415. Further, the user can easily distinguish the earlier zone, the middle zone and the later zone in the sleep zone with the solid lines 1412 and 1413. The user can also easily recognize the sunrise time with the dot-and-dash line 1416.

Because of this, the store staff can accurately assess the suitability of the space R as a sleep environment in the respective zones, and provide the subject (customer) with appropriate advice for increasing the quality of sleep. The store staff can also recognize the respective degrees of suitability of temperature, humidity, illuminance, and sound pressure, and thus, is capable of giving more specific advice about the sleep environment.

Further, with the marks 1431 through 1434 under the sleep environment state, the user can intuitively determine whether the respective comprehensive evaluation values of the degrees of suitability of the sound pressure, the humidity, the illuminance, and the sound pressure of the space R in the sleep zone are good or bad. Further, it is possible to intuitively understand how to improve the temperature, the humidity, the illuminance, and the sound pressure in the entire sleep zone, depending on whether the marks 1431 through 1434 are located on the upper side or the lower side. Furthermore, with the mark 1435, the user can intuitively determine whether the comprehensive evaluation value (overall value) in the sleep zone is good or bad.

When a tab 1442 on the environment analysis screen 1400 illustrated in FIG. 14 is selected through an operation input conducted by the user using the input device 308, the contents of display on the environment analysis screen 1400 can be switched to the display contents illustrated in FIG. 15, for example. In the example illustrated in FIG. 15, however, the environment analysis screen 1400 on a different day from the example in FIG. 14 is described.

On the environment analysis screen 1400 illustrated in FIG. 15, a graph 1501 is a line graph indicating the chronological change in the temperature in the space R in which the subject sleeps. Further, a graph 1502 is a line graph indicating the chronological change in the humidity in the space R.

With the graph 1501, the user can check the chronological change in the temperature in the space R, which is the information to be the basis of the suitability relating to the temperature of the space R. Also, with the graph 1502, the user can check the chronological change in the humidity in the space R, which is the information to be the basis of the suitability relating to the humidity of the space R.

Note that, when a tab 1441 on the environment analysis screen 1400 illustrated in FIG. 15 is selected through an operation input conducted by the user, the contents of display on the environment analysis screen 1400 can be switched to the display contents illustrated in FIG. 14, for example.

Further, when a tab 1451 on the environment analysis screen 1400 illustrated in FIG. 14 is selected through an operation input conducted by the user, the contents of display on the environment analysis screen 1400 can be switched to the display contents illustrated in FIG. 16, for example. The screen information for the environment analysis screen 1400 illustrated in FIG. 16 is generated on the basis of the contents stored in the comprehensive evaluation table 1300 illustrated in FIG. 13, for example.

On the environment analysis screen 1400 illustrated in FIG. 16, a graph 1600 indicates the chronological change in the comprehensive evaluation value (the overall value) of the suitability in the sleep zone. Marks 1601 through 1607 each indicate the comprehensive evaluation value (the overall value) of each corresponding day. Bar graphs 1611 through 1617 corresponding to the respective marks 1601 through 1607 each indicate the magnitude of the comprehensive evaluation value (the overall value) of each corresponding day, which is the magnitude of the value before rounding, for example.

With the graph 1600, the user can recognize the chronological change in the comprehensive evaluation value (the overall value) of the suitability in the sleep zone on each day from Monday, November 6 to Sunday, November 12. Also, with the graph 1600, the comprehensive evaluation values (overall values) can be compared with one another among the days of the week. Thus, it is possible to intuitively determine on which day the comprehensive evaluation value (the overall value) is good or bad.

Note that, when a tab 1452 on the environment analysis screen 1400 illustrated in FIG. 16 is selected through an operation input conducted by the user, the contents of display on the environment analysis screen 1400 can be switched to the display contents illustrated in FIG. 14, for example.

(Procedures in Display Control Process in Display Device 101)

Next, the procedures in a display control process in the display device 101 are described. In an example case to be described herein, the sunrise time between the sunrise and sunset times is taken into consideration in evaluating the suitability of the space R as a sleep environment in which the subject sleeps.

Figure 17:
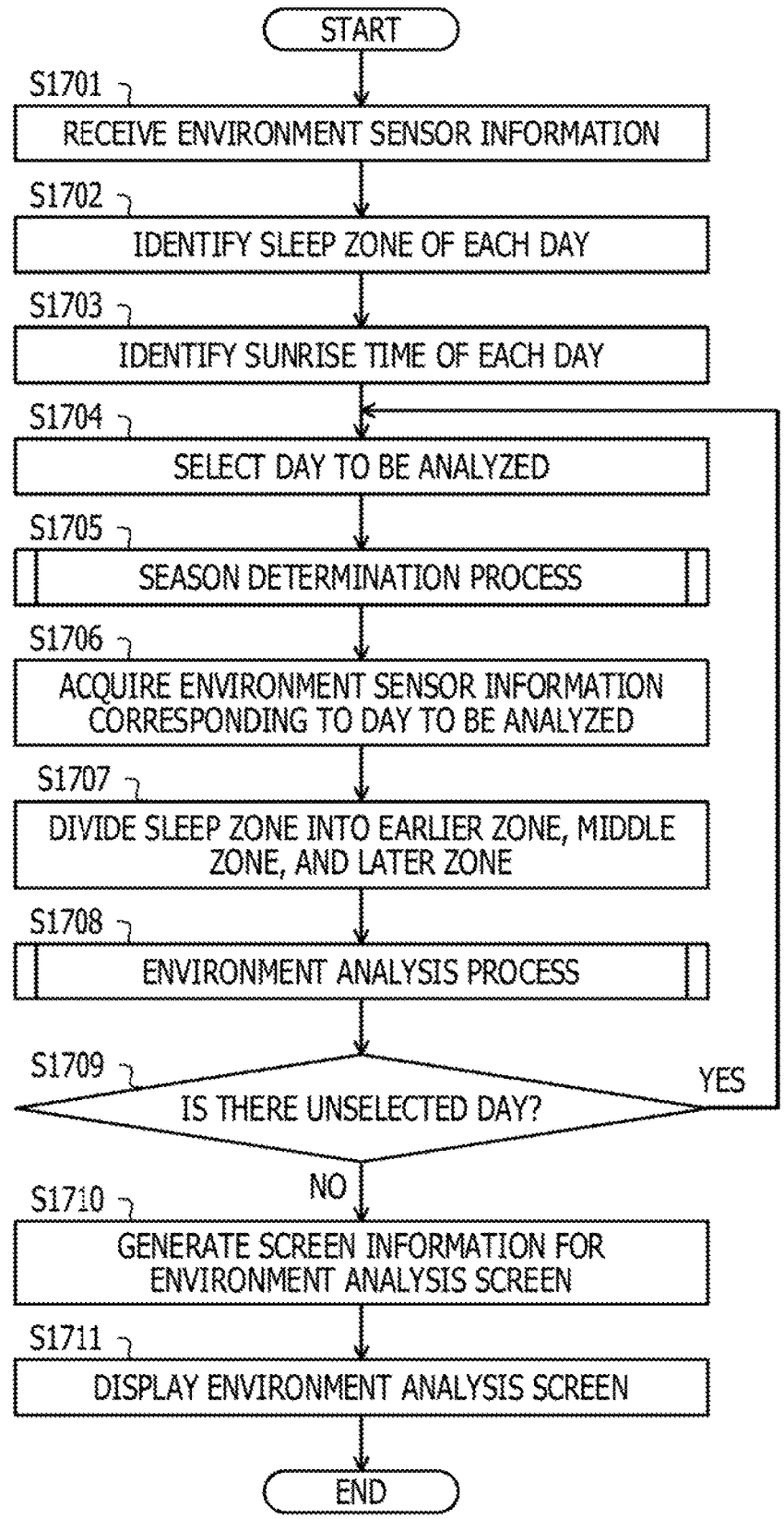
FIG. 17 is a flowchart illustrating an example of the procedures in a display control process to be performed by the display device 101.

FIG. 17 is a flowchart illustrating an example of the procedures in a display control process to be performed by the display device 101. In the flowchart in FIG. 17, the display device 101 first receives environment sensor information from the environment sensor 201 (step S1701). The received environment sensor information is stored into the environment sensor information DB 500.

The display device 101 then identifies the sleep zone of the subject for each day in the analysis target period (step S1702). The analysis target period is the period during which the sleep environment of the space R in which the subject sleeps is analyzed. The analysis target period is designated through an operation input conducted by the user using the input device 308, for example. The sleep zone of the subject on each day may be designated through an operation input conducted by the user, or may be identified in the display device 101, for example. Note that the procedures in the process of identifying the sleep zone will be described later with reference to FIG. 36.

The display device 101 then identifies the sunrise time of each day in the analysis target period (step S1703). The sunrise time may be designated through an operation input conducted by the user, or may be calculated in the display device 101, for example. Note that the procedures in the process of calculating the sunrise time will be described later with reference to FIG. 37.

The display device 101 next selects an unselected day that has not been selected from the analysis target period, as the day to be analyzed (step S1704). The display device 101 then performs a season determination process to determine the season corresponding to the day to be analyzed (step S1705). Note that the specific procedures in the season determination process will be described later with reference to FIG. 18.

The display device 101 then acquires, from the environment sensor information DB 500, the environment sensor information corresponding to the day to be analyzed (step S1706). The environment sensor information corresponding to the day to be analyzed is environment sensor information of 24 hours including at least the environment sensor information of the pre-sleep zone, the sleep zone, and the post-awakening zone, for example.

The display device 101 next divides the sleep zone of the day to be analyzed into a sleep zone (the earlier zone), a sleep zone (the middle zone), and a sleep zone (the later zone) (step S1707). The display device 101 then performs an environment analysis process with respect to the space R (step S1708). Note that the specific procedures in the environment analysis process will be described later with reference to FIGS. 19 and 20.

The display device 101 next determines whether there is an unselected day that has not been selected from the analysis target period (step S1709). Here, if there is an unselected day (step S1709: Yes), the display device 101 returns to step S1704. If there are no unselected days (step S1709: No), the display device 101 refers to the evaluation result table 1200 and the comprehensive evaluation table 1300, to generate screen Information for the environment analysis screen 1400 (step S1710).

The display device 101 then displays the environment analysis screen 1400 on the display 307 on the basis of the generated screen information (step S1711), and ends the series of processes according to this flowchart. Thus, the suitability of the space R as a sleep environment in which the subject sleeps can be evaluated, and be displayed in chronological order.

Figure 18:
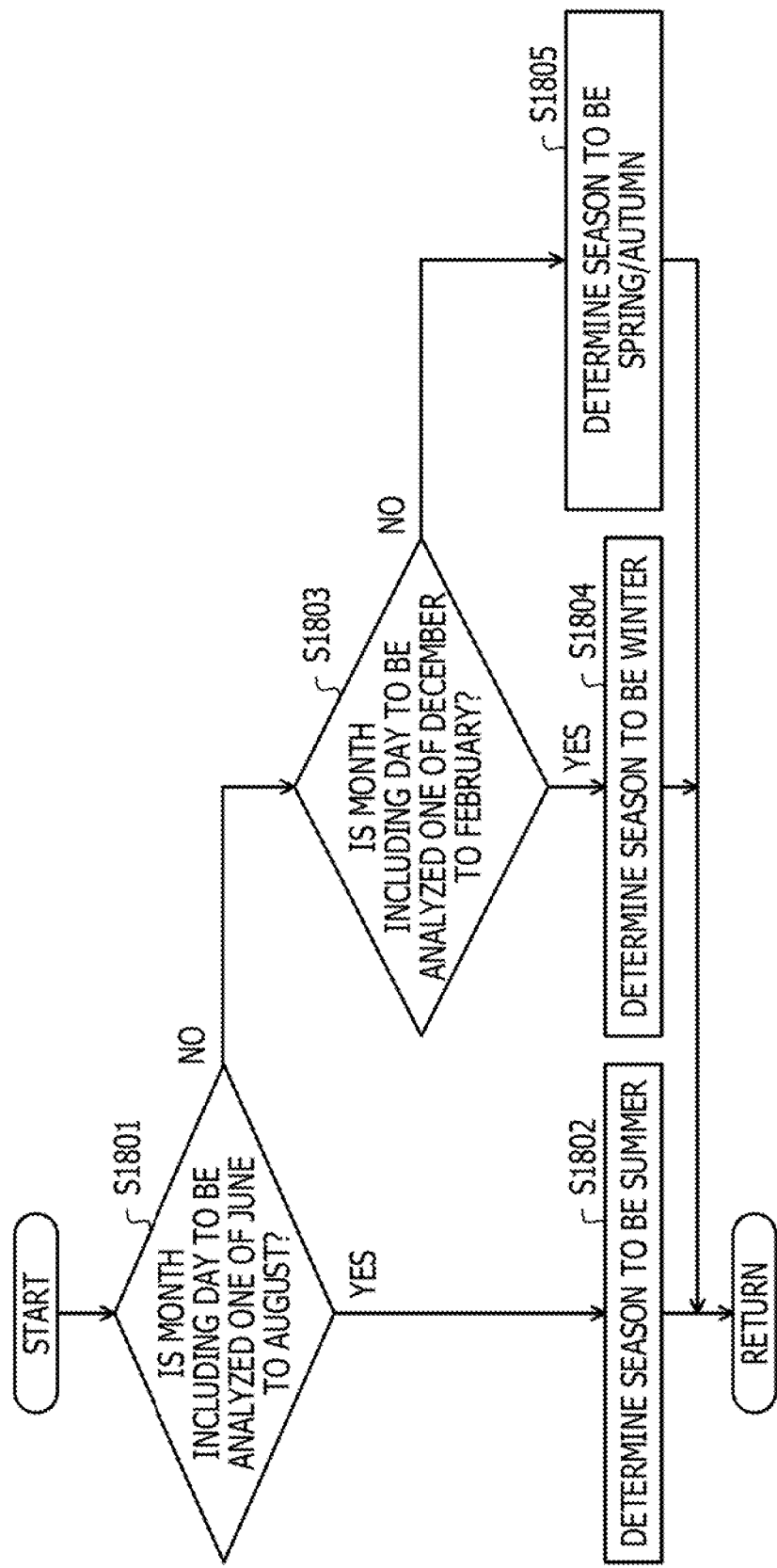
FIG. 18 is a flowchart illustrating an example of specific procedures in a season determination process.

Referring now to FIG. 18, the specific procedures in the season determination process in step S1705 are described.

FIG. 18 is a flowchart illustrating an example of the specific procedures in the season determination process. In the flowchart in FIG. 18, the display device 101 first determines whether the month including the day to be analyzed is one of June to August (step S1801). Here, if the month is one of June to August (step S1801: Yes), the display device 101 determines that the season corresponding to the day to be analyzed is summer (step S1802).

If the month is not any of June to August (step S1801: No), on the other hand, the display device 101 determines whether the month including the day to be analyzed is one of December to February (step S1803). Here, if the month is one of December to February (step S1803: Yes), the display device 101 determines that the season corresponding to the day to be analyzed is winter (step S1804).

If the month is not any of December to February (step S1803: No), on the other hand, the display device 101 determines that the season corresponding to the day to be analyzed is spring/autumn (step S1805). Thus, the season corresponding to the day to be analyzed can be determined.

Figure 19:
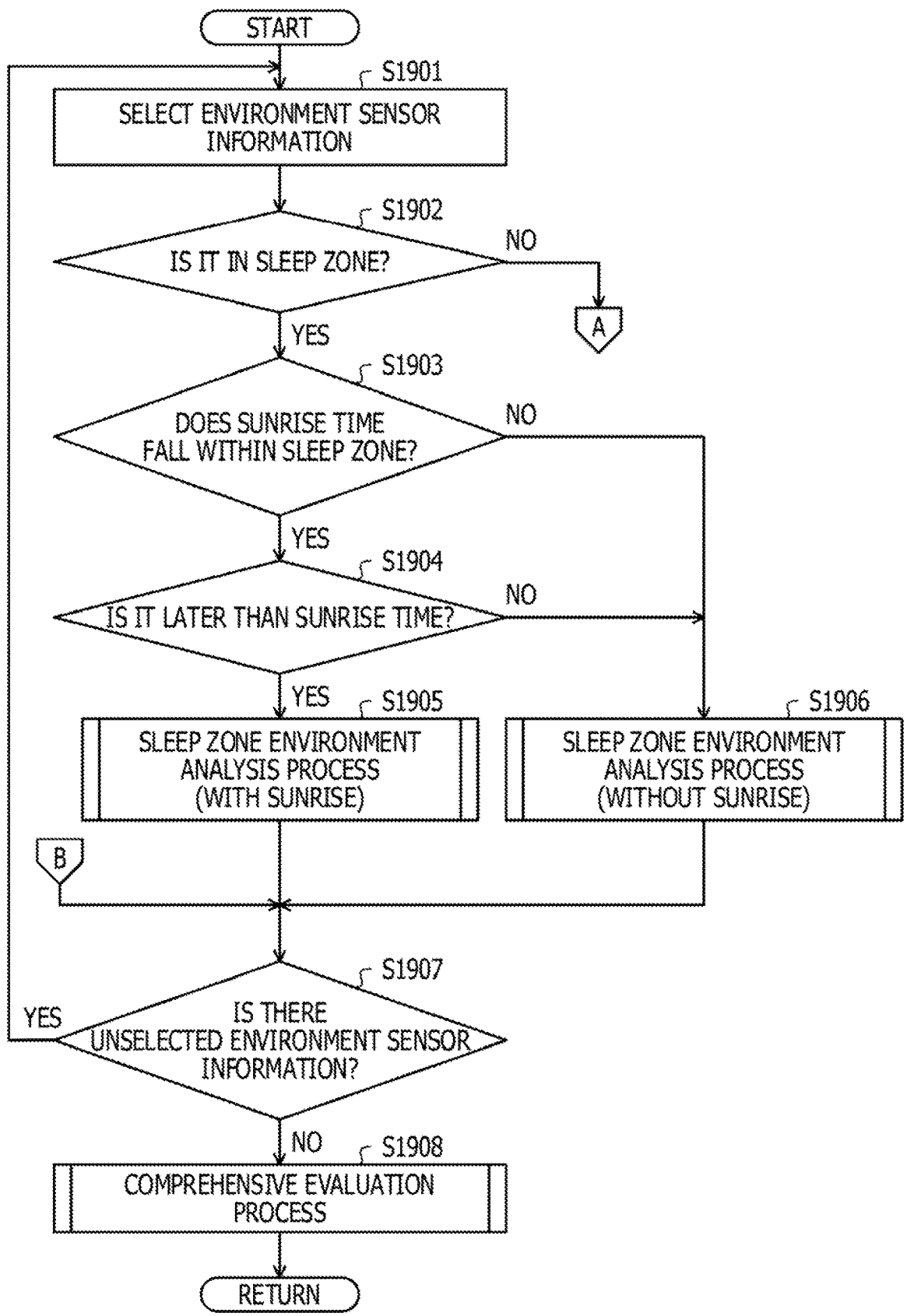
FIG. 19 is a flowchart (part 1) illustrating an example of specific procedures in an environment analysis process.
Figure 20:
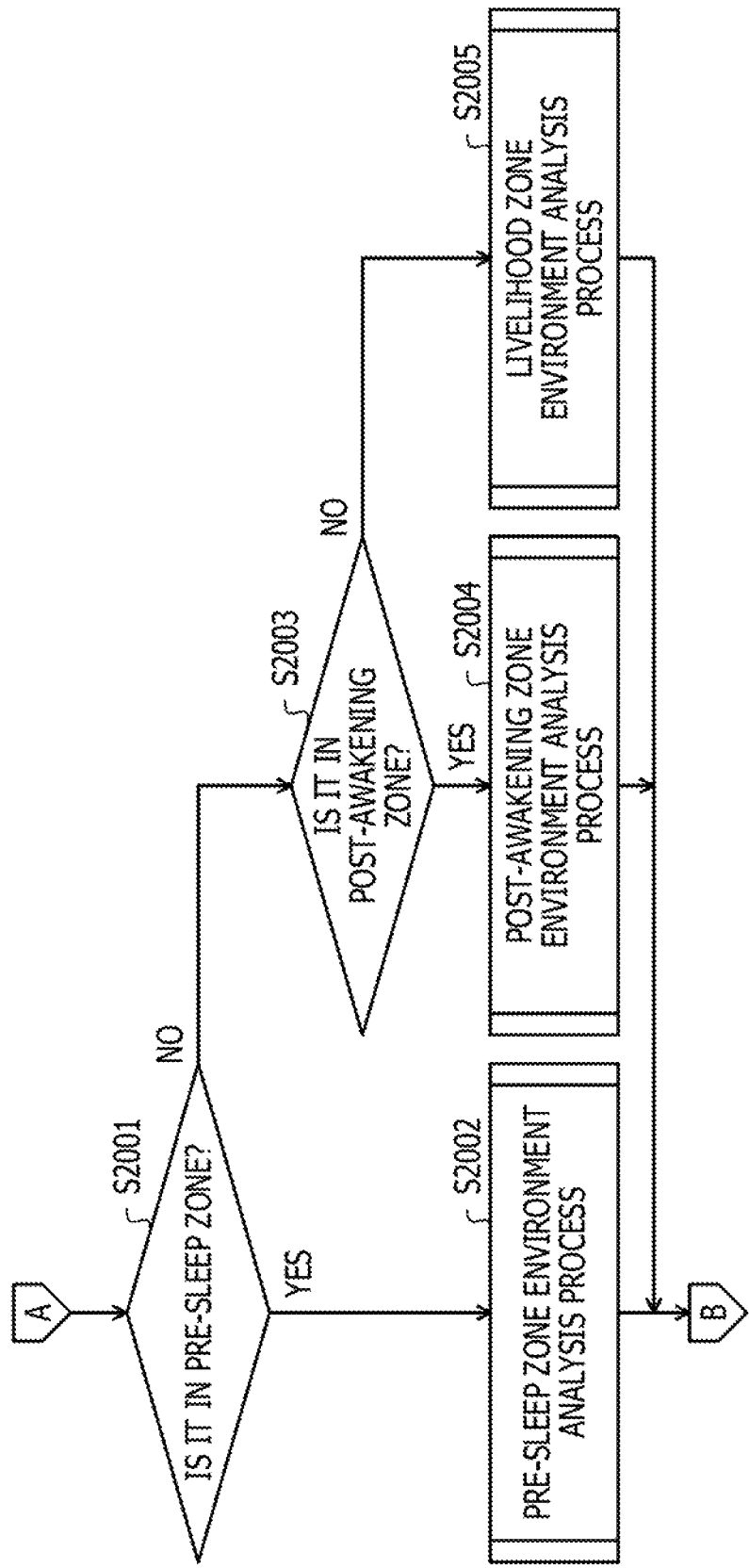
FIG. 20 is a flowchart (part 2) illustrating an example of specific procedures in the environment analysis process.

Referring now to FIGS. 19 and 20, the specific procedures in the environment analysis process in step S1708 are described.

FIGS. 19 and 20 are a flowchart illustrating an example of the specific procedures in the environment analysis process. In the flowchart in FIG. 19, the display device 101 first selects unselected environment sensor information that has not been selected in the environment sensor Information corresponding to the day to be analyzed, which has been acquired in step S1706 in FIG. 17 (step S1901).

The display device 101 then determines whether the time of the selected environment sensor information falls within the sleep zone of the day to be analyzed (step S1902). Here, if the time falls within the sleep zone (step S1902: Yes), the display device 101 determines whether the sunrise time of the analysis day identified in step S1703 in FIG. 17 falls within the sleep zone. (step S1903).

Here, if the sunrise time does not fall within the sleep zone (step S1903: No), the display device 101 moves on to step S1906. If the sunrise time falls within the sleep zone (step S1903: Yes), on the other hand, the display device 101 determines whether the time of the selected environment sensor information is the sunrise time or later (step S1904).

Here, if the time is the sunrise time or later (step S1904: Yes), the display device 101 performs a sleep zone environment analysis process (with sunrise) (step S1905). Note that the specific procedures in the sleep zone environment analysis process (with sunrise) will be described later with reference to FIG. 21.

If the time is earlier than the sunrise time (step S1904: No), on the other hand, the display device 101 performs a sleep zone environment analysis process (without sunrise) (step S1906). Note that the specific procedures in the sleep zone environment analysis process (without sunrise) will be described later with reference to FIG. 22.

The display device 101 next determines whether there is unselected environment sensor information that has not been selected in the environment sensor information corresponding to the day to be analyzed (step S1907). Here, if there is unselected environment sensor information (step S1907: Yes), the display device 101 returns to step S1901.

If there is no unselected environment sensor information (step S1907: No), on the other hand, the display device 101 performs a comprehensive evaluation process to generate a comprehensive evaluation value of the suitability in the sleep zone (step S1908), and then returns to the step in which the environment analysis process has been called. Note that the specific procedures in the comprehensive evaluation process will be described later with reference to FIG. 35.

Further, in step S1902, if the time of the selected environment sensor information does not fall within the sleep zone (step S1902: No), the display device 101 moves on to step S2001 in FIG. 20.

In the flowchart in FIG. 20, the display device 101 first determines whether the time of the selected environment sensor information falls within the pre-sleep zone of the day to be analyzed (step S2001). Here, if the time falls within the pre-sleep zone (step S2001: Yes), the display device 101 performs a pre-sleep zone environment analysis process (step S2002), and then returns to step S1907 in FIG. 19. Note that the specific procedures in the pre-sleep zone environment analysis process will be described later with reference to FIG. 23.

If the time does not fall within the pre-sleep zone (step S2001: No), on the other hand, the display device 101 determines whether the time of the selected environment sensor information falls within the post-awakening zone of the day to be analyzed (step S2003). Here, if the time falls within the post-awakening zone (step S2003: Yes), the display device 101 performs a post-awakening zone environment analysis process (step S2004), and then returns to step S1907 in FIG. 19. Note that the specific procedures in the post-awakening zone environment analysis process will be described later with reference to FIG. 24.

If the time does not fall within the post-awakening zone (step S2003: No), the display device 101 performs a livelihood zone environment analysis process (step S2005), and then returns to step S1907 in FIG. 19.

In this manner, the evaluation criteria corresponding to each zone of the sleep zone, the pre-sleep zone, the post-awakening zone, and the livelihood zone can be applied to evaluation of the suitability of the space R as a sleep environment in which the subject sleeps. Furthermore, it is possible to evaluate the suitability of the space R as a sleep environment in which the subject sleeps, taking into consideration the environment change caused by a sunrise during the sleep zone.

Figure 21:
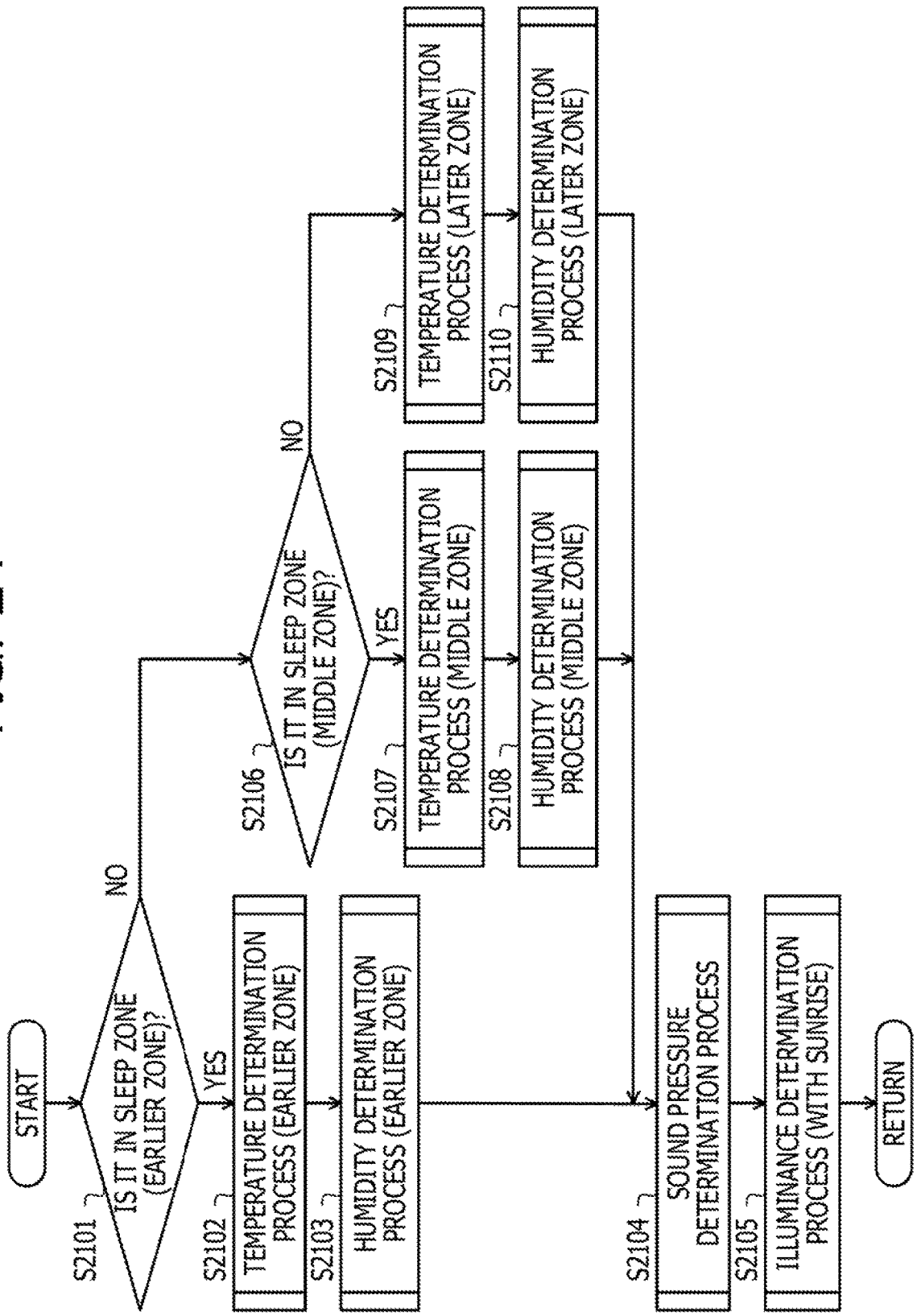
FIG. 21 is a flowchart illustrating an example of specific procedures in a sleep zone environment analysis process (with sunrise).

Referring now to FIG. 21, the specific procedures in the sleep zone environment analysis process (with sunrise) in step S1905 are described.

FIG. 21 is a flowchart illustrating an example of the specific procedures in the sleep zone environment analysis process (with a sunrise). In the flowchart in FIG. 21, the display device 101 first determines whether the time of the selected environment sensor information falls within the sleep zone (the earlier zone) (step S2101).

Here, if the time falls within the sleep zone (the earlier zone) (step S2101: Yes), the display device 101 performs a temperature determination process (the earlier zone) (step S2102). Note that the specific procedures in the temperature determination process (the earlier zone) will be described later with reference to FIG. 26.

The display device 101 next performs a humidity determination process (the earlier zone) (step S2103). Note that the specific procedures in the humidity determination process (the earlier zone) will be described later with reference to FIG. 27. The display device 101 next performs a sound pressure determination process (step S2104). Note that the specific procedures in the sound pressure determination process will be described later with reference to FIG. 28.

The display device 101 then performs an illuminance determination process (with sunrise) (step S2105), and returns to the step in which the sleep zone environment analysis process (with sunrise) has been called. Note that the specific procedures in the Illuminance determination process (with sunrise) will be described later with reference to FIG. 31.

Further, in step S2101, if the time does not fall within sleep zone (the earlier zone) (step S2101: No), the display device 101 determines whether the time of the selected environment sensor information falls within the sleep zone (the middle zone) (step S2106).

Here, if the time falls within the sleep zone (the middle zone) (step S2106: Yes), the display device 101 performs a temperature determination process (the middle zone) (step S2107). Note that the specific procedures in the temperature determination process (the middle zone) differ from those in the temperature determination process (the earlier zone) illustrated in FIG. 26 only in the evaluation criteria to be applied, and therefore, are neither illustrated in any drawing nor explained herein.

The display device 101 next performs a humidity determination process (the middle zone) (step S2108), and then moves on to step S2104. Note that the specific procedures in the humidity determination process (the middle zone) differ from those in the humidity determination process (the earlier zone) illustrated in FIG. 27 only in the evaluation criteria to be applied, and therefore, are neither illustrated in any drawing nor explained herein.

Further, in step S2106, if the time does not fall within the sleep zone (the middle zone) (step S2106: No), the display device 101 performs a temperature determination process (the later zone) (step S2109). Note that the specific procedures in the temperature determination process (the later zone) differ from those in the temperature determination process (the earlier zone) illustrated in FIG. 26 only in the evaluation criteria to be applied, and therefore, are neither illustrated in any drawing nor explained herein.

The display device 101 then performs a humidity determination process (the later zone) (step S2110), and moves on to step S2104. Note that the specific procedures in the humidity determination process (the later zone) differ from those in the humidity determination process (the earlier zone) illustrated in FIG. 27 only in the evaluation criteria to be applied, and therefore, are neither illustrated in any drawing nor explained herein.

In this manner, the suitability of the space R as a sleep environment can be evaluated with respect to the temperature, the humidity, the sound pressure, and the illuminance of the space R in the sleep zone. Further, it is possible to evaluate the suitability of the illuminance of the space R as a sleep environment, taking into consideration the environment change caused by a sunrise during the sleep zone.

Figure 22:
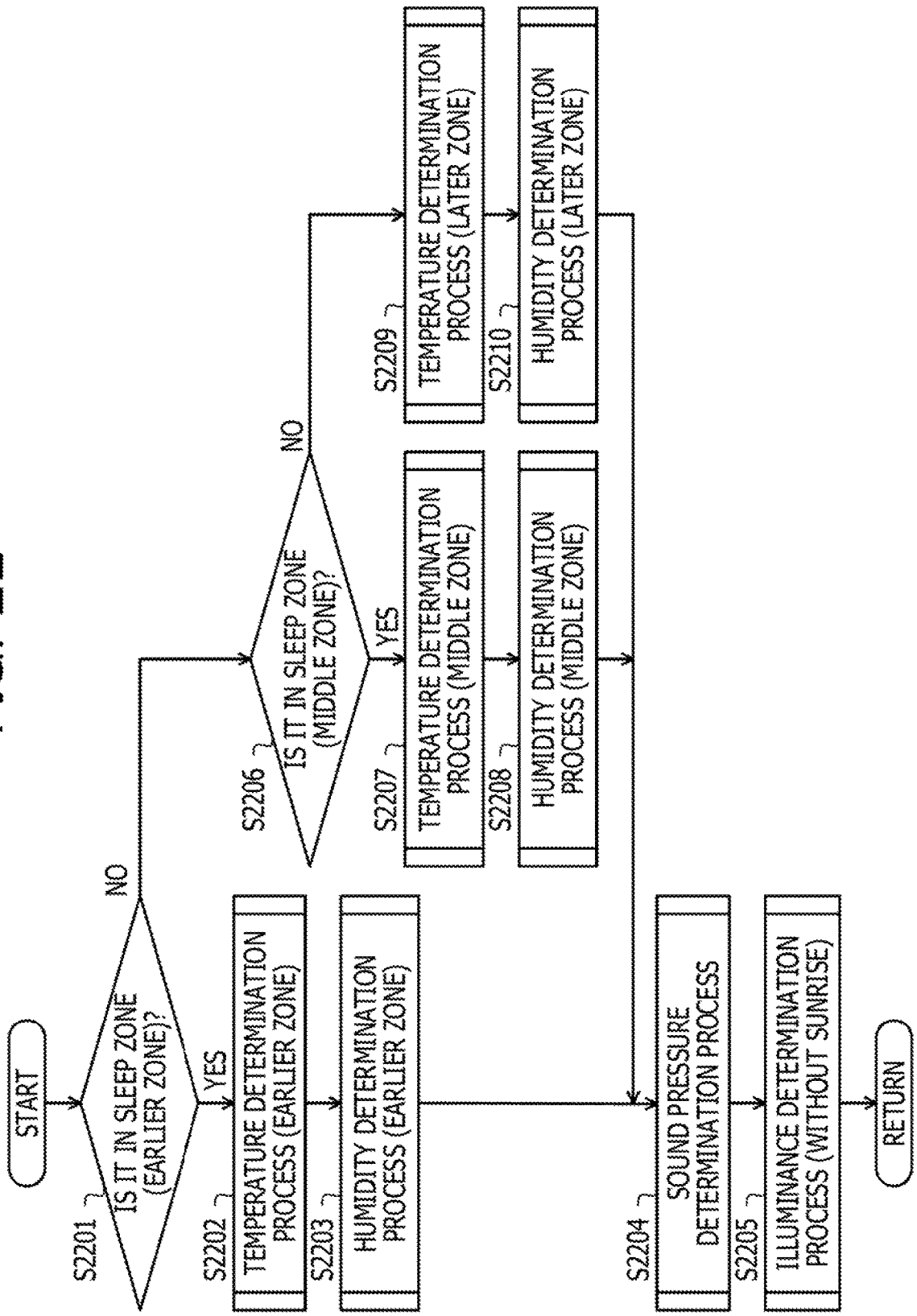
FIG. 22 is a flowchart illustrating an example of specific procedures in a sleep zone environment analysis process (without sunrise).

Referring now to FIG. 22, the specific procedures in the sleep zone environment analysis process (without sunrise) in step S1906 are described.

FIG. 22 is a flowchart illustrating an example of the specific procedures in the sleep zone environment analysis process (without sunrise). In the flowchart in FIG. 22, the display device 101 first determines whether the time of the selected environment sensor information falls within the sleep zone (the earlier zone) (step S2201).

Here, if the time falls within the sleep zone (the earlier zone) (step S2201: Yes), the display device 101 performs a temperature determination process (the earlier zone) (step S2202). The display device 101 next performs a humidity determination process (the earlier zone) (step S2203). The display device 101 next performs a sound pressure determination process (step S2204).

The display device 101 then performs an illuminance determination process (without sunrise) (step S2205), and returns to the step in which the sleep zone environment analysis process (with sunrise) has been called. Note that the specific procedures in the illuminance determination process (without sunrise) will be described later with reference to FIG. 32.

Further, in step S2201, if the time does not fall within sleep zone (the earlier zone) (step S2201: No), the display device 101 determines whether the time of the selected environment sensor information falls within the sleep zone (the middle zone) (step S2206).

Here, if the time falls within the sleep zone (the middle zone) (step S2206: Yes), the display device 101 performs a temperature determination process (the middle zone) (step S2207). The display device 101 next performs a humidity determination process (the middle zone) (step S2208), and then moves on to step S2204.

Further, in step S2206, if the time does not fall within the sleep zone (the middle zone) (step S2206: No), the display device 101 performs a temperature determination process (the later zone) (step S2209). The display device 101 then performs a humidity determination process (the later zone) (step S2210), and moves on to step S2204.

In this manner, the suitability of the space R as a sleep environment can be evaluated with respect to the temperature, the humidity, the sound pressure, and the illuminance of the space R in the sleep zone.

Figure 23:
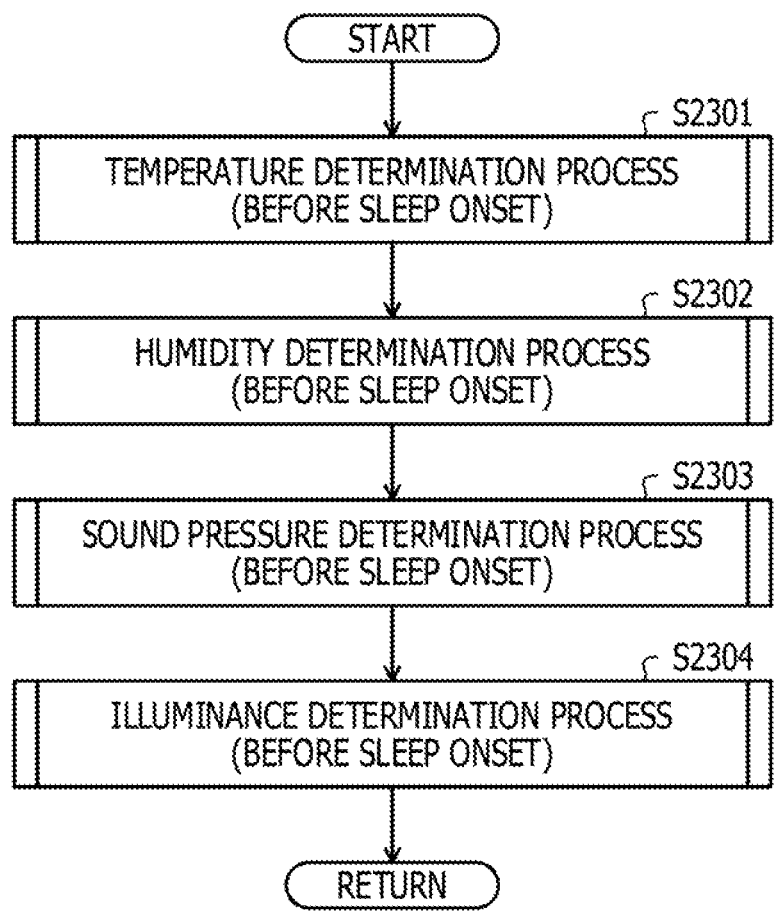
FIG. 23 is a flowchart illustrating an example of specific procedures a pre-sleep zone environment analysis process.

Referring now to FIG. 23, the specific procedures in the pre-sleep zone environment analysis process in step S2002 are described.

FIG. 23 is a flowchart illustrating an example of the specific procedures in the pre-sleep zone environment analysis process. In the flowchart in FIG. 23, the display device 101 first performs a temperature determination process (before sleep onset) (step S2301). Note that the specific procedures in the temperature determination process (before sleep onset) differ from those in the temperature determination process (the earlier zone) illustrated in FIG. 26 only in the evaluation criteria to be applied, and therefore, are neither illustrated in any drawing nor explained herein.

The display device 101 then performs a humidity determination process (before sleep onset) (step S2302). Note that the specific procedures in the humidity determination process (before sleep onset) differ from those in the humidity determination process (the earlier zone) illustrated in FIG. 27 only in the evaluation criteria to be applied, and therefore, are neither illustrated in any drawing nor explained herein. The display device 101 then performs a sound pressure determination process (before sleep onset) (step S2303). Note that the specific procedures in the sound pressure determination process (before sleep onset) will be described later with reference to FIG. 29.

The display device 101 then performs an illuminance determination process (before sleep onset) (step S2304), and returns to the step in which the pre-sleep zone environment analysis process has been called. Note that the specific procedures in the illuminance determination process (before sleep onset) will be described later with reference to FIG. 33.

In this manner, the suitability of the space R as a sleep environment can be evaluated with respect to the temperature, the humidity, the sound pressure, and the illuminance of the space R in the pre-sleep zone.

Figure 24:
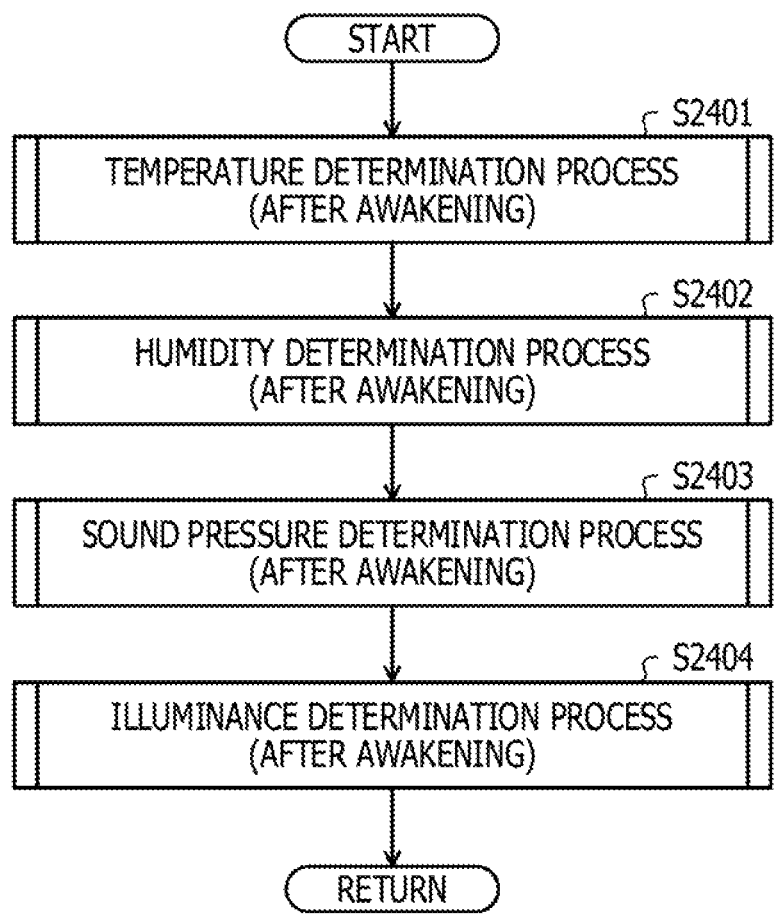
FIG. 24 is a flowchart illustrating an example of specific procedures in a post-awakening zone environment analysis process.

Referring now to FIG. 24, the specific procedures in the post-awakening zone environment analysis process in step S2004 are described.

FIG. 24 is a flowchart illustrating an example of the specific procedures in the post-awakening zone environment analysis process. In the flowchart in FIG. 24, the display device 101 first performs a temperature determination process (after awakening) (step S2401). Note that the specific procedures in the temperature determination process (after awakening) differ from those in the temperature determination process (the earlier zone) illustrated in FIG. 26 only in the evaluation criteria to be applied, and therefore, are neither illustrated in any drawing nor explained herein.

The display device 101 next performs a humidity determination process (after awakening) (step S2402). Note that the specific procedures in the humidity determination process (after awakening) differ from those in the humidity determination process (the earlier zone) illustrated in FIG. 27 only in the evaluation criteria to be applied, and therefore, are neither illustrated in any drawing nor explained herein. The display device 101 next performs a sound pressure determination process (after awakening) (step S2403). Note that the specific procedures in the sound pressure determination process (after awakening) will be described later with reference to FIG. 30.

The display device 101 then performs an illuminance determination process (after awakening) (step S2404), and returns to the step in which the post-awakening zone environment analysis process has been called. Note that the specific procedures in the illuminance determination process (after awakening) will be described later with reference to FIG. 34.

In this manner, the suitability of the space R as a sleep environment can be evaluated with respect to the temperature, the humidity, the sound pressure, and the illuminance of the space R in the post-awakening zone.

Figure 25:
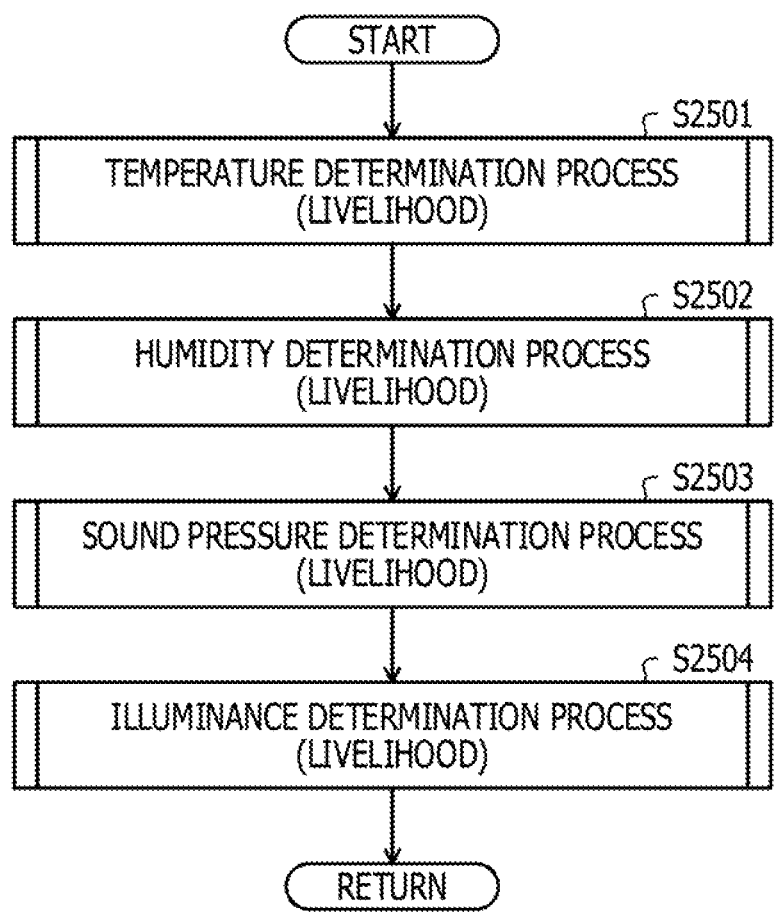
FIG. 25 is a flowchart illustrating an example of specific procedures a livelihood zone environment analysis process.

Referring now to FIG. 25, the specific procedures in the livelihood zone environment analysis process in step S2005 are described.

FIG. 25 is a flowchart illustrating an example of the specific procedures in the livelihood zone environment analysis process. In the flowchart in FIG. 25, the display device 101 first performs a temperature determination process (livelihood) (step S2501). Note that the specific procedures in the temperature determination process (livelihood) differ from those in the temperature determination process (the earlier zone) illustrated in FIG. 26 only in the evaluation criteria to be applied, and therefore, are neither illustrated in any drawing nor explained herein.

The display device 101 next performs a humidity determination process (livelihood) (step S2502). Note that the specific procedures in the humidity determination process (livelihood) differ from those in the humidity determination process (the earlier zone) illustrated in FIG. 27 only in the evaluation criteria to be applied, and therefore, are neither illustrated in any drawing nor explained herein. The display device 101 next performs a sound pressure determination process (livelihood) (step S2503). Note that the specific procedures in the sound pressure determination process (livelihood) differ from those in the sound pressure determination process illustrated in FIG. 28 only in the evaluation criteria to be applied, and therefore, are neither illustrated in any drawing nor explained herein.

The display device 101 then performs an illuminance determination process (livelihood) (step S2504), and returns to the step in which the livelihood zone environment analysis process has been called. Note that the specific procedures in the Illuminance determination process (livelihood) differ from those in the illuminance determination process (with sunrise) illustrated in FIG. 31 only in the evaluation criteria to be applied, and therefore, are neither illustrated in any drawing nor explained herein.

In this manner, the suitability of the space R as a sleep environment can be evaluated with respect to the temperature, the humidity, the sound pressure, and the illuminance of the space R in the livelihood zone. Note that, in a case where the suitability of the space R as a sleep environment in the livelihood zone is not to be evaluated, the livelihood zone environment analysis process in step S2005 may be skipped.

Figure 26:
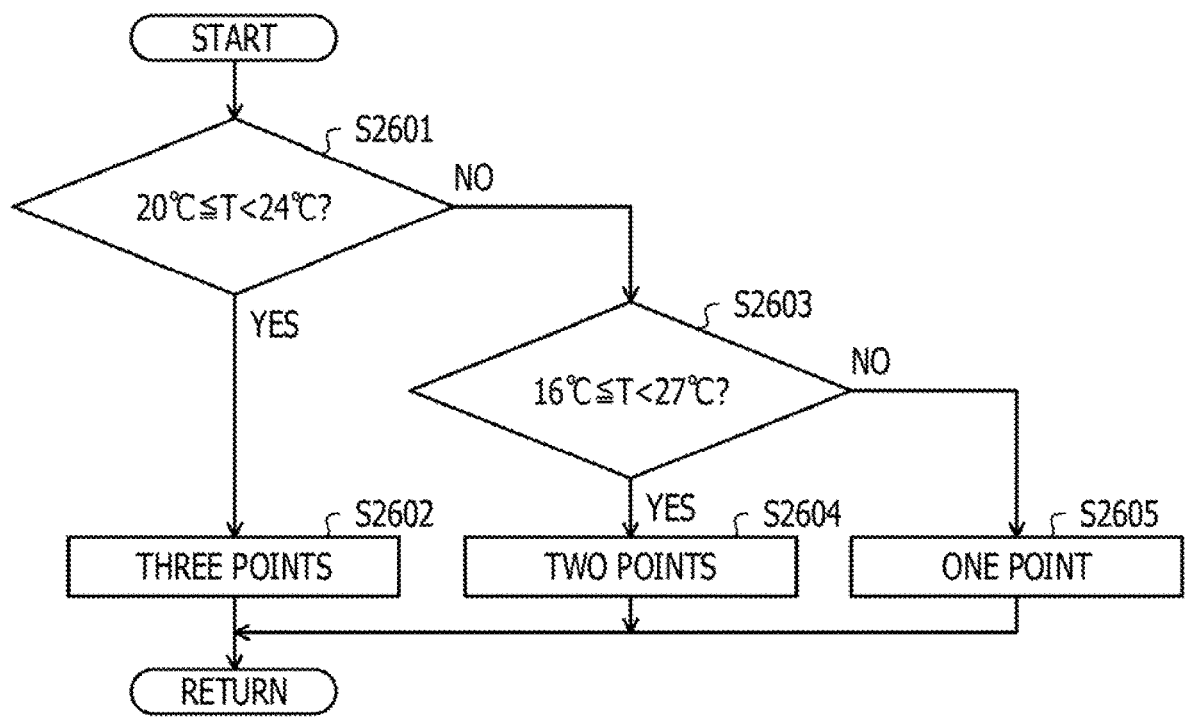
FIG. 26 is a flowchart illustrating an example of specific procedures in a temperature determination process (the earlier zone).

Referring now to FIG. 26, the specific procedures in the temperature determination process (the earlier zone) in step S2102 are described. In the temperature determination process (the earlier zone), the evaluation criteria corresponding to the season determined in step S1705 are used. Spring/autumn is described as an example of the season corresponding to the day to be analyzed herein.

FIG. 26 is a flowchart illustrating an example of the specific procedures in the temperature determination process (the earlier zone). In the flowchart in FIG. 26, the display device 101 first determines whether the temperature T in the selected environment sensor information is not lower than 20° C. but is lower than 24° C. (step S2601).

Here, if the temperature T is not lower than 20° C. but is lower than 24° C. (step S2601: Yes), the display device 101 gives three points to the suitability of the temperature of the space R (step S2602), and returns to the step in which the temperature determination process (the earlier zone) has been called. Note that the evaluation result (score) is stored into the evaluation result table 1200.

If the temperature T is lower than 20° C. or is not lower than 24° C. (step S2601: No), on the other hand, the display device 101 determines whether the temperature T in the selected environment sensor Information is not lower than 16° C. but is lower than 27° C. (step S2603). Here, if the temperature T is not lower than 16° C. but is lower than 27° C. (step S2603: Yes), the display device 101 gives two points to the suitability of the temperature of the space R (step S2604), and returns to the step in which the temperature determination process (the earlier zone) has been called.

If the temperature T is lower than 16° C. or is not lower than 27° C. (step S2603: No), on the other hand, the display device 101 gives one point to the suitability of the temperature of the space R (step S2605), and returns to the step in which the temperature determination process (the earlier zone) has been called. In this manner, it is possible to evaluate the suitability of the temperature of the space R in the sleep zone (the earlier zone), taking into consideration the fact that the environment suitable for sleep changes even within the sleep zone.

Figure 27:
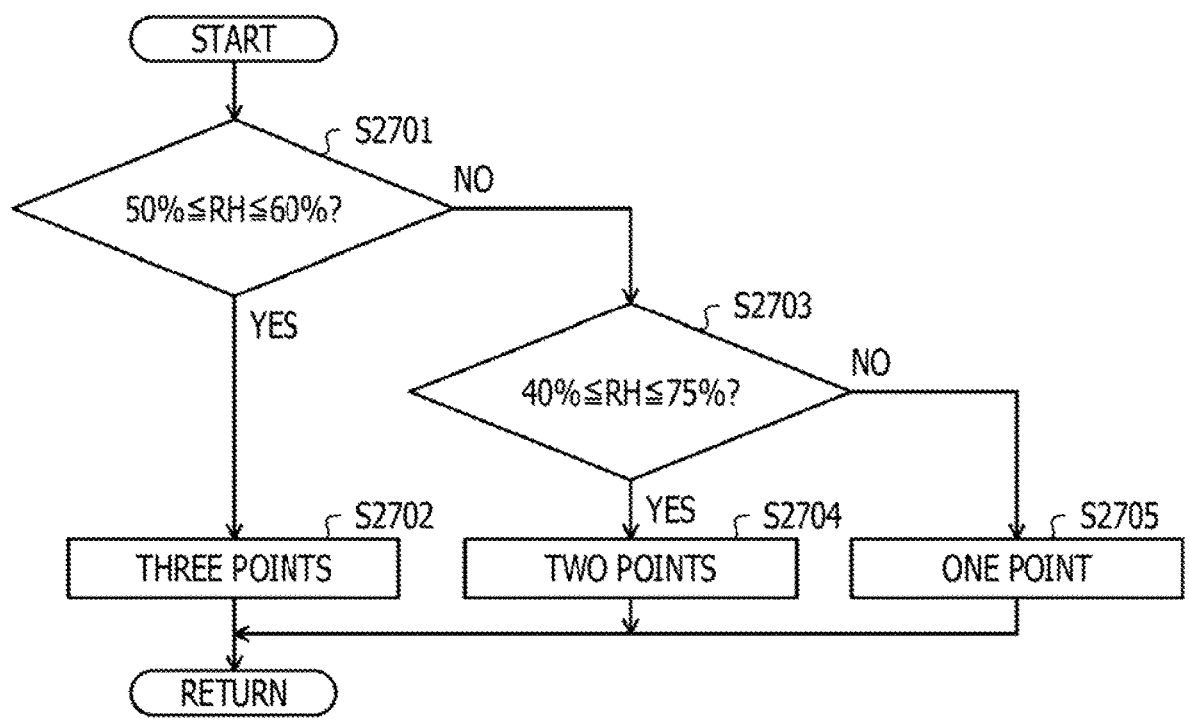
FIG. 27 is a flowchart illustrating an example of specific procedures in the humidity determination process (the earlier zone).

Referring now to FIG. 27, the specific procedures in the humidity determination process (the earlier zone) in step S2103 are described. In the humidity determination process (the earlier zone), the evaluation criteria corresponding to the season determined in step S1705 are used. Spring/autumn is described as an example of the season corresponding to the day to be analyzed herein.

FIG. 27 is a flowchart illustrating an example of the specific procedures in the humidity determination process (the earlier zone). In the flowchart in FIG. 27, the display device 101 first determines whether the humidity RH in the selected environment sensor information is not lower than 50% and is not higher than 60% (step S2701).

Here, if the humidity RH is not lower than 50% and is not higher than 60% (step S2701: Yes), the display device 101 gives three points to the suitability of the humidity of the space R (step S2702), and returns to the step in which the humidity determination process (the earlier zone) has been called. Note that the evaluation result (score) is stored into the evaluation result table 1200.

If the humidity RH is lower than 50% or is higher than 60% (step S2701: No), on the other hand, the display device 101 determines whether the humidity RH in the selected environment sensor information is not lower than 40% and is not higher than 75% (step S2703). Here, if the humidity RH is not lower than 40% and is not higher than 75% (step S2703: Yes), the display device 101 gives two points to the suitability of the humidity of the space R (step S2704), and returns to the step in which the humidity determination process (the earlier zone) has been called.

If the humidity RH is lower than 40% or is higher than 75% (step S2703: No), on the other hand, the display device 101 gives one point to the suitability of the humidity of the space R (step S2705), and returns to the step in which the humidity determination process (the earlier zone) has been called. In this manner, it is possible to evaluate the suitability of the humidity of the space R in the sleep zone (the earlier zone), taking into consideration the fact that the environment suitable for sleep changes even within the sleep zone.

Figure 28:
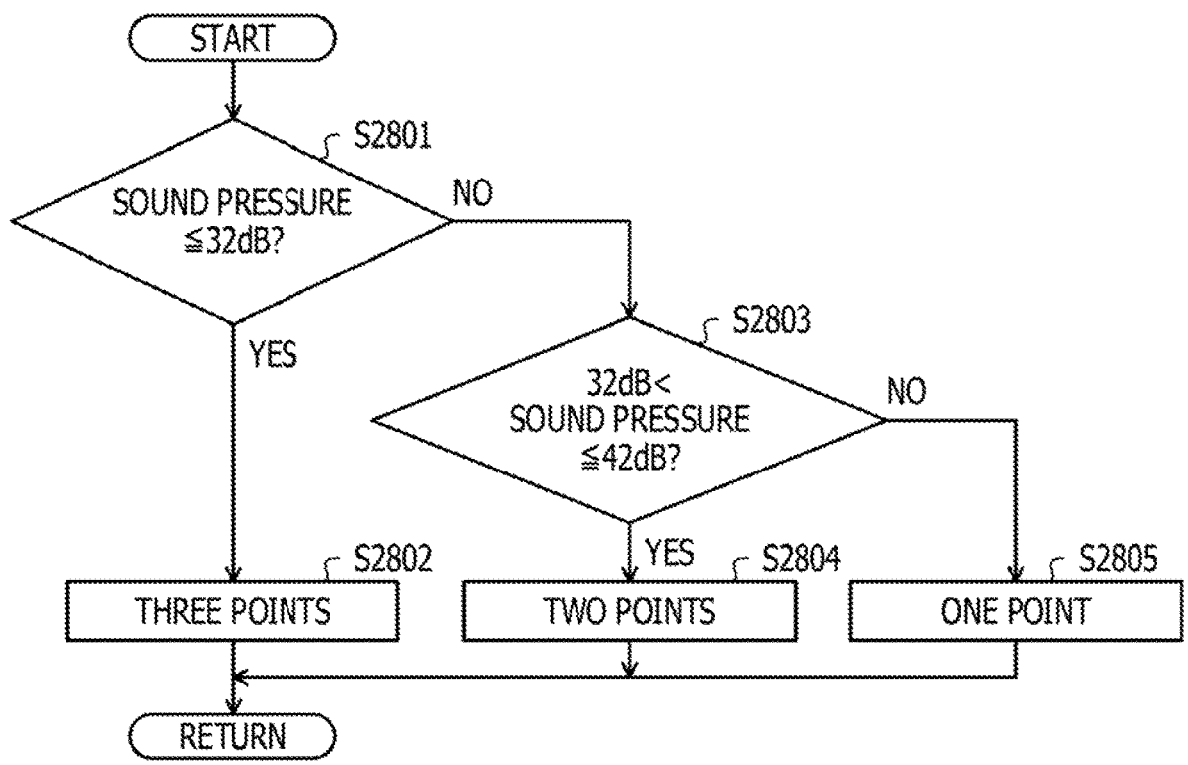
FIG. 28 is a flowchart illustrating an example of specific procedures in a sound pressure determination process.

Referring now to FIG. 28, the specific procedures in the sound pressure determination process in step S2104 are described.

FIG. 28 is a flowchart illustrating an example of the specific procedures in the sound pressure determination process. In the flowchart in FIG. 28, the display device 101 first determines whether the sound pressure in the selected environment sensor information is not higher than 32 dB (step S2801).

Here, if the sound pressure is not higher than 32 dB (step S2801: Yes), the display device 101 gives three points to the suitability of the sound pressure of the space R (step S2802), and returns to the step in which the sound pressure determination process has been called. Note that the evaluation result (score) is stored into the evaluation result table 1200.

If the sound pressure is higher than 32 dB (step S2801: No), on the other hand, the display device 101 determines whether the sound pressure in the selected environment sensor information is higher than 32 dB but is not higher than 42 dB (step S2803). Here, if the sound pressure is higher than 32 dB but is not higher than 42 dB (step S2803: Yes), the display device 101 gives two points to the suitability of the sound pressure of the space R (step S2804), and returns to the step in which the sound pressure determination process has been called.

If the sound pressure is not higher than 32 dB or is higher than 42 dB (step S2803: No), the display device 101 gives one point to the suitability of the sound pressure of the space R (step S2805), and returns to the step in which the sound pressure determination process has been called. In this manner, the suitability of the space R as a sleep environment can be evaluated with respect to the sound pressure of the space R in the sleep zone.

Figure 29:
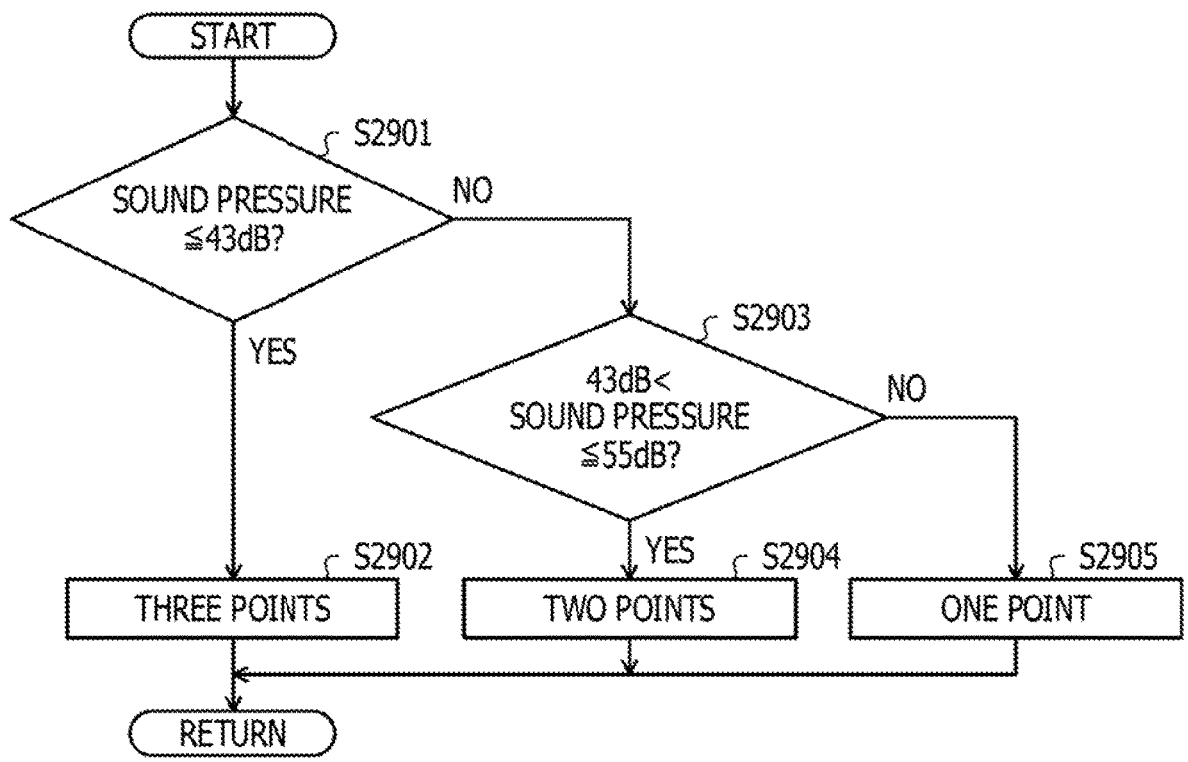
FIG. 29 is a flowchart illustrating an example of specific procedures a sound pressure determination process (before sleep onset).

Referring now to FIG. 29, the specific procedures in the sound pressure determination process (before sleep onset) in step S2303 are described.

FIG. 29 is a flowchart illustrating an example of the specific procedures in the sound pressure determination process (before sleep onset). In the flowchart in FIG. 29, the display device 101 first determines whether the sound pressure in the selected environment sensor information is not higher than 43 dB (step S2901).

Here, if the sound pressure is not higher than 43 dB (step S2901: Yes), the display device 101 gives three points to the suitability of the sound pressure of the space R (step S2902), and returns to the step in which the sound pressure determination process (before sleep onset) has been called. Note that the evaluation result (score) is stored into the evaluation result table 1200.

If the sound pressure is higher than 43 dB (step S2901: No), on the other hand, the display device 101 determines whether the sound pressure in the selected environment sensor information is higher than 43 dB but is not higher than 55 dB (step S2903). Here, if the sound pressure is higher than 43 dB but is not higher than 55 dB (step S2903: Yes), the display device 101 gives two points to the suitability of the sound pressure of the space R (step S2904), and returns to the step in which the sound pressure determination process (before sleep onset) has been called.

If the sound pressure is not higher than 43 dB or is higher than 55 dB (step S2903: No), the display device 101 gives one point to the suitability of the sound pressure of the space R (step S2905), and returns to the step in which the sound pressure determination process (before sleep onset) has been called. In this manner, it is possible to evaluate the suitability of the sound pressure of the space R in the pre-sleep zone, taking into consideration the fact that the environment suitable for sleep differs from that in the sleep zone.

Figure 30:
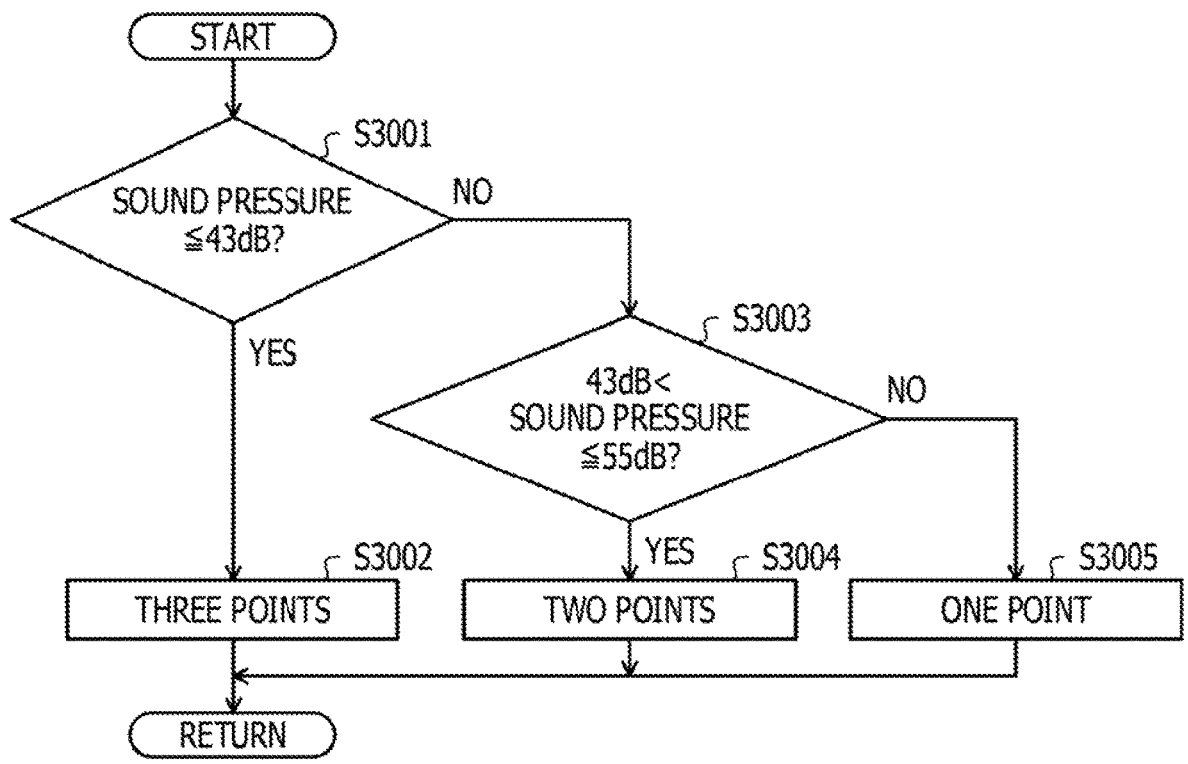
FIG. 30 is a flowchart illustrating an example of specific procedures in a sound pressure determination process (after awakening).

Referring now to FIG. 30, the specific procedures in the sound pressure determination process (after awakening) in step S2403 are described.

FIG. 30 is a flowchart illustrating an example of the specific procedures in the sound pressure determination process (after awakening). In the flowchart in FIG. 30, the display device 101 first determines whether the sound pressure in the selected environment sensor information is not higher than 43 dB (step S3001).

Here, if the sound pressure is not higher than 43 dB (step S3001: Yes), the display device 101 gives three points to the suitability of the sound pressure of the space R (step S3002), and returns to the step in which the sound pressure determination process (after awakening) has been called. Note that the evaluation result (score) is stored into the evaluation result table 1200.

If the sound pressure is higher than 43 dB (step S3001: No), on the other hand, the display device 101 determines whether the sound pressure in the selected environment sensor information is higher than 43 dB but is not higher than 55 dB (step S3003). Here, if the sound pressure is higher than 43 dB but is not higher than 55 dB (step S3003: Yes), the display device 101 gives two points to the suitability of the sound pressure of the space R (step S3004), and returns to the step in which the sound pressure determination process (after awakening) has been called.

If the sound pressure is not higher than 43 dB or is higher than 55 dB (step S3003: No), the display device 101 gives one point to the suitability of the sound pressure of the space R (step S3005), and returns to the step in which the sound pressure determination process (after awakening) has been called. In this manner, it is possible to evaluate the suitability of the sound pressure of the space R in the post-awakening zone, taking into consideration the fact that the environment suitable for sleep differs from that in the sleep zone.

Figure 31:
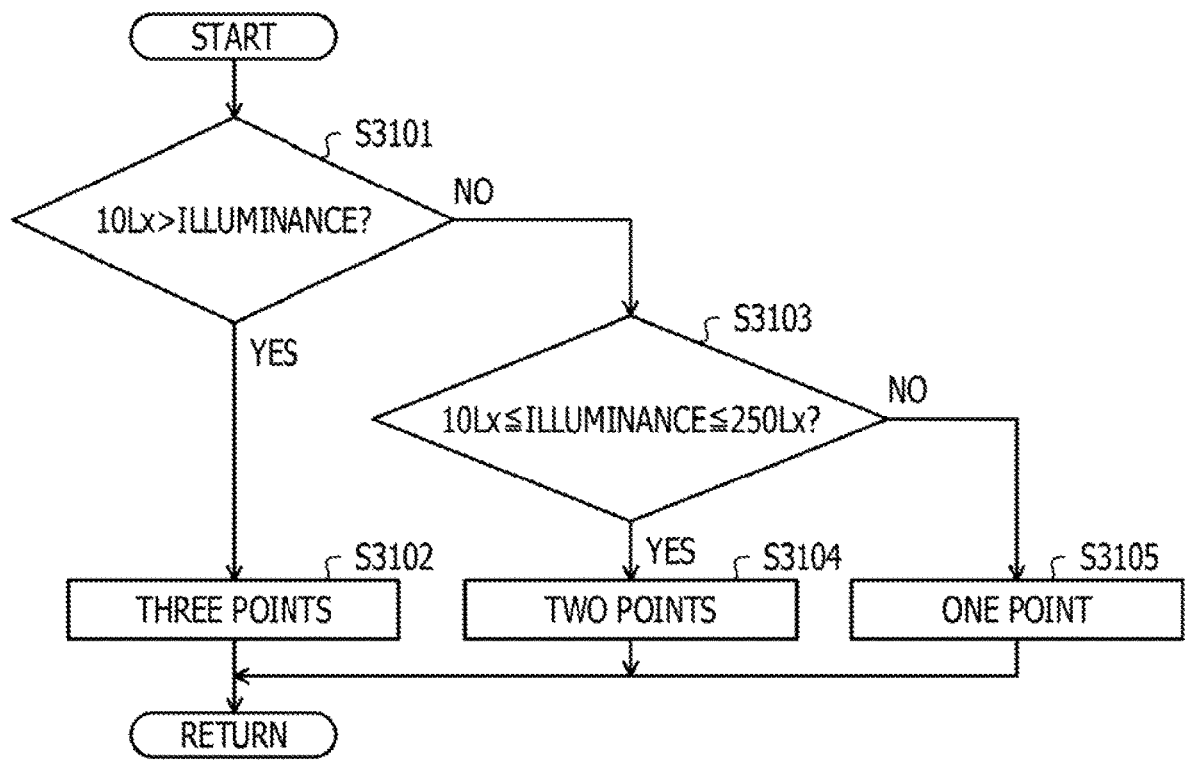
FIG. 31 is a flowchart illustrating an example of specific procedures in an illuminance determination process (with sunrise).

Referring now to FIG. 31, the specific procedures in the illuminance determination process (with sunrise) in step S2105 are described.

FIG. 31 is a flowchart illustrating an example of the specific procedures in the Illuminance determination process (with sunrise). In the flowchart in FIG. 31, the display device 101 first determines whether the Illuminance in the selected environment sensor information is lower than 10 Lx (step S3101).

Here, if the illuminance is lower than 10 Lx (step S3101: Yes), the display device 101 gives three points to the suitability of the illuminance of the space R (step S3102), and returns to the step in which the illuminance determination process (with sunrise) has been called. Note that the evaluation result (score) is stored into the evaluation result table 1200.

If the illuminance is not lower than 10 Lx (step S3101: No), on the other hand, the display device 101 determines whether the illuminance in the selected environment sensor information is not lower than 10 Lx and is not higher than 250 Lx (step 3103). Here, if the illuminance is not lower than 10 Lx and is not higher than 250 Lx (step S3103: Yes), the display device 101 gives two points to the suitability of the illuminance of the space R (step S3104), and returns to the step in which the illuminance determination process (with sunrise) has been called.

If the Illuminance is lower than 10 Lx or is higher than 250 Lx (step S3103: No), on the other hand, the display device 101 gives one point to the suitability of the Illuminance of the space R (step S3105), and returns to the step in which the illuminance determination process (with sunrise) has been called. In this manner, it is possible to evaluate the suitability of the Illuminance of the space R in the post-sunset zone in the sleep zone, taking into consideration the environment change caused by a sunrise.

Figure 32:
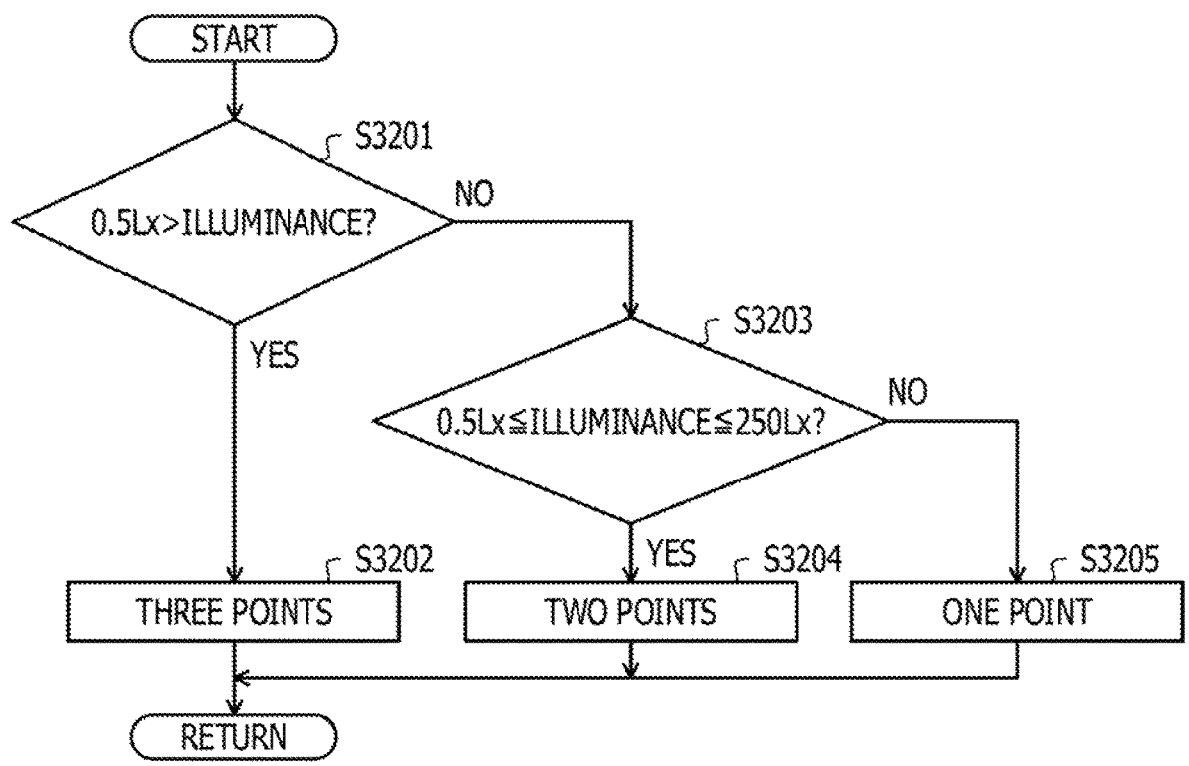
FIG. 32 is a flowchart illustrating an example of specific procedures in an illuminance determination process (without sunrise)

Referring now to FIG. 32, the specific procedures in the illuminance determination process (without sunrise) in step S2205 are described.

FIG. 32 is a flowchart illustrating an example of the specific procedures in the illuminance determination process (without sunrise). In the flowchart in FIG. 32, the display device 101 first determines whether the Illuminance in the selected environment sensor information is lower than 0.5 Lx (step S3201).

Here, if the illuminance is lower than 0.5 Lx (step S3201: Yes), the display device 101 gives three points to the suitability of the Illuminance of the space R (step S3202), and returns to the step in which the illuminance determination process (without sunrise) has been called. Note that the evaluation result (score) is stored into the evaluation result table 1200.

If the illuminance is not lower than 0.5 Lx (step S3201: No), on the other hand, the display device 101 determines whether the illuminance in the selected environment sensor information is not lower than 0.5 Lx and is not higher than 250 Lx (step S3203). Here, if the illuminance is not lower than 0.5 Lx and is not higher than 250 Lx (step S3203: Yes), the display device 101 gives two points to the suitability of the Illuminance of the space R (step S3204), and returns to the step in which the illuminance determination process (without sunrise) has been called.

If the illuminance is lower than 0.5 Lx or is higher than 250 Lx (step S3203: No), on the other hand, the display device 101 gives one point to the suitability of the illuminance of the space R (step S3205), and returns to the step in which the illuminance determination process (without sunrise) has been called. In this manner, the suitability of the space R as a sleep environment can be evaluated with respect to the Illuminance of the space R in the sleep zone.

Figure 33:
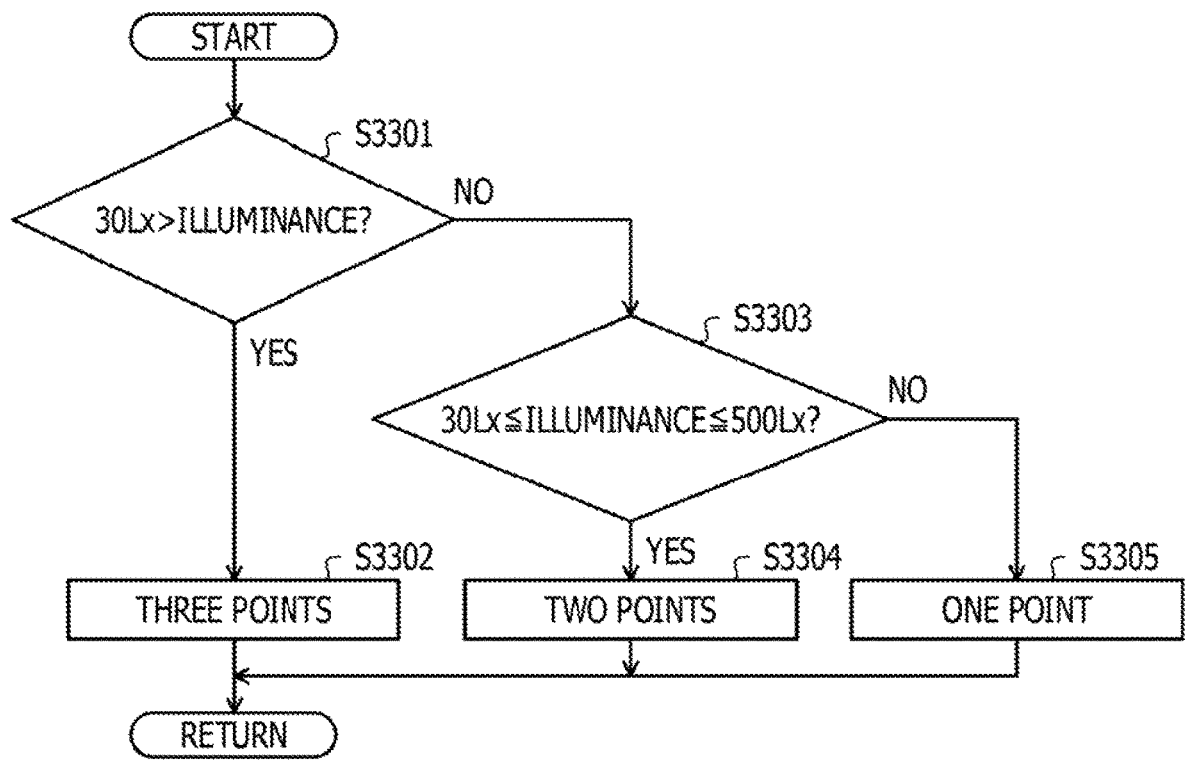
FIG. 33 is a flowchart illustrating an example of specific procedures in an illuminance determination process (before sleep onset).

Referring now to FIG. 33, the specific procedures in the Illuminance determination process (before sleep onset) in step S2304 are described.

FIG. 33 is a flowchart illustrating an example of the specific procedures in the illuminance determination process (before sleep onset). In the flowchart in FIG. 33, the display device 101 first determines whether the illuminance in the selected environment sensor information is lower than 30 Lx (step S3301).

Here, if the illuminance is lower than 30 Lx (step S3301: Yes), the display device 101 gives three points to the suitability of the illuminance of the space R (step S3302), and returns to the step in which the illuminance determination process (before sleep onset) has been called. Note that the evaluation result (score) is stored into the evaluation result table 1200.

If the Illuminance is not lower than 30 Lx (step S3301: No), on the other hand, the display device 101 determines whether the illuminance in the selected environment sensor information is not lower than 30 Lx and is not higher than 500 Lx (step S3303). Here, if the illuminance is not lower than 30 Lx and is not higher than 500 Lx (step S3303: Yes), the display device 101 gives two points to the suitability of the illuminance of the space R (step S3304), and returns to the step in which the illuminance determination process (before sleep onset) has been called.

If the Illuminance is lower than 30 Lx or is higher than 500 Lx (step S3303: No), on the other hand, the display device 101 gives one point to the suitability of the illuminance of the space R (step S3305), and returns to the step in which the illuminance determination process (before sleep onset) has been called. In this manner, it is possible to evaluate the suitability of the illuminance of the space R in the pre-sleep zone, taking into consideration the fact that the environment suitable for sleep differs from that in the sleep zone.

Figure 34:
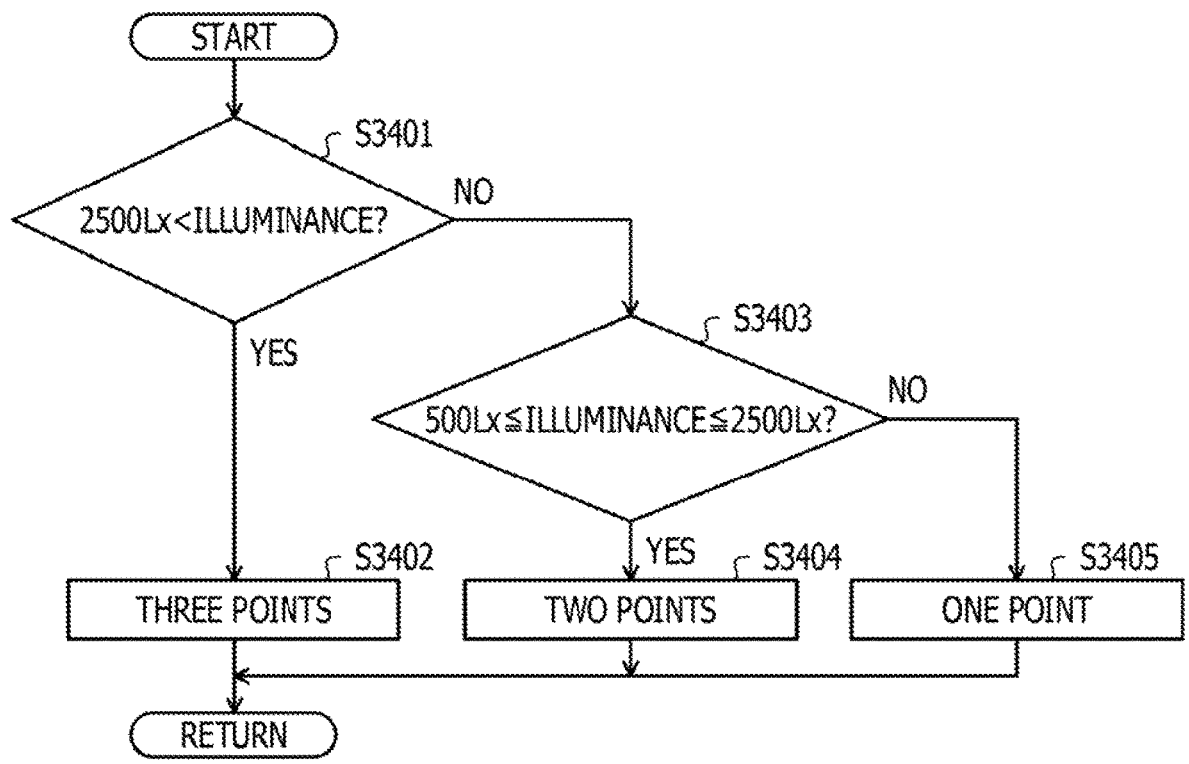
FIG. 34 is a flowchart illustrating an example of specific procedures in illuminance determination process (after awakening).

Referring now to FIG. 34, the specific procedures in the illuminance determination process (after awakening) in step S2404 are described.

FIG. 34 is a flowchart illustrating an example of the specific procedures in the illuminance determination process (after awakening). In the flowchart in FIG. 34, the display device 101 first determines whether the illuminance in the selected environment sensor information is higher than 2500 Lx (step S3401).

Here, if the illuminance is higher than 2500 Lx (step S3401: Yes), the display device 101 gives three points to the suitability of the illuminance of the space R (step S3402), and returns to the step in which the illuminance determination process (after awakening) has been called. Note that the evaluation result (score) is stored into the evaluation result table 1200.

If the illuminance is not higher than 2500 Lx (step S3401: No), on the other hand, the display device 101 determines whether the illuminance in the selected environment sensor information is not lower than 500 Lx and is not higher than 2500 Lx (step S3403). Here, if the illuminance is not lower than 500 Lx and is not higher than 2500 Lx (step S3403: Yes), the display device 101 gives two points to the suitability of the illuminance of the space R (step S3404), and returns to the step in which the illuminance determination process (after awakening) has been called.

If the illuminance is lower than 500 Lx or is higher than 2500 Lx (step S3403: No), on the other hand, the display device 101 gives one point to the suitability of the illuminance of the space R (step S3405), and returns to the step in which the illuminance determination process (after awakening) has been called. In this manner, it is possible to evaluate the suitability of the illuminance of the space R in the post-awakening zone, taking into consideration the fact that the environment suitable for sleep differs from that in the sleep zone.

Figure 35:
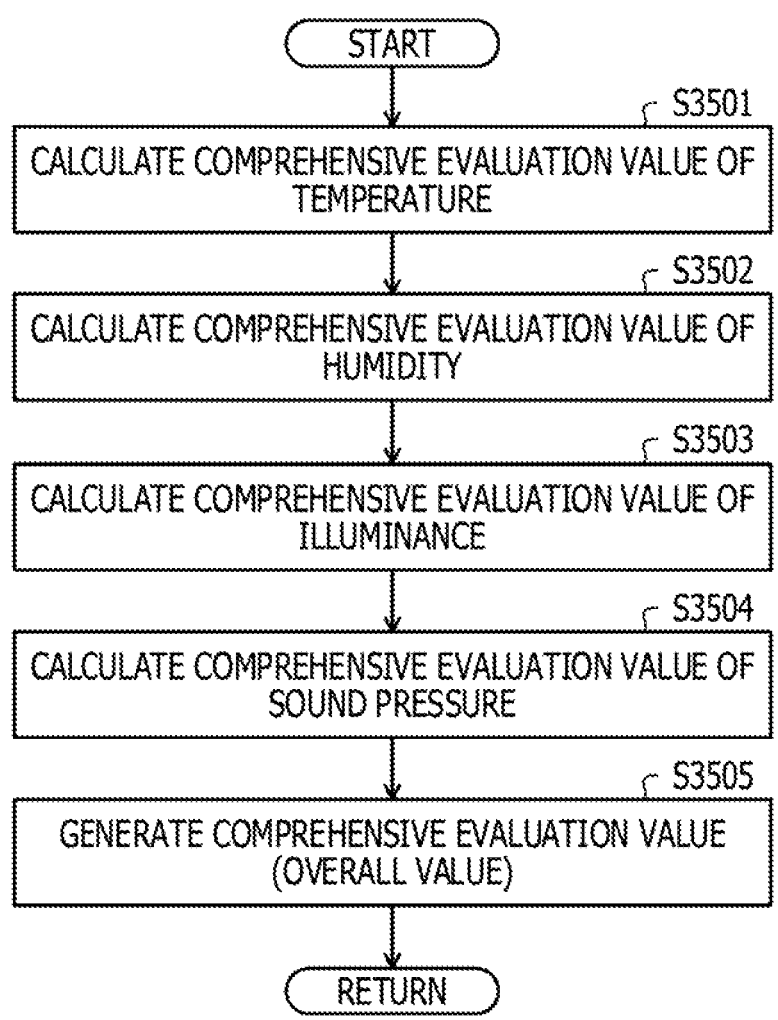
FIG. 35 is a flowchart illustrating an example of specific procedures in a comprehensive evaluation process.

Referring now to FIG. 35, the specific procedures in the comprehensive evaluation process in step S1908 are described.

FIG. 35 is a flowchart illustrating an example of the specific procedures in the comprehensive evaluation process. In the flowchart in FIG. 35, the display device 101 first refers to the evaluation result table 1200, and calculates a comprehensive evaluation value of the temperature of the space R, on the basis of the suitability (the score) of the temperature of the space R in the sleep zone (step S3501).

The calculated comprehensive evaluation value is associated with the day to be analyzed, and is stored into the comprehensive evaluation table 1300. The display device 101 then refers to the evaluation result table 1200, and calculates a comprehensive evaluation value of the humidity of the space R, on the basis of the suitability (the score) of the humidity of the space R in the sleep zone (step S3502).

The display device 101 then refers to the evaluation result table 1200, and calculates a comprehensive evaluation value of the illuminance of the space R, on the basis of the suitability (the score) of the illuminance of the space R in the sleep zone (step S3503). The display device 101 then refers to the evaluation result table 1200, and calculates a comprehensive evaluation value of the sound pressure of the space R, on the basis of the suitability (the score) of the sound pressure of the space R in the sleep zone (step S3504).

The display device 101 next refers to the comprehensive evaluation table 1300, and, on the basis of the comprehensive evaluation values of the temperature, the humidity, the illuminance, and the sound pressure on the day to be analyzed, the display device 101 generates a comprehensive evaluation value (overall value) of the suitability in the sleep zone on the day to be analyzed (step S3505). The display device 101 then returns to the step in which the comprehensive evaluation process has been called.

In this manner, the comprehensive evaluation value (the overall value) indicating the result of comprehensive evaluation of the suitability in the entire sleep zone can be generated from the respective comprehensive evaluation values of the temperature, the humidity, the illuminance, and the sound pressure of the space R in the sleep zone.

(Sleep Zone Identification Process in the Display Device 101)

Figure 36:
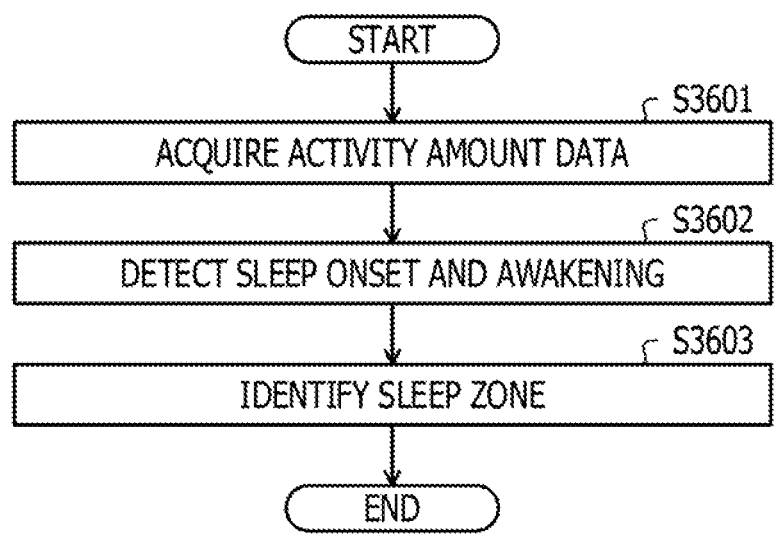
FIG. 36 is a flowchart illustrating an example of the procedures in a sleep zone identification process to be performed by the display device 101.

Referring now to FIG. 36, the procedures in a sleep zone identification process to be performed by the display device 101 are described.

FIG. 36 is a flowchart illustrating an example of the procedures in a sleep zone identification process to be performed by the display device 101. In the flowchart in FIG. 36, the display device 101 first acquires activity amount data from the activity meter 202 corresponding to the subject (step S3601). The display device 101 next detects sleep onset and awakening of the subject, on the basis of the acquired activity amount data (step S3602).

The display device 101 then identifies the sleep zone of the subject on the basis of the detection result (step S3603), and ends the series of processes according to this flowchart. In this manner, the sleep zone of the subject can be identified from the data relating to body movement and orientation recorded in the activity meter 202 of the subject.

(Sunrise/Sunset Time Calculation Process in the Display Device 101)

Figure 37:
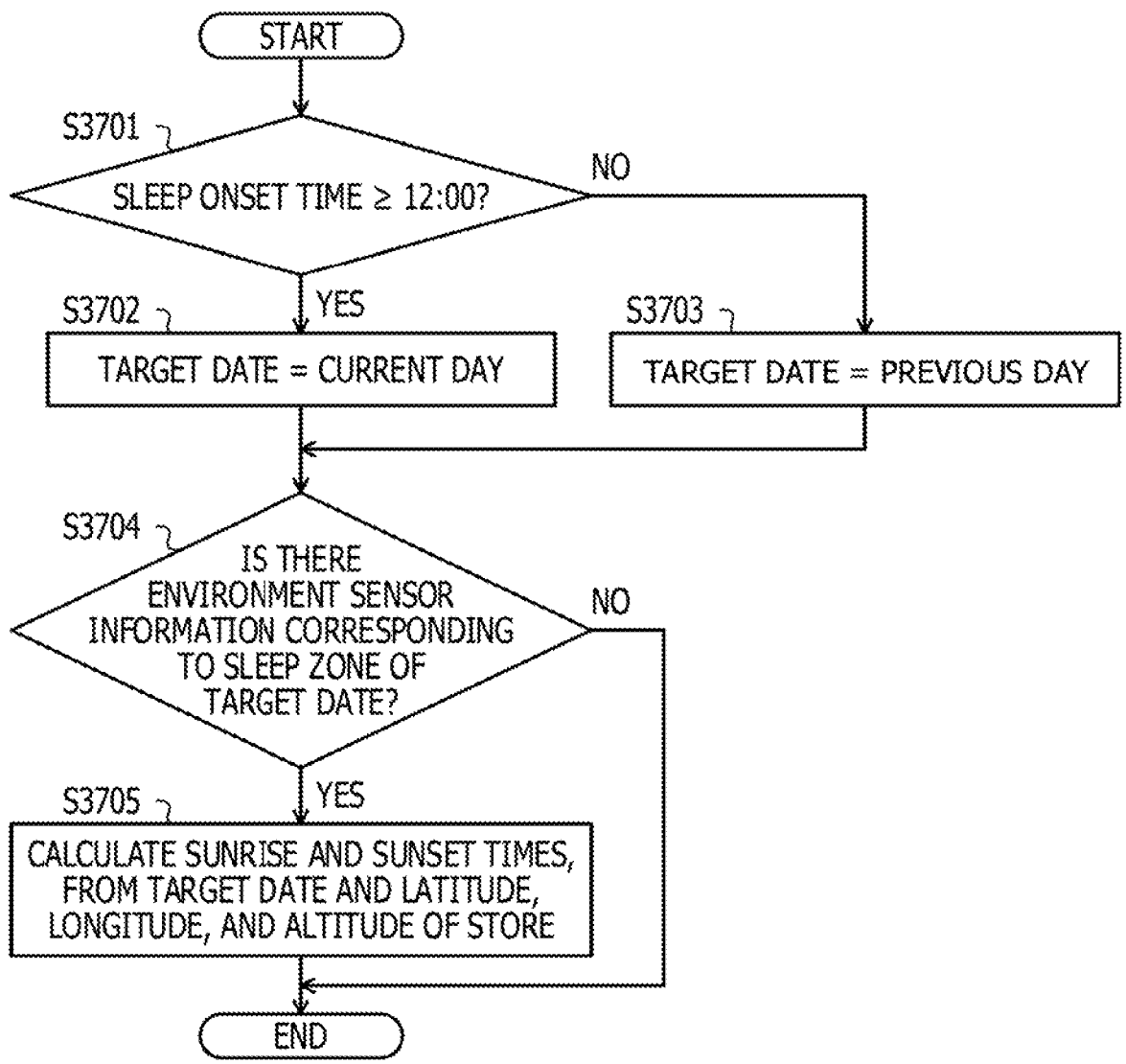
FIG. 37 is a flowchart illustrating an example of the procedures in a sunrise/sunset time calculation process to be performed by the display device 101.

Referring now to FIG. 37, the procedures in a sunrise/sunset time calculation process to be performed by the display device 101 are described.

FIG. 37 is a flowchart illustrating an example of the procedures in a sunrise/sunset time calculation process to be performed by the display device 101. In the flowchart in FIG. 37, the display device 101 first determines whether the sleep onset time on the current day (the day to be analyzed, for example) is 12:00 or later (step S3701).

Here, if the sleep onset time is 12:00 or later (step S3701: Yes), the display device 101 sets the target date for calculating the sunrise and sunset times to the date of the current day (step S3702), and moves on to step S3704. If the sleep onset time is earlier than 12:00 (step S3701: No), on the other hand, the display device 101 sets the target date for calculating the sunrise and sunset times to the date of the previous day (step S3703).

The display device 101 next refers to the environment sensor information DB 500, to determine whether there is environment sensor information corresponding to the sleep zone of the target date (step S3704). Here, if there is no environment sensor information corresponding to the sleep zone of the target date (step S3704: No), the display device 101 ends the series of processes according to this flowchart.

If there is environment sensor information corresponding to the sleep zone of the target date (step S3704: Yes), on the other hand, the display device 101 refers to the store information DB 400, to calculate the sunrise and sunset times, on the basis of the target date and the latitude, the longitude, and the altitude of the store in which the device is installed (step S3705). The display device 101 then ends the series of processes according to this flowchart.

In this manner, the sunrise and sunset times at the point at which the space R is located can be calculated, on the premise that the space R in which the subject sleeps is located at a position close to the store.

As described above, with the display device 101 according to the embodiment, it is possible to acquire data about the space R detected by the environment sensor 201 installed in the space R in which the subject sleeps. Further, when chronologically displaying the suitability of the space R as a sleep environment on the basis of the acquired data about the space R, the display device 101 can display the zone including the sleep zone, the pre-sleep zone, and the post-awakening zone of the subject 110, in a different manner from the other zones. Accordingly, it is possible to provide an easy-to-understand display of the suitability of the space R as a sleep environment in which the subject sleeps, not only in the sleep zone, but also in the pre-sleep and post-sleep zones (the pre-sleep zone and the post-awakening zone) that affect sleep.

Further, with the display device 101, it is possible to detect sleep onset and awakening of the subject on the basis of data acquired from the activity meter 202 corresponding to the subject, and identify the sleep zone of the subject on the basis of the detection result. Accordingly, the sleep zone of the subject can be automatically detected from the data relating to body movement and orientation recorded by the activity meter 202 that is worn by the subject.

Also, with the display device 101, it is possible to calculate the suitability of the space R as a sleep environment, on the basis of the temperature, the humidity, the illuminance, or the sound pressure of the space R, or any combination thereof. Accordingly, the suitability of the space R as a sleep environment can be evaluated on the basis of the temperature, the humidity, the illuminance, and the sound pressure of the space R.

Further, with the display device 101, it is possible to determine the respective lengths of the pre-sleep zone and the post-awakening zone, on the basis of the sleep efficiency based on the sleeping time and the time in bed of the subject. Accordingly, the lengths of the pre-sleep zone and the post-awakening zone can be adjusted, depending on how efficiently the subject takes sleeps.

Further, when chronologically displaying the suitability of the space R as a sleep environment, the display device 101 can display the sleep zone, the pre-sleep zone, and the post-awakening zone so as to be distinguishable from one another. Accordingly, the respective zones of the sleep zone, the pre-sleep zone, and the post-awakening zone can be easily distinguished from one another, and the suitability of each zone as a sleep environment can be readily determined.

Further, when chronologically displaying the suitability of the space R as a sleep environment, the display device 101 can display the suitability in the form of band graphs in different colors or patterns depending on the degrees of suitability. Accordingly, it is possible to provide a display that enables intuitive understanding of the chronological change in the suitability of the space R as a sleep environment.

Further, with the display device 101, shading can be put on the band graphs for the other zones (the livelihood zone, for example) that differ from the zone including the sleep zone, the pre-sleep zone, and the post-awakening zone. Thus, it is possible to make the zone of interest distinguishable from the other zones in determining the suitability of the space R as a sleep environment.

Further, with the display device 101, it is possible to display a comprehensive evaluation value of the suitability in the sleep zone, on the basis of the chronological change in the suitability during the sleep zone. Thus, the suitability of the entire sleep zone can be evaluated in a comprehensive manner.

From these facts, with the display device 101 according to the embodiment, it is possible to visualize the suitability of the space R as a sleep environment in which the subject sleeps, in an easy-to-understand mode. Accordingly, in providing consultation about a sleep environment, it is possible to give appropriate advice for increasing the quality of sleep by accurately assessing the suitability of the space R as a sleep environment, and thus, enhance the quality of services.

Note that the display method described in this embodiment can be implemented by a computer such as a personal computer or a workstation executing a prepared program. The display program is recorded in a computer-readable recording medium such as a hard disk, a flexible disk, a Compact Disc (CD)-ROM, a magneto-optical (MO) disk, a digital versatile disk (DVD), or a universal serial bus (USB) memory, and is executed after read out from the recording medium by a computer. Furthermore, the display program may be distributed via a network such as the Internet.

Regarding the embodiment described above, the following notes are further disclosed.

(Note 1) A display program for causing a computer to perform processes of:

acquiring data about a space in which a subject sleeps, the data having been detected by a first sensor installed in the space; and displaying a zone including a sleep zone, a first zone before sleep onset, and a second zone after awakening of the subject in a different mode from other zones, when chronologically displaying suitability of the space as a sleep environment on the basis of the acquired data.

(Note 2) The display program according to Note 1, which causes the computer to perform processes of:

detecting sleep onset and awakening of the subject, on the basis of data acquired from a second sensor, the second sensor sensing data about activities of the subject; and identifying the sleep zone, on the basis of the result of the detection.

(Note 3) The display program according to Note 1 or 2, wherein the data about the space indicates temperature, humidity, illuminance, or sound pressure of the space, or any combination thereof.

(Note 4) The display program according to any one of Notes 1 to 3, wherein the length of the first zone is determined by sleep efficiency based on the sleeping time and the time in bed of the subject.

(Note 5) The display program according to any one of Notes 1 to 4, wherein the length of the second zone is determined by sleep efficiency based on the sleeping time and the time in bed of the subject.

(Note 6) The display program according to any one of Notes 1 to 5, wherein the process of displaying displays the sleep zone, the first zone, and the second zone so as to be distinguishable from one another.

(Note 7) The display program according to any one of Notes 1 to 6, wherein a chronological change in the suitability is indicated by a band graph having different colors or patterns depending on degrees of the suitability.

(Note 8) The display program according to Note 7, wherein the process of displaying puts shading on the band graph for the other zone.

(Note 9) The display program according to any one of Notes 1 to 8, which causes the computer to perform a process of displaying a comprehensive value obtained by integrating the suitability in the sleep zone on the basis of the chronological change in the suitability in the sleep zone.

(Note 10) A display method for causing a computer to perform processes of:

acquiring data about a space in which a subject sleeps, the data having been detected by a first sensor installed in the space; and displaying a zone including a sleep zone, a first zone before sleep onset, and a second zone after awakening of the subject in a different mode from other zones, when chronologically displaying suitability of the space as a sleep environment on the basis of the acquired data.

(Note 11) A display device including:

an acquisition unit that acquires data about a space in which a subject sleeps, the data having been detected by a first sensor installed in the space; and a display control unit that displays a zone including a sleep zone, a first zone before sleep onset, and a second zone after awakening of the subject in a different mode from other zones, when chronologically displaying suitability of the space as a sleep environment on the basis of the acquired data.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium recording a display program for causing a computer to perform processes of:

acquiring data about a space in which a subject sleeps, the data having been detected by a first sensor installed in the space;

displaying a zone including a sleep time period from sleep onset of the subject to awakening of the subject, a first time period before the sleep onset, and a second time period after the awakening of the subject in a different mode from other time periods, when chronologically displaying suitability of the space as a sleep environment on a basis of the acquired data;

calculating sleep efficiency indicating a sleep state of the subject by using a good sleep period of the subject obtained by subtracting time periods of wake of the subject after the sleep onset from the sleep time period and a time period in bed of the subject from a bed time to a leaving time; and determining a length of the first time period based on the sleep efficiency.

2. The non-transitory computer-readable recording medium according to claim 1, which causes the computer to perform processes of:

detecting the sleep onset and the awakening of the subject, on a basis of data acquired from a second sensor, the second sensor sensing data about an activity of the subject; and identifying the sleep time period, on a basis of a detection result.

3. The non-transitory computer-readable recording medium according to claim 1, wherein the data about the space indicates temperature, humidity, illuminance, or sound pressure of the space, or any combination thereof.

4. The non-transitory computer-readable recording medium according to claim 1, wherein a length of the second time period is determined by sleep efficiency based on a sleeping time and a time in bed of the subject.

5. The non-transitory computer-readable recording medium according to claim 1, wherein the process of displaying displays the sleep time period, the first time period, and the second time period so as to be distinguishable from one another.

6. A display method for causing a computer to perform processes of;

acquiring data about a space in which a subject sleeps, the data having been detected by a first sensor installed in the space;

displaying a zone including a sleep time period from sleep onset of the subject to awakening of the subject, a first time period before the sleep onset of the subject, and a second time period after the awakening of the subject in a different mode from other time periods, when chronologically displaying suitability of the space as a sleep environment on a basis of the acquired data;

calculating sleep efficiency indicating a sleep state of the subject by using a good sleep period of the subject obtained by subtracting time periods of wake of the subject after the sleep onset from the sleep time period and a time period in bed of the subject from a bed time to a leaving time; and determining a length of the first time period based on the sleep efficiency.

7. An information processing device comprising:

a memory; and a processor coupled to the memory and configured to:

acquire data about a space in which a subject sleeps, the data having been detected by a first sensor installed in the space;

display a zone including a sleep time period from sleep onset of the subject to awakening of the subject, a first time period before the sleep onset, and a second time period after the awakening of the subject in a different mode from other time periods, when chronologically displaying suitability of the space as a sleep environment on a basis of the acquired data;

calculate sleep efficiency indicating a sleep state of the subject by using a good sleep period of the subject obtained by subtracting time periods of wake of the subject after the sleep onset from the sleep time period and a time period in bed of the subject from a bed time to a leaving time; and determine a length of the first time period based on the sleep efficiency.

* * * * *